US010435705B2

(12) United States Patent
Schultheiss et al.

(10) Patent No.: US 10,435,705 B2
(45) Date of Patent: Oct. 8, 2019

(54) FUNGAL RESISTANT PLANTS EXPRESSING HCP6

(71) Applicant: BASF PLANT SCIENCE COMPANY GMBH, Ludwigshafen (DE)

(72) Inventors: Holger Schultheiss, Boehl-Iggelheim (DE); Ralf Flachmann, Limburgerhof (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 14/763,659

(22) PCT Filed: Jan. 10, 2014

(86) PCT No.: PCT/EP2014/050397
§ 371 (c)(1),
(2) Date: Jul. 27, 2015

(87) PCT Pub. No.: WO2014/117990
PCT Pub. Date: Aug. 7, 2014

(65) Prior Publication Data
US 2015/0361443 A1    Dec. 17, 2015

(30) Foreign Application Priority Data

Jan. 29, 2013 (EP) .................................... 13152971

(51) Int. Cl.
*C12N 15/82* (2006.01)
*A01H 5/10* (2018.01)
*C07K 14/415* (2006.01)

(52) U.S. Cl.
CPC .......... *C12N 15/8282* (2013.01); *A01H 5/10* (2013.01); *C07K 14/415* (2013.01); *C12N 15/8216* (2013.01)

(58) Field of Classification Search
None
See application file for complete search history.

(56) References Cited

FOREIGN PATENT DOCUMENTS

| EP | 1 033 405 A2 | 9/2000 |
|---|---|---|
| WO | WO-2012/172498 A1 | 12/2012 |
| WO | WO-2013/001435 A1 | 1/2013 |
| WO | WO-2013/092275 A2 | 6/2013 |
| WO | WO-2013/093738 A1 | 6/2013 |
| WO | WO-2013/149801 A1 | 10/2013 |
| WO | WO-2013/149804 A1 | 10/2013 |
| WO | WO-2013/152917 A1 | 10/2013 |
| WO | WO-2014/024090 A2 | 2/2014 |
| WO | WO-2014/024102 A1 | 2/2014 |
| WO | WO-2014/041444 A1 | 3/2014 |
| WO | WO-2014/076614 A1 | 5/2014 |
| WO | WO-2014/076659 A1 | 5/2014 |
| WO | WO-2014/117988 A1 | 8/2014 |
| WO | WO-2014/117990 A1 | 8/2014 |
| WO | WO-2014/118018 A1 | 8/2014 |
| WO | WO-2014/135682 A1 | 9/2014 |

OTHER PUBLICATIONS

Fourgoux-Nicol et al (1999, Plant Molecular Biology 40: 857-872).*
Guo et al (Proc. Natl. Acad. Sci. USA 101:9205-9210, 2004).*
Hill et al. Biochem. Biophys. Res. Comm. 244:573-577, 1998).*
Friedberg (Automated protein function prediction—the genomic challenge. Brief. Bioinformatics. 7: 225-242, 2006).*
Borhan et al., " WRR4, a broad-spectrum TIR-NB-LRR gene from *Arabidopsis thaliana* that confers white rust resistance in transgenic oilseed *Brassica* crops", *Mol. Plant Pathol.* 11(2): 283-91 (2010) (Accessed from ResearchGate Sep. 21, 2016).
GenBank Accession No. NP_176044, "Disease resistance protein (TIR-NBS-LRR class) family [*Arabidopsis thaliana*]" dated Sep. 12, 2016.
Office Action, Chinese patent application No. 201480006248.7, dated Sep. 21, 2016.
Borhan et al., "WRR4 encodes a TIR-NB-LRR protein that confers broad-spectrum white rust resistance in *Arabidopsis thaliana* to four physiological races of *Albugo candida*", MPMI. 21(6): 757-68 (2008).
Borhan et al., "WRR4, a broad-spectrum TIR-NB-LRR gene from *Arabidopsis thaliana* that confers white rust resistance in transgenic oilseed *Brassica* crops", *Mol. Plant Pathol.* 11(2): 283-91 (2010).
Dangl et al., "Plant pathogens and integrated defence responses to infection", *Nature*, 411: 826-33 (2001).
EMBL Accession No. AAG51507, "*Arabdopsis thaliana* protein fragment SEQ ID No. 65379" dated Oct. 18, 2000.
EMBL Accession No. AEE33403, "Wheat gliadin/glutein epitope SEQ ID No. 89" dated Feb. 9, 2006.
European Search Report for Application No. EP 13 15 2971 dated Jun. 13, 2013.
Godoy et al., "Diagrammatic scale for assessment of soybean rust severity", *Fitopatol. Bras.* 31(1): 63-8 (2006).

(Continued)

*Primary Examiner* — Medina A Ibrahim
(74) *Attorney, Agent, or Firm* — Marshall, Gerstein & Borun LLP

(57) ABSTRACT

The present invention relates to a method of increasing resistance against fungal pathogens of the family Phacosporaceae in plants and/or plant cells. This is achieved by increasing the expression of an HCP6 protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the family Phacopsoraceae, and to recombinant expression vectors comprising a sequence that is identical or homologous to a sequence encoding an HCP6 protein.

Figure 1:
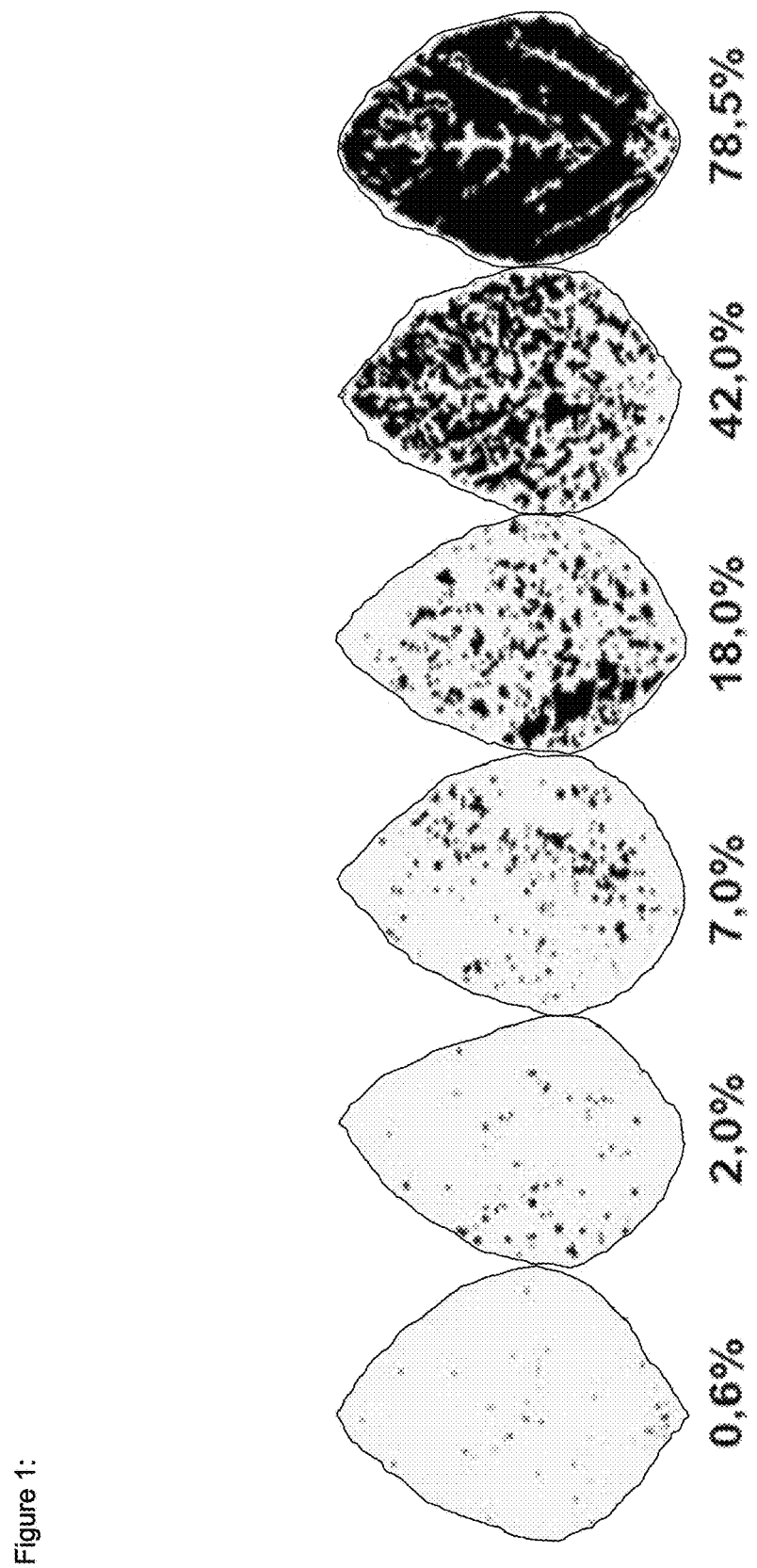

24 Claims, 20 Drawing Sheets
Specification includes a Sequence Listing.

(56) References Cited

OTHER PUBLICATIONS

Heath, "Cellular interactions between biotrophic fungal pathogens and host or nonhost plants", *Can. J. Plant Pathol.*, 24: 259-64 (2002).

Hyten et al., "Bulked segregant analysis using the GoldenGate assay to locate the Rpp3 locus that confers resistance to soybean rust in soybean", *Crop Science*, 49: 265-71 (2009).

International Search Report and Written Opinion for Application No. PCT/EP2014/050397 dated Mar. 20, 2014.

Meyers et al., "Genome-wide analysis of NBS-LRR-encoding genes in *Arabidopsis*", *Plant Cell*, 15: 809-34 (2003).

Neu et al., "Cytological and molecular analysis of the *Hordeum vulgare-Puccinia triticina* nonhost interaction", MPMI, 16(7): 626-33 (2003).

Rytter et al., "Additional alternative hosts of *Phakopsora pachyrhizi*, causal agent of soybean rust", *Plant Dis.* 68(9): 818-9 (1984).

Sinclair et al., (eds.) Proceedings of the Soybean Rust Workshop, Aug. 9-11, 1995. Urbana, IL: National Soybean Research Laboratory, (1995).

Smith et al., "Known host crops of *Phakopsora pachyrhizi* causal agent of soybean rust (SBR)", Internet Citation, 1-6 (2006).

Young, "The genetic architecture of resistance", *Curr. Opin. Plant Biol.* 3: 285-90 (2000).

\* cited by examiner

Figure 3:

Figure 3 continued:

```
                           421                                                                         480
CDS2-AT1G56520.2    (367)  GCTTTTAAAGAAACTTGTGCTCAATAAACAGAGGAGGAGAGAGGCAAAATGGACCTAAGCT
full-length genomic (421)  GCTTTTAAAGAAACTTGTGCTCAATAAACAGAGGAGGAGAGCAAAATGGACCTAAGCT
HCP6                (367)  GCTTTTAAAGAAACTTGTGCTCAATAAACAGAGGAGGAGAGCAAAATGGACCTAAGCT
HCP6_opt            (367)  GCCTTTAAAGAGACTTGCGCTCACAGACCGAAGAGAGAACCTCAAAGTGGACTCAGGCT
                           481                                                                         540
CDS2-AT1G56520.2    (427)  TTGACCTAGTGGGCAAGCATTGCCGAAGACTTTAAACACTGG-----------------
full-length genomic (481)  TTGACCTAGTGGGCAAGCATTGCCGGAGAAGACTTTAAACACTGTTGTATTTACTTAA
HCP6                (427)  TTGACCTAGTGGGCAAGCATTGCCGGAGAAGACTTTAAACACTGG-----------------
HCP6_opt            (427)  CCTTACCTACGTGGGTAATATTGCCGGCGAGCACTTAAGCACTGG-----------------
                           541                                                                         600
CDS2-AT1G56520.2    (472)  ------------------------------------------------------------
full-length genomic (541)  AGCAAATCATTCTTTAGTATATTTGATAAATTCATCAAATTTGGTTCTTATTACTGTA
HCP6                (472)  ------------------------------------------------------------
HCP6_opt            (472)  ------------------------------------------------------------
                           601                                                                         660
CDS2-AT1G56520.2    (472)  ------------------------------------------------------------
full-length genomic (601)  GGGTTGTAAGCTTTTGCTAATTGATTAATGAAGCTTTAACTTTAAGTAGTATTGA
HCP6                (472)  ------------------------------------------------------------
HCP6_opt            (472)  ------------------------------------------------------------
                           661                                                                         720
CDS2-AT1G56520.2    (472)  ------------------------------------------------------------
full-length genomic (661)  CAGGATTTTGCTATGTTAGTCTGTAATGATACCGTCATTTCATTGCTTACTATACTT
HCP6                (472)  ------------------------------------------------------------
HCP6_opt            (472)  ------------------------------------------------------------
                           721                                                                         780
CDS2-AT1G56520.2    (472)  ------------------------------------------------------------
full-length genomic (721)  ATAAATACAATTTTTAAGTATATTTCATCAAATTTGCTTCCTTATTACTGTTA
HCP6                (472)  ------------------------------------------------------------
HCP6_opt            (472)  ------------------------------------------------------------
                           781                                                                         840
CDS2-AT1G56520.2    (472)  ------------------------------------------------------------
full-length genomic (781)  TATTCCGTCGTTAGAATATCACGTATAATTAATTAATCGATTGCATTCTAATTTAGA
HCP6                (472)  ------------------------------------------------------------
HCP6_opt            (472)  ------------------------------------------------------------
```

```
                              1                                                  50
CDS2-AT1G56520.2       (1)   MASSSSSPRNWRYNVFTSFHGPDVRIKFLSHLRQQFIYNGITMFDDNGIE
    HCP6-protein       (1)   MASSSSSPRNWRYNVFTSFHGPDVRIKFLSHLRQQFIYNGITMFDDNGIE
HCP6_opt protein       (1)   MASSSSSPRNWRYNVFTSFHGPDVRIKFLSHLRQQFIYNGITMFDDNGIE
                              51                                                 100
CDS2-AT1G56520.2      (51)   RSQIIAPALKKAIGESRIAILLLSKNYASSSWSLDELLEILKCKEDIGQI
    HCP6-protein      (51)   RSQIIAPALKKAIGESRIAILLLSKNYASSSWSLDELLEILKCKEDIGQI
HCP6_opt protein      (51)   RSQIIAPALKKAIGESRIAILLLSKNYASSSWSLDELLEILKCKEDIGQI
                              101                                                150
CDS2-AT1G56520.2     (101)   VMTVFYEVDPSDVRNQTGDFGIAFKETCAHKTEEERQKWTQALTYVGNIA
    HCP6-protein     (101)   VMTVFYEVDPSDVRNQTGDFGIAFKETCAHKTEEERQKWTQALTYVGNIA
HCP6_opt protein     (101)   VMTVFYEVDPSDVRNQTGDFGIAFKETCAHKTEEERQKWTQALTYVGNIA
                              151                                                200
CDS2-AT1G56520.2     (151)   GEDFKHWPNEARMIEKIARDVSDILNVTPCRDFDGMVGLNDHLREMESLL
    HCP6-protein     (151)   GEDFKHWPNEARMIEKIARDVSDILNVTPCRDFDGMVGLNDHLREMESLL
HCP6_opt protein     (151)   GEDFKHWPNEARMIEKIARDVSDILNVTPCRDFDGMVGLNDHLREMESLL
                              201                                                250
CDS2-AT1G56520.2     (201)   DLKNDGVKIVGISGPAGIGKSTIATALHGRLSNMFQRTCFVDNLRESYKI
    HCP6-protein     (201)   DLKNDGVKIVGISGPAGIGKSTIATALHGRLSNMFQRTCFVDNLRESYKI
HCP6_opt protein     (201)   DLKNDGVKIVGISGPAGIGKSTIATALHGRLSNMFQRTCFVDNLRESYKI
                              251                                                300
CDS2-AT1G56520.2     (251)   GLDEYRLKLHLQQQLLAYVLNQDKIRVGHLSVMKERLDDLRVLIILDDVE
    HCP6-protein     (251)   GLDEYRLKLHLQQQLLAYVLNQDKIRVGHLSVMKERLDDLRVLIILDDVE
HCP6_opt protein     (251)   GLDEYRLKLHLQQQLLAYVLNQDKIRVGHLSVMKERLDDLRVLIILDDVE
                              301                                                350
CDS2-AT1G56520.2     (301)   HLYQLEALADIRWFGPGSRVIVTTENREILLQHGIKDIYHVGFPSEGEAL
    HCP6-protein     (301)   HLYQLEALADIRWFGPGSRVIVTTENREILLQHGIKDIYHVGFPSEGEAL
HCP6_opt protein     (301)   HLYQLEALADIRWFGPGSRVIVTTENREILLQHGIKDIYHVGFPSEGEAL
                              351                                                400
CDS2-AT1G56520.2     (351)   MIFCLSAFRQPSPPYGFLKLTYEVASICGNLPLGLHVLGTLLWGKSQADW
    HCP6-protein     (351)   MIFCLSAFRQPSPPYGFLKLTYEVASICGNLPLGLHVLGTLLWGKSQADW
HCP6_opt protein     (351)   MIFCLSAFRQPSPPYGFLKLTYEVASICGNLPLGLHVLGTLLWGKSQADW
                              401                                                450
CDS2-AT1G56520.2     (401)   IEELPRLKDCLDGRIESVLKVGYESLYEKDQALFLLIAVYFNYDYVDYVT
    HCP6-protein     (401)   IEELPRLKDCLDGRIESVLKVGYESLYEKDQALFLLIAVYFNYDYVDYVT
HCP6_opt protein     (401)   IEELPRLKDCLDGRIESVLKVGYESLYEKDQALFLLIAVYFNYDYVDYVT
                              451                                                500
CDS2-AT1G56520.2     (451)   SMLENTNVLDVRLGLKKLANRCLIQIDIDHNRKSRVVMNRLLQVMAREVI
    HCP6-protein     (451)   SMLENTNVLDVRLGLKKLANRCLIQIDIDHNRKSRVVMNRLLQVMAREVI
HCP6_opt protein     (451)   SMLENTNVLDVRLGLKKLANRCLIQIDIDHNRKSRVVMNRLLQVMAREVI
                              501                                                550
CDS2-AT1G56520.2     (501)   SRQKISKRKILEDPQDICYVLEEAKGKGSALGLSLDVAEIKELVINKKAF
    HCP6-protein     (501)   SRQKISKRKILEDPQDICYVLEEAKGKGSALGLSLDVAEIKELVINKKAF
HCP6_opt protein     (501)   SRQKISKRKILEDPQDICYVLEEAKGKGSALGLSLDVAEIKELVINKKAF
                              551                                                600
CDS2-AT1G56520.2     (551)   KKMCNLLILKVFNGTDPRDSKLHVPEEMELPSSIRLLHWEAYPRKSFRFG
    HCP6-protein     (551)   KKMCNLLILKVFNGTDPRDSKLHVPEEMELPSSIRLLHWEAYPRKSFRFG
HCP6_opt protein     (551)   KKMCNLLILKVFNGTDPRDSKLHVPEEMELPSSIRLLHWEAYPRKSFRFG
                              601                                                650
CDS2-AT1G56520.2     (601)   PENLVTLNMEYSELEKLWKGTQPLANLKEMNLCGSSCLKELPDLSKAANL
    HCP6-protein     (601)   PENLVTLNMEYSELEKLWKGTQPLANLKEMNLCGSSCLKELPDLSKAANL
HCP6_opt protein     (601)   PENLVTLNMEYSELEKLWKGTQPLANLKEMNLCGSSCLKELPDLSKAANL
                              651                                                700
CDS2-AT1G56520.2     (651)   ERLDVAECNALVEIPSSVANLHKIVNLHMESCESLEVIPTLINLASLKII
    HCP6-protein     (651)   ERLDVAECNALVEIPSSVANLHKIVNLHMESCESLEVIPTLINLASLKII
HCP6_opt protein     (651)   ERLDVAECNALVEIPSSVANLHKIVNLHMESCESLEVIPTLINLASLKII
                              701                                                750
CDS2-AT1G56520.2     (701)   NIHDCPRLKSFPDVPTSLEELVIEKTGVQELPASFRHCTGVTTLYICSNR
    HCP6-protein     (701)   NIHDCPRLKSFPDVPTSLEELVIEKTGVQELPASFRHCTGVTTLYICSNR
HCP6_opt protein     (701)   NIHDCPRLKSFPDVPTSLEELVIEKTGVQELPASFRHCTGVTTLYICSNR
```

Figure 4 continued:

```
                          751                                              800
CDS2-AT1G56520.2  (751)   NLKTFSTHLPMGLRKLDLSNCGIEWVTDSIKDLHNLYYLKLSGCKRLVSL
    HCP6-protein  (751)   NLKTFSTHLPMGLRKLDLSNCGIEWVTDSIKDLHNLYYLKLSGCKRLVSL
 HCP6_opt protein (751)   NLKTFSTHLPMGLRKLDLSNCGIEWVTDSIKDLHNLYYLKLSGCKRLVSL
                          801                                              850
CDS2-AT1G56520.2  (801)   PELPCSLECLFAEDCTSLERVSDSLNIPNAQFNFIKCFTLDREARRAIIQ
    HCP6-protein  (801)   PELPCSLECLFAEDCTSLERVSDSLNIPNAQFNFIKCFTLDREARRAIIQ
 HCP6_opt protein (801)   PELPCSLECLFAEDCTSLERVSDSLNIPNAQFNFIKCFTLDREARRAIIQ
                          851                                              900
CDS2-AT1G56520.2  (851)   QSFVHGNVILPAREVLEEVDYRARGNCLTIPPSAFNRFKVCVVDVIGDSV
    HCP6-protein  (851)   QSFVHGNVILPAREVLEEVDYRARGNCLTIPPSAFNRFKVCVVSIS---
 HCP6_opt protein (851)   QSFVHGNVILPAREVLEEVDYRARGNCLTIPPSAFNRFKVCVVSIS---
                          901                                              950
CDS2-AT1G56520.2  (901)   KSASEDFQLQTVYTFQTEHVFIFDISFPLIFNGRKIMLKFFGGYARIIEC
    HCP6-protein  (898)   --------------------------------------------------
 HCP6_opt protein (898)   --------------------------------------------------
                          951                                             1000
CDS2-AT1G56520.2  (951)   GVQILMDETDGSNKGLFENVEWRTYKSYEEAVEKEEYQWDTNQSEEEEED
    HCP6-protein  (898)   --------------------------------------------------
 HCP6_opt protein (898)   --------------------------------------------------
                         1001                                             1050
CDS2-AT1G56520.2 (1001)   DLWDTHESNEAFDKEDHDYESAPTAYEDICLNPSPKLDPIPNPTASSSRP
    HCP6-protein  (898)   --------------------------------------------------
 HCP6_opt protein (898)   --------------------------------------------------
                         1051                                             1100
CDS2-AT1G56520.2 (1051)   LSRFTFPDSAAAFATPRIDDEASNKDDNEEGDKSEIVSEDKDEDTAHDGD
    HCP6-protein  (898)   --------------------------------------------------
 HCP6_opt protein (898)   --------------------------------------------------
                         1101       1118
CDS2-AT1G56520.2 (1101)   YQSISSKLLHMLSLCVN-
    HCP6-protein  (898)   ------------------
 HCP6_opt protein (898)   ------------------
```

Figure 5:

```
   1 ATGGCTTCTT CTTCTTCCTC ACCTCGCAAC TGGAGATACA ATGTCTTCAC
  51 GAGCTTCCAT GGACCAGACG TCCGTATTAA ATTTCTCAGT CATTTACGTC
 101 AACAGTTTAT TTACAATGGA ATTACTATGT TCGATGACAA CGGGATCGAA
 151 AGAAGCCAAA TTATCGCTCC AGCTCTCAAA AAAGCCATTG GAGAATCGAG
 201 GATCGCGATC TTATTGCTCT CGAAGAACTA TGCTTCTTCC AGTTGGTCTT
 251 TGGATGAGCT ATTGGAGATT TTAAAGTGCA AAGAAGATAT AGGGCAAATA
 301 GTGATGACTG TCTTCTACGA AGTTGATCCT TCTGATGTCC GCAACCAAAC
 351 CGGAGATTTT GGGATTGCTT TTAAAGAAAC TTGTGCTCAT AAAACAGAGG
 401 AGGAGAGGCA AAAATGGACC CAAGCTTTGA CCTATGTGGG CAACATTGCC
 451 GGAGAAGACT TTAAACACTG GCCCAATGAA GCTAAAATGA TCGAGAAGAT
 501 TGCAAGAGAT GTTTCAGATA TACTAAACGT CACACCGTGT AGGGATTTTG
 551 ATGGCATGGT TGGACTAAAC GATCATTTGA GGGAAATGGA GTCTTTGCTA
 601 GATTTAAAGA ATGATGGAGT TAAGATTGTT GGAATCTCTG GTCCTGCAGG
 651 CATTGGTAAA AGTACCATTG CTACAGCTTT ACATGGTCGA CTCTCTAACA
 701 TGTTTCAGCG TACTTGTTTT GTGGACAATC TTAGGGAAAG CTATAAGATT
 751 GGTCTTGATG AGTATCGTTT GAAGTTGCAC TTACAACAGC AACTTCTTGC
 801 ATATGTTTTA AATCAGGATA AAATTAGGGT GGGCCATTTA AGTGTGATGA
 851 AAGAAAGGCT TGACGACTTG AGGGTTCTTA TTATTCTTGA TGATGTGGAG
 901 CATCTATATC AACTAGAGGC TTTGGCTGAT ATCAGGTGGT TTGGTCCTGG
 951 AAGTAGGGTG ATAGTGACCA CTGAAAACAG AGAGATTTTG CTGCAACATG
1001 GTATCAAGGA TATATACCAT GTGGGTTTTC CATCAGAAGG AGAAGCTCTA
1051 ATGATCTTTT GTCTATCTGC TTTTAGACAA CCCTCTCCAC CTTATGGTTT
1101 TTTGAAGCTT ACATATGAAG TTGCAAGTAT TTGTGGTAAT CTTCCATTGG
1151 GTCTGCATGT TTTGGGGACG TTATTGTGGG AAAAAGTCA GGCTGACTGG
1201 ATTGAAGAAC TACCAAGGTT GAAAGACTGT CTTGATGGAA GAATTGAGAG
1251 TGTATTGAAA GTTGGCTATG AGAGTTTATA TGAGAAAGAC CAAGCTCTTT
1301 TTCTCCTCAT TGCAGTCTAC TTCAATTATG ATTATGTTGA TTATGTGACA
1351 TCCATGCTAG AAAATACTAA CGTATTGGAT GTTAGACTTG GGTTGAAAAA
1401 ACTAGCTAAT AGATGTCTTA TACAAATAGA TATAGACCAT AATCGCAAAA
1451 GTAGAGTCGT AATGAACCGG TTGCTACAAG TAATGGCTCG AGAAGTTATT
1501 TCCAAACAAA AAATTTCCAA ACGAAAGATT CTAGAAGATC CCCAGGATAT
1551 TTGTTATGTT CTAGAAGAGG CAAAGGGTAA AGGATCAGCT TTAGGATTAT
1601 CATTGGACGT AGCAGAGATC AAAGAATTAG TAATAAACAA AAAGGCTTTT
1651 AAAAAAATGT GCAATCTTCT CATCTTAAAA GTCTTTAATG GGACGGATCC
1701 CCGAGATAGT AAATTGCACG TACCAGAGGA GATGGAGCTT CCATCTAGCA
1751 TAAGGTTACT ACATTGGAG GCATACCCGA GAAAATCTTT TAGATTTGGT
1801 CCAGAAAATC TCGTCACACT CAACATGGAG TACAGTGAGC TCGAGAAGCT
1851 ATGGAAAGGA ACTCAGCCAC TTGCAAATCT CAAGGAGATG AACTTGTGTG
1901 GGTCATCTTG TTTGAAGGAA CTCCCAGATC TTTCGAAAGC AGCAAATCTG
1951 GAGAGATTGG ATGTGGCTGA GTGCAATGCT TTGGTAGAGA TTCCATCCTC
2001 AGTTGCGAAT CTTCACAAAA TAGTTAACTT ACACATGGAA TCCTGTGAAA
2051 GTCTAGAAGT CATTCCAACT CTCATCAACT TGGCATCTCT TAAGATTATC
2101 AACATACATG ATTGCCCACG GTTGAAAAGT TTTCCAGATG TTCCCACCAG
2151 CCTCGAGGAA CTTGTGATAG AGAAACAGG GGTACAAGAA TTGCCTGCAT
2201 CATTTAGGCA TTGCACTGGT GTTACTACTC TTTATATATG TTCCAATAGA
2251 AATCTCAAGA CCTTCTCAAC ACATCTCCCC ATGGGTCTAA GGAAGCTAGA
2301 CCTAAGCAAT GTGGTATTG AGTGGGTTAC AGATAGCATC AAAGATCTTC
2351 ATAATCTATA TTACCTTAAA CTATCAGGCT GCAAAAGACT TGTGTCTTTG
2401 CCAGAACTCC CTTGTTCGCT CGAGTGTCTA TTTGCAGAGG ATTGTACATC
2451 ACTAGAAAGA GTAAGTGACT CTCTAAACAT TCCAAATGCG CAGTTCAATT
2501 TCATCAAATG CTTCACATTG GATAGAGAAG CACGACGAGC GATTATTCAA
2551 CAATCGTTTG TTCATGGGAA TGTTATCTTA CCAGCAAGAG AAGTACTTGA
2601 AGAAGTCGAT TACCGAGCGA GAGGAAATTG CTTAACAATT CCTCCTTCTG
2651 CTTTCAACAG ATTTAAGGTT TGCGTTGTGT TGTCAATTCA CTAG
```

Figure 6:

```
MASSSSSPRNWRYNVFTSFHGPDVRIKFLSHLRQQFIYNGITMFDDNGIE 50
RSQIIAPALKKAIGESRIAILLLSKNYASSSWSLDELLEILKCKEDIGQI 100
VMTVFYEVDPSDVRNQTGDFGIAFKETCAHKTEEERQKWTQALTYVGNIA 150
GEDFKHWPNEAKMIEKIARDVSDILNVTPCRDFDGMVGLNDHLREMESLL 200
DLKNDGVKIVGISGPAGIGKSTIATALHGRLSNMFQRTCFVDNLRESYKI 250
GLDEYRLKLHLQQQLLAYVLNQDKIRVGHLSVMKERLDDLRVLIILDDVE 300
HLYQLEALADIRWFGPGSRVIVTTENREILLQHGIKDIYHVGFPSEGEAL 350
MIFCLSAFRQPSPPYGFLKLTYEVASICGNLPLGLHVLGTLLWGKSQADW 400
IEELPRLKDCLDGRIESVLKVGYESLYEKDQALFLLIAVYFNYDYVDYVT 450
SMLENTNVLDVRLGLKKLANRCLIQIDIDHNRKSRVVMNRLLQVMAREVI 500
SKQKISKRKILEDPQDICYVLEEAKGKGSALGLSLDVAEIKELVINKKAF 550
KKMCNLLILKVFNGTDPRDSKLHVPEEMELPSSIRLLHWEAYPRKSFRFG 600
PENLVTLNMEYSELEKLWKGTQPLANLKEMNLCGSSCLKELPDLSKAANL 650
ERLDVAECNALVEIPSSVANLHKIVNLHMESCESLEVIPTLINLASLKII 700
NIHDCPRLKSFPDVPTSLEELVIEKTGVQELPASFRHCTGVTTLYICSNR 750
NLKTFSTHLPMGLRKLDLSNCGIEWVTDSIKDLHNLYYLKLSGCKRLVSL 800
PELPCSLECLFAEDCTSLERVSDSLNIPNAQFNFIKCFTLDREARRAIIQ 850
QSFVHGNVILPAREVLEEVDYRARGNCLTIPPSAFNRFKVCVVLSIH*
```

Figure 7:

```
   1 ATGGCTAGCT CTAGCTCTAG TCCTAGGAAC TGGCGTTATA ACGTGTTCAC
  51 TAGCTTTCAC GGCCCCGACG TTAGGATTAA GTTCCTTAGT CACCTTAGGC
 101 AGCAGTTTAT CTATAACGGG ATCACTATGT TCGACGATAA CGGGATCGAG
 151 CGTAGTCAGA TTATCGCTCC AGCTCTTAAG AAGGCTATCG GCGAGTCTAG
 201 GATCGCTATC CTGCTCCTTA GTAAGAACTA CGCTAGCTCT AGTTGGTCAC
 251 TCGACGAGCT TCTCGAGATC CTTAAGTGTA AAGAGGATAT CGGTCAGATC
 301 GTGATGACCG TGTTCTACGA GGTTGACCCT AGCGACGTTA GGAATCAGAC
 351 TGGCGATTTC GGGATCGCCT TTAAAGAGAC TTGCGCTCAC AAGACCGAAG
 401 AGGAACGTCA AAAGTGGACT CAGGCTCTTA CCTACGTGGG TAATATTGCC
 451 GGCGAGGACT TTAAGCACTG GCCTAACGAA GCTAAGATGA TCGAGAAGAT
 501 CGCTAGGGAC GTTAGCGATA TCCTTAACGT GACCCCTTGT AGGGACTTCG
 551 ACGGAATGGT TGGACTTAAC GATCACCTTA GAGAGATGGA ATCACTCCTC
 601 GACCTTAAGA ACGACGGCGT TAAGATCGTG GGAATTAGTG GACCAGCTGG
 651 GATCGGTAAG TCTACTATTG CTACTGCACT TCACGGTAGG CTTAGTAATA
 701 TGTTTCAGAG GACCTGCTTC GTGGATAACC TTAGAGAGTC CTATAAGATC
 751 GGCCTCGACG AGTATAGGCT TAAGCTTCAC CTTCAGCAGC AGCTCTTGGC
 801 CTACGTGCTT AATCAGGATA AGATTAGAGT GGGTCACCTT AGCGTGATGA
 851 AGGAAAGGCT CGACGATCTT AGGGTGCTGA TTATTCTCGA CGACGTTGAG
 901 CACCTCTATC AGCTTGAAGC TCTCGCCGAT ATTAGGTGGT TCGGACCAGG
 951 ATCTAGGGTG ATCGTGACTA CCGAGAATAG GGAAATCCTC CTTCAGCACG
1001 GGATTAAGGA TATCTATCAC GTGGGCTTCC CTAGCGAAGG TGAGGCTCTT
1051 ATGATCTTCT GCCTTAGCGC TTTTAGGCAG CCTAGTCCAC CTTACGGATT
1101 CCTTAAGCTC ACCTACGAAG TGGCTAGTAT CTGCGGTAAC CTTCCACTTG
1151 GACTTCACGT GTTGGGAACC CTTTTGTGGG GTAAGAGTCA GGCTGATTGG
1201 ATCGAGGAAC TCCCTAGGCT TAAGGATTGC CTCGACGGTA GGATTGAGTC
1251 AGTTCTTAAG GTGGGCTACG AGTCACTCTA CGAGAAGGAT CAGGCTCTCT
1301 TCCTCCTTAT CGCCGTTTAC TTTAACTACG ACTACGTTGA CTACGTGACC
1351 TCTATGCTCG AGAACACTAA CGTGCTCGAC GTTAGGCTCG GCCTTAAGAA
1401 GCTTGCTAAC CGTTGCCTGA TTCAGATTGA TATCGATCAC AACCGTAAGT
1451 CTAGGGTGGT GATGAATAGG CTCCTTCAGG TGATGGCTAG GGAAGTGATT
1501 AGTAAGCAGA AGATTAGTAA GCGTAAGATC CTCGAGGACC CTCAGGATAT
1551 TTGCTACGTG TTGGAAGAGG CTAAGGGTAA GGGATCAGCT CTCGGACTTA
1601 GTCTTGACGT GGCCGAGATT AAGGAACTCG TGATTAACAA GAAAGCCTTT
1651 AAGAAGATGT GTAACCTCCT GATCCTTAAA GTGTTTAACG GCACCGACCC
```

Figure 7 continued:

```
1701 TAGGGACTCT AAGCTTCACG TTCCAGAAGA GATGGAACTG CCTAGCTCTA
1751 TTAGGCTGCT TCACTGGGAG GCTTACCCTA GGAAGTCTTT TAGATTCGGC
1801 CCAGAGAACC TCGTGACCCT TAATATGGAA TACTCAGAGC TTGAGAAGCT
1851 CTGGAAGGGA ACTCAGCCAC TCGCTAACCT TAAAGAGATG AACCTCTGCG
1901 GCTCTAGCTG CCTTAAAGAG CTTCCAGATC TTAGTAAGGC CGCTAACCTT
1951 GAGAGGCTTG ACGTTGCAGA GTGTAACGCT CTCGTTGAGA TCCCTAGCTC
2001 AGTGGCTAAC CTTCACAAGA TCGTTAACCT TCACATGGAA TCCTGCGAGT
2051 CACTCGAGGT TATCCCTACC CTTATTAACC TCGCTAGCCT TAAGATTATT
2101 AACATTCACG ACTGCCCTAG ACTTAAGTCC TTCCCAGATG TGCCTACTAG
2151 CCTTGAGGAA CTGGTGATTG AAAAGACCGG CGTTCAAGAG CTGCCCGCTA
2201 GTTTTAGACA CTGTACCGGT GTGACTACCC TCTATATCTG CTCTAACCGT
2251 AACCTTAAGA CCTTTAGCAC TCACCTCCCT ATGGGCCTTA GGAAGCTCGA
2301 TCTTAGTAAC TGCGGAATCG AGTGGGTGAC CGACTCTATT AAGGACCTTC
2351 ACAACCTCTA CTACCTTAAG CTTAGCGGCT GTAAGAGGCT CGTTAGCCTT
2401 CCAGAACTTC CTTGCTCACT TGAGTGCCTC TTCGCTGAGG ATTGCACTAG
2451 TCTTGAGCGT GTTAGCGACT CACTTAATAT CCCTAACGCT CAGTTTAACT
2501 TTATTAAGTG CTTCACCCTC GATAGGGAAG CTAGGCGTGC TATTATTCAG
2551 CAGTCCTTCG TTCACGGTAA CGTGATCCTT CCAGCTAGAG AGGTGCTCGA
2601 AGAGGTTGAC TATAGAGCTA GGGGAAACTG CCTCACTATC CCCCCTAGTG
2651 CCTTTAATAG GTTTAAGGTG TGCGTGGTGC TCTCAATCCA TTAA
```

Figure 8:

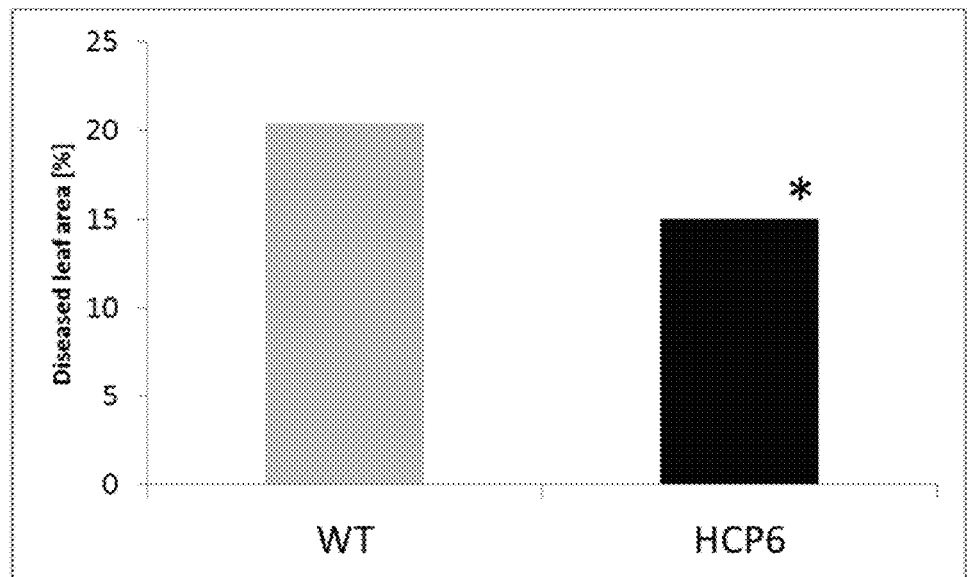

Figure 9:

| SEQ ID NO: | Description of the sequence listing |
|---|---|
| 1 | Nucleotide sequence HCP6 splice variant 1 (corresponds to accession number AT1G56520.1, NM_104528); Arabidopsis thaliana |
| 2 | Amino acid sequence from HCP6 splice variant 1, AT1G56520.1; Arabidopsis thaliana |
| 3 | Nucleotide sequence HCP6 splice variant 2, AT1G56520.2; accession No 6530298775; Arabidopsis thaliana |
| 4 | Amino acid sequence from HCP6 splice variant 2, AT1G56520.2; Arabidopsis thaliana |
| 5 | Nucleotide sequence of the HCP6 genomic sequence around the region which codes for HCP6 (TAIR accession number 6530301567), Arabidopsis thaliana |
| 6 | Nucleotide sequence HCP6 splice variant 1, codon optimized; Arabidopsis thaliana |
| 7 | Nucleotide sequence HCP6 splice variant 2, codon optimized; Arabidopsis thaliana |
| 8 | HCP6 forward primer |
| 9 | HCP6 reverse primer |
| 10 | HCP6 forward primer (ATG-attB1) |
| 11 | HCP6 reverse primer (stop-attB2) |
| 12 | Nucleotide sequence HCP6, variant 1 |
| 13 | Amino acid sequence HCP6, variant 1 |
| 14 | Nucleotide sequence HCP6, variant 2 |
| 15 | Amino acid sequence HCP6, variant 2 |
| 16 | Nucleotide sequence HCP6, variant 3 |
| 17 | Amino acid sequence HCP6, variant 3 |
| 18 | Nucleotide sequence HCP6, variant 4 |
| 19 | Amino acid sequence HCP6, variant 4 |
| 20 | Nucleotide sequence HCP6, variant 5 |
| 21 | Amino acid sequence HCP6, variant 5 |
| 22 | Nucleotide sequence HCP6, variant 6 |
| 23 | Amino acid sequence HCP6, variant 6 |
| 24 | Nucleotide sequence HCP6, variant 7 |
| 25 | Amino acid sequence HCP6, variant 7 |
| 26 | Nucleotide sequence HCP6, variant 8 |
| 27 | Amino acid sequence HCP6, variant 8 |
| 28 | Nucleotide sequence HCP6, variant 9 |
| 29 | Nucleotide sequence HCP6, variant 10 |

Figure 9 continued:

| 30 | Nucleotide sequence HCP6, variant 11 |
|----|--------------------------------------|
| 31 | Nucleotide sequence HCP6, variant 12 |
| 32 | Nucleotide sequence HCP6, variant 13 |
| 33 | Nucleotide sequence HCP6, variant 14 |
| 34 | Nucleotide sequence HCP6, variant 15 |
| 35 | Nucleotide sequence HCP6, variant 16 |

FUNGAL RESISTANT PLANTS EXPRESSING HCP6

This application is a National Stage application of International Application No. PCT/EP2014/050397, filed Jan. 10, 2014, which claims priority under 35 U.S.C. § 119 to European Patent Application No. 13152971.1, filed Jan. 29, 2013, the entire contents of which are incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "74752_371_SeqListing.txt" created on Jul. 8, 2015, and is 160,389 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the family Phacopsoraceae, for example soybean rust, in plants, plant parts, and/or plant cells. This is achieved by increasing the expression and/or activity of an HCP6 protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the family Phacopsoraceae, for example soybean rust, and to recombinant expression vectors comprising a sequence that is identical or homologous to a sequence encoding an HCP6 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects).

Another more specific resistance mechanism is based on the presence of so called resistance genes (R-genes). Most R genes belong to the nucleotide-binding site-leucine-rich repeat (NBS-LRR) gene family and function in monitoring the presence of pathogen effector proteins (virulence factors; avirulence factors). After recognizing the pathogen derived proteins a strong defense reaction (mostly accompanied by a programmed cell death) is elicited.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora* The necrotrophic phytopathogenic fungi depend for their nutrition on dead cells of the plants, e.g. species from the genus *Fusarium, Rhizoctonia* or Mycospaerella Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races. Therefore there is a strong need to discover R-genes that are derived from non-hosts plants (e.g. *Arabidopsis*) as they are thought to be more durable.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust.

Surprisingly, we found that fungal pathogens, in particular of the family Phacopsoraceae, for example soybean rust, can be controlled by increasing the expression of an HCP6 protein.

The present invention therefore provides a method of increasing resistance against fungal pathogens, preferably against rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust, in transgenic plants, transgenic plant parts, or transgenic plant cells by overexpressing one or more HCP6 nucleic acids.

A further object is to provide transgenic plants resistant against fungal pathogens, preferably rust pathogens (i.e., fungal pathogens of the order Pucciniales), preferably of the family Phacopsoraceae, more preferably against fungal pathogens of the genus *Phacopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous HCP6 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust.

Surprisingly, we found that resistance against fungal pathogens, in particular of the family Phacopsoraceae, for example soybean rust, can be enhanced by increasing the expression of a HCP6 protein.

The present invention therefore provides a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust, in transgenic plants, transgenic plant parts, or transgenic plant cells by overexpressing one or more HCP6 nucleic acids.

A further object is to provide transgenic plants resistant against fungal pathogens, preferably rust pathogens (i.e., fungal pathogens of the order Pucciniales), preferably of the family Phacopsoraceae, more preferably against fungal pathogens of the genus *Phacopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous HCP6 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

FIG. 2 shows the schematic illustration of the plant transformation vector harboring the HCP6 cDNA under control of the parsley ubiquitine promoter.

FIG. 3 shows the alignment of the *Arabidopsis* genome sequence (TAIR accession No 6530301567, AT1G56520, SEQ ID NO: 5), the putative cDNAs (derived from the genomic sequence; HCP6: accession No. NM_104528, AT1G56520.1, SEQ ID NO: 1; CDS2: TAIR accession No 6530298775, AT1G56520.2, SEQ ID NO: 3), and the optimized sequence of the HCP6 (HCP6_opt) that is codon optimized for optimal expression in soybean (SEQ ID NO: 6).

FIG. 4 shows the alignment of the *Arabidopsis* HCP6 protein (SEQ ID NO: 2), the HCP6_opt protein, encoded by the codon optimized HCP6 sequence (SEQ ID NO: 6), which is identical to HCP6 protein (SEQ ID NO: 2) and the second predicted protein (CDS2: protein accession No F4I552, AT1G56520.2, SEQ ID NO: 4) based on bioinformatics analysis of the genomic sequence of At1g56520 (SEQ ID NO: 5).

FIG. 5 shows the full-length-sequence of the HCP6 gene from *Arabidopsis thaliana* having SEQ ID NO: 1.

FIG. 6 shows the sequence of the HCP6 protein (SEQ ID NO: 2).

FIG. 7 shows the sequence of the optimized HCP6 gene, which is codon optimized for optimal expression in soybean (*Glycine max*) having SEQ ID NO: 6.

FIG. 8 shows the result of the scoring of 44 transgenic soy plants (derived from 5 independent events, 7-10 plants per event) expressing the HCP6 overexpression vector construct. $T_1$ soybean plants expressing HCP6 protein were inoculated with spores of *Phakopsora pachyrhizi* The evaluation of the diseased leaf area on all leaves was performed 14 days after inoculation. The average of the percentage of the leaf area showing fungal colonies or strong yellowing/browning on all leaves was considered as diseased leaf area. At all 44 soybean $T_1$ plants expressing HCP6 (expression checked by RT-PCR) were evaluated in parallel to non-transgenic control plants. The average of the diseased leaf area is shown in FIG. 8. Overexpression of HCP6 significantly (* : $p<0.05$) reduces the diseased leaf area in comparison to non-transgenic control plants by 26.1%.

FIG. 9 contains a brief description of the sequences of the sequence listing.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc. (1998 Supplement).

It is to be understood that as used in the specification and in the claims, “a” or “an” can mean one or more, depending upon the context in which it is used. Thus, for example, reference to “a cell” can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

“Homologues” of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar functional activity as the unmodified protein coded by the unmodified nucleic acid from which they are derived. In particular, homologues of a nucleic acid may encompass substitutions on the basis of the degenerative amino acid code.

The terms "identity", "homology" and "similarity" are used herein interchangeably. "Identity" or "homology" or "similarity" between two nucleic acids sequences or amino acid sequences refers in each case over the entire length of the respective HCP6 nucleic acid sequence or HCP6 amino acid sequence.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the SmithWaterman algorithm is particularly useful (Smith T F, Waterman M S (1981) J. Mol. Biol 147(1); 195-7).

The sequence identity may also be calculated by means of the Vector NTI Suite 7.1 program of the company Informax (USA) employing the Clustal Method (Higgins D G, Sharp PM. Fast and sensitive multiple sequence alignments on a microcomputer. Comput Appl. Biosci. 1989 April; 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

Sequence identity between the nucleic acid or protein useful according to the present invention and the HCP6 nucleic acids or HCP6 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Taylor W. R. (1986) The classification of amino acid conservation J Theor Biol., 119:205-18 and Table 1 below).

TABLE 1

Examples of conserved amino acid substitutions

| Residue | Conservative Substitutions |
|---|---|
| A | G, V, I, L, M |
| C | S, T |
| E | D |
| D | E |
| G | A, V, I, L, M |
| F | Y, W |
| I | V, A, G, L, M |
| H | R, K |
| K | R, H |
| M | L, I, V, A, G |
| L | M, I, V, A, G |
| N | Q |
| Q | N |
| P | |
| S | T, C |
| R | K, H |
| T | S, C |
| W | Y, F |
| V | I, A, G, L, M |
| Y | F, W |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by noncoding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains or motifs may also be identified using routine techniques, such as by sequence alignment.

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phacopsoracea, in particular *Phakopsora pachyrhizi* and *Phakopsora meibomiae*—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous HCP6 nucleic acid, functional fragments thereof and/or an exogenous nucleic acid capable of hybridizing with an HCP6 nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens Phakopsora *pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole HCP6 nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous HCP6 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous HCP6 nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more HCP6 nucleic acids, all those constructions brought about by man by genetechnological methods in which either (a) the sequences of the HCP6 nucleic acids or a part thereof, or (b) genetic control sequence(s) which is operably linked with the HCP6 nucleic acid sequence according to the invention, for example a promoter, or (c) a) and b)

are not located in their natural genetic environment or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

For instance, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

For instance, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous HCP6 nucleic acid, recombinant construct, vector or expression cassette including one or more HCP6 nucleic acids is integrated into the genome by means of genetechnology.

A "wild type" plant, "wild type" plant part, or "wild type" plant cell means that said plant, plant part, or plant cell does not express exogenous HCP6 nucleic acid or exogenous HCP6 protein.

Natural locus means the location on a specific chromosome, preferably the location between certain genes, more preferably the same sequence background as in the original plant which is transformed.

Preferably, the transgenic plant, plant cell or tissue thereof expresses the HCP6 nucleic acids, HCP6 constructs or HCP6 expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the HCP6 nucleic acids has an identity as defined above over a length of at least 20%, at least 30%, at least 50%, at least 75%, at least 90% of the nucleotides of the respective HCP6 nucleic acid.

The term "splice variant" as used herein encompasses variants of a nucleic acid sequence in which selected introns and/or exons have been excised, replaced, displaced or added, or in which introns have been shortened or lengthened. Thus, a splice variant can have one or more or even all introns removed or added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the HCP6 nucleotide sequence as defined by SEQ ID NO: 1 or 6.

The term "increased activity" or "enhanced activity" as used herein means any protein having increased activity and which provides an increased fungal resistance compared with the wildtype plant merely expressing the respective endogenous HCP6 nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

HCP6 Nucleic Acids

The HCP6 nucleic acid to be overexpressed in order to achieve increased resistance to fungal pathogens, e.g., of the family Phacopsoraceae, for example soybean rust, is preferably a nucleic acid coding for an HCP6 protein, and is preferably as defined by SEQ ID NO: 6, 1, 3, 5, 7, 12, 14, 16, 18, 20, 22, 24, 26, 28, 29, 30, 31, 32, 33, 34, or 35, or a fragment, homolog, derivative, orthologue or paralogue thereof, or a splice variant thereof. Preferably, the nucleic acid coding for an HCP6 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35, or is a functional fragment thereof, or a splice variant thereof. Most preferred is at least 90% identity, at least 92%, at least 95%, at least 97% identity, more preferred is at least 98% or at least 99% identity with SEQ ID NO: 6, 1, 3, 5, 7, 12, 14, 16, 18, 20, 22, 24, 26, 28, 29, 30, 31, 32, 33, 34, or 35.

Preferably, the HCP6 nucleic acid to be overexpressed in order to achieve increased resistance to fungal pathogens, e.g., of the family Phacopsoraceae, for example soybean rust, is preferably a nucleic acid coding for an HCP6 protein, and is preferably as defined by SEQ ID NO: 6, or a fragment, homolog, derivative, orthologue or paralogue thereof, or a splice variant thereof. Preferably, the nucleic acid coding for an HCP6 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 6 or is a functional fragment thereof, or a splice variant thereof. Most preferred is at least 90% identity, at least 92%, at least 95%, at least 97% identity, more preferred is at least 98% or at least 99% identity with SEQ ID NO: 6.

More preferably, the HCP6 nucleic acid to be overexpressed in order to achieve increased resistance to fungal pathogens, e.g., of the family Phacopsoraceae, for example soybean rust, is preferably a nucleic acid coding for an HCP6 protein, and is preferably as defined by SEQ ID NO: 1, or a fragment, homolog, derivative, orthologue or paralogue thereof, or a splice variant thereof. Preferably, the nucleic acid coding for an HCP6 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 1 or is a functional fragment thereof, or a splice variant thereof. Most preferred is at least 92%, at least 95%, at least 97% identity, more preferred is at least 98% or at least 99% identity with SEQ ID NO: 1.

SEQ ID NO: 6 corresponds to SEQ ID NO: 1, wherein the codon usage has been optimized for expression in soy.

SEQ ID NO: 7 corresponds to SEQ ID NO: 3, wherein the codon usage has been optimized for expression in soy.

Preferably the HCP6 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 6, 1, 3, 5, 7, 12, 14, 16, 18, 20, 22, 24, 26, 28, 29, 30, 31, 32, 33, 34, or 35, or a functional fragment, derivative, orthologue, or paralogue thereof, or a splice variant thereof, wherein overexpression of the sequence confers enhanced fungal resistance in the plant relative to a control plant;

(ii) a nucleic acid encoding a HCP6 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 4, 13, 15, 17, 19, 21, 23, 25, or 27 or a functional fragment, derivative, orthologue, or paralogue thereof, wherein overexpression of the sequence confers enhanced fungal resistance in the plant relative to a control plant; preferably the HCP6 protein has essentially the same biological activity as an HCP6 protein encoded by SEQ ID NO: 6, 1, 3, 5, or 7; preferably the HCP6 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and (iv) a nucleic acid encoding the same HCP6 protein as the HCP6 nucleic acids of (i) to (iii) above, but differing from the HCP6 nucleic acids of (i) to (iii) above due to the degeneracy of the genetic code.

Preferably the HCP6 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof;

(ii) a nucleic acid encoding a HCP6 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the HCP6 protein has essentially the same biological activity as an HCP6 protein encoded by SEQ ID NO: 1, preferably the HCP6 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same HCP6 protein as the HCP6 nucleic acids of (i) to (iii) above, but differing from the HCP6 nucleic acids of (i) to (iii) above due to the degeneracy of the genetic code.

Preferably the HCP6 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 6, or a functional fragment, derivative, orthologue, or paralogue thereof, or a splice variant thereof, wherein overexpression of the sequence confers enhanced fungal resistance in the plant relative to a control plant;

(ii) a nucleic acid encoding a HCP6 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof, wherein overexpression of the sequence confers enhanced fungal resistance in the plant relative to a control plant; preferably the HCP6 protein has essentially the same biological activity as an HCP6 protein encoded by SEQ ID NO: 6, preferably the HCP6 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and (iv) a nucleic acid encoding the same HCP6 protein as the HCP6 nucleic acids of (i) to (iii) above, but differing from the HCP6 nucleic acids of (i) to (iii) above due to the degeneracy of the genetic code.

Preferably the HCP6 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3 or 7, or a functional fragment, derivative, orthologue, or paralogue thereof, or a splice variant thereof;

(ii) a nucleic acid encoding a HCP6 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 4, or a functional fragment, derivative, orthologue, or paralogue thereof; preferably the HCP6 protein has essentially the same biological activity as an HCP6 protein encoded by SEQ ID NO: 3 or 7, preferably the HCP6 protein confers enhanced fungal resistance relative to control plants; (iii) a nucleic acid molecule which hybridizes with a complementary sequence of any of the nucleic acid molecules of (i) or (ii) under high stringency hybridization conditions; preferably encoding a HCP6 protein; preferably wherein the nucleic acid molecule codes for a polypeptide which has essentially identical properties to the polypeptide described in SEQ ID NO: 4; preferably the encoded protein confers enhanced fungal resistance relative to control plants; and (iv) a nucleic acid encoding the same HCP6 protein as the HCP6 nucleic acids of (i) to (iii) above, but differing from the HCP6 nucleic acids of (i) to (iii) above due to the degeneracy of the genetic code.

Percentages of identity of a nucleic acid are indicated with reference to the entire nucleotide region given in a sequence specifically disclosed herein.

Preferably the portion of the HCP6 nucleic acid is about 1000-1500, about 1500-2000, about 2000-2500, about 2500-3000, about 3000-3500, about 3500-4000, or about 4000-4311 nucleotides, preferably consecutive nucleotides, preferably counted from the 5' or 3' end of the nucleic acid, in length, of the nucleic acid sequences given in SEQ ID NO: 6, 1, 3, 5, 7, 12, 14, 16, 18, 20, 22, 24, 26, 28, 29, 30, 31, 32, 33, 34, or 35.

Preferably, the HCP6 nucleic acid comprises at least about 1000, at least about 1500, at least about 2000, at least about 2500, at least about 2750, at least about 3000, at least about 3250, at least about 3500, at least about 3750, at least about 4000, at least about 4100, at least about 4200, or at least about 4300 nucleotides, preferably continuous nucleotides, preferably counted from the 5' or 3' end of the nucleic acid or up to the full length of the nucleic acid sequence set out in SEQ ID NO: 6, 1, 3, 5, 7, 12, 14, 16, 18, 20, 22, 24, 26, 28, 29, 30, 31, 32, 33, 34, or 35.

Preferably, the HCP6 nucleic acid comprises at least about 1000, at least about 1500, at least about 2000, at least about 2100, at least about 2200, at least about 2300, at least about 2400, at least about 2500, or at least about 2600 nucleotides, preferably continuous nucleotides, preferably counted from the 5' or 3' end of the nucleic acid or up to the full length of the nucleic acid sequence set out in SEQ ID NO: 1.

Preferably the portion of the HCP6 nucleic acid is about 1000-1500, about 1500-2000, about 2000-2100, about 2100-2200, about 2200-2300, about 2300-2400, about 2400-2500, about 2500-2600, or about 2600-2694 nucleotides, preferably consecutive nucleotides, preferably counted from the 5' or 3' end of the nucleic acid, in length, of the nucleic acid sequences given in SEQ ID NO: 1.

Preferably, the HCP6 nucleic acid comprises at least about 1000, at least about 1500, at least about 2000, at least about 2100, at least about 2200, at least about 2300, at least about 2400, at least about 2500, or at least about 2600 nucleotides, preferably continuous nucleotides, preferably counted from the 5' or 3' end of the nucleic acid or up to the full length of the nucleic acid sequence set out in SEQ ID NO: 6.

Preferably the portion of the HCP6 nucleic acid is about 1000-1500, about 1500-2000, about 2000-2100, about 2100-2200, about 2200-2300, about 2300-2400, about 2400-2500, about 2500-2600, or about 2600-2694 nucleotides, preferably consecutive nucleotides, preferably counted from the 5' or 3' end of the nucleic acid, in length, of the nucleic acid sequences given in SEQ ID NO: 6.

Figure 3:
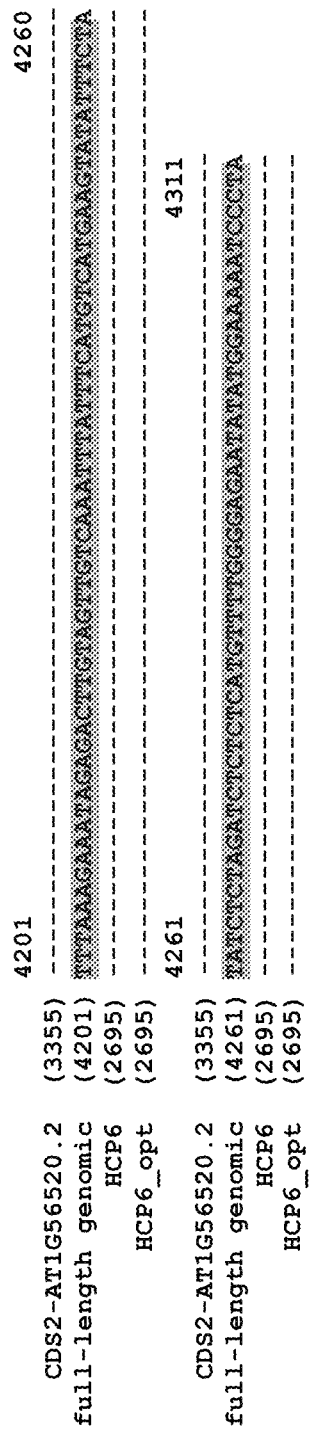

Preferably, the HCP6 nucleic acid is a HCP6 nucleic acid splice variant. Preferred splice variants are splice variants of a nucleic acid represented by SEQ ID NO: 5. Preferred HCP6 nucleic acids being a splice variant of SEQ ID NO: 5 are shown in FIG. 3.

Preferably, the HCP6 nucleic acid is an isolated nucleic acid molecule comprising a splice variant of SEQ ID NO: 5, wherein the splice variant is selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 3, or a functional fragment, derivative, orthologue, or paralogue thereof;
(ii) a nucleic acid encoding a HCP6 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2 or 4, or a functional fragment, derivative, orthologue, or paralogue thereof; preferably the HCP6 protein has essentially the same biological activity as an HCP6 protein encoded by SEQ ID NO: 6, 1, 3, 5, or 7; preferably the HCP6 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and
(iv) a nucleic acid encoding the same HCP6 protein as the HCP6 nucleic acids of (i) to (iii) above, but differing from the HCP6 nucleic acids of (i) to (iii) above due to the degeneracy of the genetic code.

Preferred splice variants of SEQ ID NO: 5 consist of or comprise anyone of the nucleotide sequences shown in SEQ ID NO: 1 or 3. Most preferred is the HCP6 nucleic acid splice variant as shown in SEQ ID NO: 1.

Preferably the HCP6 nucleic acid is an isolated nucleic acid molecule comprising a nucleic acid selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 5, or a splice variant thereof;
(ii) a nucleic acid molecule which hybridizes with a complementary sequence of any of the nucleic acid molecules of (i) under high stringency hybridization conditions; preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and (iii) a nucleic acid encoding the same HCP6 protein as the HCP6 nucleic acids of (i) to (ii) above, but differing from the HCP6 nucleic acids of (i) to (ii) above due to the degeneracy of the genetic code;
wherein the splice variant thereof is selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 3, or a functional fragment, derivative, orthologue, or paralogue thereof;
(ii) a nucleic acid encoding a HCP6 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2 or 4, or a functional fragment, derivative, orthologue, or paralogue thereof; preferably the HCP6 protein has essentially the same biological activity as an HCP6 protein encoded by SEQ ID NO: 6, 1, 3, 5, or 7; preferably the HCP6 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and
(iv) a nucleic acid encoding the same HCP6 protein as the HCP6 nucleic acids of (i) to (iii) above, but differing from the HCP6 nucleic acids of (i) to (iii) above due to the degeneracy of the genetic code.

More preferably the HCP6 nucleic acid is an isolated nucleic acid molecule comprising a nucleic acid selected from the group consisting of:
a nucleic acid having in increasing order of preference least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 5, or a splice variant thereof;
wherein the splice variant thereof is selected from the group consisting of:
a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 3; preferably SEQ ID NO: 1.

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The HCP6 nucleic acids described herein are useful in the constructs, methods, plants, harvestable parts and products of the invention.

HCP6 Proteins

The HCP6 protein is preferably defined by SEQ ID NO: 2, 4, 13, 15, 17, 19, 21, 23, 25, or 27, or a fragment, homolog, derivative, orthologue or paralogue thereof. Preferably, the HCP6 protein of the present invention is encoded by a nucleic acid, which has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35, or a functional fragment thereof. More preferably, the HCP6 protein of the present invention has at least 60%, preferably at least 70% sequence identity, at least 80%, at least 90%, at least 92%, at least 95%, at least 97%, at least 98%, at least 99% sequence identity, or even 100% sequence identity with SEQ ID NO: 2, 4, 13, 15, 17, 19, 21, 23, 25, or 27, or is a functional fragment thereof, an orthologue or a paralogue thereof. Most preferred is at least 90% identity, at least 92%, at least 95%, at least 97% identity, more preferred is at least 98% or at least 99% identity with SEQ ID NO: 2, 4, 13, 15, 17, 19, 21, 23, 25, or 27.

More preferably, the HCP6 protein of the present invention has at least 60%, preferably at least 70% sequence identity, at least 80%, at least 90%, at least 92%, at least 95%, at least 97% at least 98%, at least 99% sequence identity, or even 100% sequence identity with SEQ ID NO: 2 or is a functional fragment thereof, an orthologue or a paralogue thereof.

More preferably, the HCP6 protein of the present invention has at least 60%, preferably at least 70% sequence identity, at least 80%, at least 90%, at least 92%, at least 95%, at least 97% at least 98%, at least 99% sequence identity, or even 100% sequence identity with SEQ ID NO: 4, or is a functional fragment thereof, an orthologue or a paralogue thereof.

Preferably, the HCP6 protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 4, 13, 15, 17, 19, 21, 23, 25, or 27, or a functional fragment, derivative, orthologue, or paralogue thereof, wherein overexpression of the sequence confers enhanced fungal resistance in the plant relative to a control plant; preferably the HCP6 protein has essentially the same biological activity as an HCP6 protein encoded by SEQ ID NO: 6, 1, 3, 5, or 7; preferably the HCP6 protein confers enhanced fungal resistance relative to control plants; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 6, 1, 3, 5, 7, 12, 14, 16, 18, 20, 22, 24, 26, 28, 29, 30, 31, 32, 33, 34, or 35, or a functional fragment, derivative, orthologue, or paralogue thereof, or a splice variant thereof, wherein overexpression of the sequence confers enhanced fungal resistance in the plant relative to a control plant; preferably the HCP6 protein confers enhanced fungal resistance relative to control plants.

Preferably, the HCP6 protein is a protein comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the HCP6 protein has essentially the same biological activity as an HCP6 protein encoded by SEQ ID NO: 6 or 1; preferably the HCP6 protein confers enhanced fungal resistance relative to control plants; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 6 or 1, or a functional fragment, derivative, orthologue, or paralogue thereof, or a splice variant thereof; preferably the HCP6 protein confers enhanced fungal resistance relative to control plants.

Preferably, the HCP6 protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 4, or a functional fragment, derivative, orthologue, or paralogue thereof; preferably the HCP6 protein has essentially the same biological activity as an HCP6 protein encoded by SEQ ID NO: 7 or 3; preferably the HCP6 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 7 or 3, or a functional fragment, derivative, orthologue, or paralogue thereof, or a splice variant thereof; preferably the HCP6 protein confers enhanced fungal resistance relative to control plants.

A preferred derivative of a HCP6 protein is a HCP6 protein consisting of or comprising an amino acid sequence selected from the group consisting of:
an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence represented by SEQ ID NO: 2, 4, 13, 15, 17, 19, 21, 23, 25, or 27,
wherein the non-identical amino acid residues are conservative amino acid substitutions, preferably as shown in Table 1, of the corresponding amino acid residue of SEQ ID NO: 2, 4, 13, 15, 17, 19, 21, 23, 25, or 27; preferably the HCP6 protein has essentially the same biological activity as SEQ ID NO: 2, 4, 13, 15, 17, 19, 21, 23, 25, or 27, or as a HCP6 protein encoded by SEQ ID NO: 6, 1, 3, 5, 7, 12, 14, 16, 18, 20, 22, 24, 26, 28, 29, 30, 31, 32, 33, 34, or 35; preferably the HCP6 protein confers enhanced fungal resistance relative to control plants.

Preferably, the HCP6 protein consists of or comprises an amino acid sequence represented by SEQ ID NO: 2, 4, 13, 15, 17, 19, 21, 23, 25, or 27 with one or more conservative amino acid substitutions, preferably as shown in Table 1, of the corresponding amino acid residues of SEQ ID NO: 2, 4, 13, 15, 17, 19, 21, 23, 25, or 27. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 amino acid residues of SEQ ID NO: 2, 4, 13, 15, 17, 19, 21, 23, 25, or 27 are conservative amino acid substitutions, preferably as shown in Table 1, of the corresponding amino acid residue of SEQ ID NO: 2, 4, 13, 15, 17, 19, 21, 23, 25, or 27.

More preferably, the HCP6 protein consists of or comprises an amino acid sequence having at least 80%, at least 85%, at least 90%, at least 95%, at least 98% or at least 99% sequence identity with an amino acid sequence as represented by SEQ ID NO: 2, 4, 13, 15, 17, 19, 21, 23, 25, or 27, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, or at least 120 of the non-identical amino acid residues, or wherein 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 or even all of the non-identical amino acid residues are conservative amino acid substitutions, preferably as shown in Table 1, of the corresponding amino acid residue of SEQ ID NO: 2, 4, 13, 15, 17, 19, 21, 23, 25, or 27.

Percentages of identity of a polypeptide or protein are indicated with reference to the entire amino acid sequence specifically disclosed herein.

Preferably, the HCP6 protein comprises at least about 500, at least about 600, at least about 700, at least about 800, at least about 900, at least about 1000, at least about 1050, or at least about 1100 amino acid residues, preferably continuous amino acid residues, preferably counted from the N-terminus or the C-terminus of the amino acid sequence, or up to the full length of the amino acid sequence set out in SEQ ID NO: 2, 4, 13, 15, 17, 19, 21, 23, 25, or 27.

Preferably, the HCP6 polypeptide comprises about 500-600, about 600-700, about 700-800, about 800-900, about 900-1000, about 1050-1100, or about 1100-1117, amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 2, 4, 13, 15, 17, 19, 21, 23, 25, or 27.

Preferably, the HCP6 protein comprises at least about 500, at least about 550, at least about 600, at least about 650, at least about 700, at least about 750, at least about 800, at least about 850, at least about 860, at least about 870, at least about 880, or at least about 890 amino acid residues, preferably continuous amino acid residues, preferably counted from the N-terminus or the C-terminus of the amino acid sequence, or up to the full length of the amino acid sequence set out in SEQ ID NO: 2, 13, 15, 17, 19, 21, 23, 25, or 27.

Preferably, the HCP6 polypeptide comprises about 500-550, about 550-600, about 600-650, about 650-700, about 700-750, about 750-800, about 800-850, about 850-860, about 860-870, about 870-890, or about 890-897 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 2, 13, 15, 17, 19, 21, 23, 25, or 27.

The HCP6 proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phacopsoracea, for example soy bean rust, in a plant, plant part, or plant cell by increasing the expression of an HCP6 protein or a functional fragment, orthologue, paralogue or homologue thereof in comparison to wild-type plants, wild-type plant parts or wild-type plant cells.

The present invention also provides a method for increasing resistance to fungal pathogens, in particular a heminecrotrophic pathogen, in particular to rust pathogens (i.e., fungal pathogens of the order Pucciniales), preferably fungal pathogens of the family Phacopsoraceae, preferably against fungal pathogens of the genus *Phacopsora*, most preferably against *Phakopsora pachyrhizi* and *Phakopsora meibomiae*, also known as soy bean rust in plants or plant cells, wherein in comparison to wild type plants, wild type plant parts, or wild type plant cells an HCP6 protein is overexpressed.

The present invention further provides a method for increasing resistance to fungal pathogens of the genus *Phacopsora*, most preferably against *Phakopsora pachyrhizi* and *Phakopsora meibomiae*, also known as soy bean rust in plants or plant cells by overexpression of an HCP6 protein.

In preferred embodiments, the protein amount and/or function of the HCP6 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the HCP6 nucleic acid.

In one embodiment of the invention, the HCP6 protein is encoded by a nucleic acid comprising (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 6, 1, 3, 5, 7, 12, 14, 16, 18, 20, 22, 24, 26, 28, 29, 30, 31, 32, 33, 34, or 35, a functional fragment thereof, or an orthologue or a paralogue thereof, or a splice variant thereof; or by (ii) an exogenous nucleic acid encoding a protein comprising an amino acid sequence having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 4, 13, 15, 17, 19, 21, 23, 25, or 27, a functional fragment thereof, an orthologue or a paralogue thereof, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; or by (iv) an exogenous nucleic acid encoding the same HCP6 protein as the nucleic acids of (i) to (iii) above, but differing from the nucleic acids of (i) to (iii) above due to the degeneracy of the genetic code.

A method for increasing fungal resistance, preferably resistance to Phacopsoracea, for example soy bean rust, in a plant, plant part, or plant cell, by increasing the expression of an HCP6 protein or a functional fragment, orthologue, paralogue or homologue thereof, or a splice variant thereof, wherein the HCP6 protein is encoded by a nucleic acid comprising (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35, or a functional fragment thereof, an orthologue or a paralogue thereof, or a splice variant thereof;

(ii) an exogenous nucleic acid encoding a protein comprising an amino acid sequence having at least 60%, preferably at least 70% sequence identity, at least 80%, at least 90%, at least 95%, at least 98%, at least 99% sequence identity, or even 100% sequence identity with SEQ ID NO: 2, 4, 13, 15, 17, 19, 21, 23, 25, or 27, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or by (iv) an exogenous nucleic acid encoding the same HCP6 protein as the nucleic acids of (i) to (iii) above, but differing from the nucleic acids of (i) to (iii) above due to the degeneracy of the genetic code;

is a further embodiment of the invention.

A method for increasing fungal resistance, preferably resistance to Phacopsoracea, for example soy bean rust, in a plant, plant part, or plant cell, by increasing the expression of an HCP6 protein or a functional fragment, orthologue, paralogue or homologue thereof, or a splice variant thereof, wherein the HCP6 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP6 protein as the nucleic acids of (i) to (iii) above, but differing from the nucleic acids of (i) to (iii) above due to the degeneracy of the genetic code is a further embodiment of the invention.

A method for increasing fungal resistance, preferably resistance to Phacopsoracea, for example soy bean rust, in a plant, plant part, or plant cell, by increasing the expression of an HCP6 protein or a functional fragment, orthologue, paralogue or homologue thereof, or a splice variant thereof, wherein the HCP6 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 6 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP6 protein as the nucleic acids of (i) to (iii) above, but differing from the nucleic acids of (i) to (iii) above due to the degeneracy of the genetic code is a further embodiment of the invention.

In a further method of the invention, the method comprises the steps of (a) stably transforming a plant cell with a recombinant expression cassette comprising (i) a nucleic acid having at least 60% identity, preferably at least 70% sequence identity, at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35, or a functional fragment thereof, or an orthologue or a paralogue thereof, or a splice variant thereof;

(ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 2, 4, 13, 15, 17, 19, 21, 23, 25, or 27, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or (iv) a nucleic acid encoding the same HCP6 polypeptide as the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for an HCP6 protein is expressed in an amount and for a period sufficient to generate or to increase soybean rust resistance in said plant.

Preferably, the method comprises the steps of (a) stably transforming a plant cell with a recombinant expression cassette comprising (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, or a functional fragment thereof, or an orthologue or a paralogue thereof, or a splice variant thereof;

(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) a nucleic acid encoding the same HCP6 polypeptide as the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for an HCP6 protein is expressed in an amount and for a period sufficient to generate or to increase soybean rust resistance in said plant.

Preferably, the method comprises the steps of
(a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 6, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
  (iv) a nucleic acid encoding the same HCP6 polypeptide as the nucleic acids of (i) to (iii) above, but differing from the nucleic acids of (i) to (iii) above due to the degeneracy of the genetic code,
  in functional linkage with a promoter;
(b) regenerating the plant from the plant cell; and
(c) expressing said nucleic acid, optionally wherein the nucleic acid which codes for an HCP6 protein is expressed in an amount and for a period sufficient to generate or to increase soybean rust resistance in said plant.

Preferably, the promoter is a rust induced and/or mesophyll-specific promoter, preferably the the rust induced mesophyll specific promoter 820.

Preferably, the method for increasing fungal resistance, preferably resistance to Phacopsoracea, for example soy bean rust, in a plant, plant part, or plant cell further comprises the step of selecting a transgenic plant expressing
(i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35, or a functional fragment thereof, or an orthologue or a paralogue thereof, or a splice variant thereof;
(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 4, 13, 15, 17, 19, 21, 23, 25, or 27, a functional fragment thereof, an orthologue or a paralogue thereof; preferably the encoded protein confers enhanced fungal resistance relative to control plants;
(iii) an exogenous nucleic acid capable of hybridizing under stringent conditions a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or
(iv) an exogenous nucleic acid encoding the same HCP6 polypeptide as the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of an HCP6 protein, wherein the HCP6 protein is encoded by a nucleic acid comprising
(i) an exogenous nucleic acid having at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35;
(ii) an exogenous nucleic acid encoding a protein comprising an amino acid sequence having at least 80%, at least 90%, at least 95%, at least 98%, at least 99% sequence identity, or even 100% sequence identity with SEQ ID NO: 2, 4, 13, 15, 17, 19, 21, 23, 25, or 27; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or by
(iv) an exogenous nucleic acid encoding the same HCP6 protein as the nucleic acids of (i) to (iii) above, but differing from the nucleic acids of (i) to (iii) above due to the degeneracy of the genetic code,
wherein increasing the expression of the HCP6 protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of an HCP6 protein, wherein the HCP6 protein is encoded by a nucleic acid comprising
(i) an exogenous nucleic acid having at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35;
(ii) an exogenous nucleic acid encoding a protein comprising an amino acid sequence having at least 80%, at least 90%, at least 95%, at least 98%, at least 99% sequence identity, or even 100% sequence identity with SEQ ID NO: 2, 4, 13, 15, 17, 19, 21, 23, 25, or 27; preferably the encoded protein confers enhanced fungal resistance relative to control plants; or
(iii) an exogenous nucleic acid encoding the same HCP6 protein as the nucleic acids of (i) to (ii) above, but differing from the nucleic acids of (i) to (ii) above due to the degeneracy of the genetic code,
wherein increasing the expression of the HCP6 protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (*Fungi imperfecti*). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis*/*Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi, P. meibomiae* |
| Rust (tropical corn) | *Physopella pallescens, P. zeae = Angiopsora zeae* |

TABLE 3

Diseases caused by necrotrophic and/or hemibiotrophic fungi and Oomycetes

| Disease | Pathogen |
|---|---|
| Plume blotch | *Septoria* (*Stagonospora*) *nodorum* |
| Leaf blotch | *Septoria tritici* |
| Ear fusarioses | *Fusarium* spp. |
| Late blight | *Phytophthora infestans* |
| Anthrocnose leaf blight | *Colletotrichum graminicola* (teleomorph: *Glomerella graminicola* Politis); *Glomerella tucumanensis* (anamorph: *Glomerella falcatum* Went) |
| Anthracnose stalk rot | |
| Curvularia leaf spot | *Curvularia clavata, C. eragrostidis, = C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| Didymella leaf spot | *Didymella exitalis* |
| Diplodia leaf spot or streak | *Stenocarpella macrospora = Diplodialeaf macrospora* |
| Brown stripe downy mildew | *Sclerophthora rayssiae* var. *zeae* |
| Crazy top downy mildew | *Sclerophthora macrospora = Sclerospora macrospora* |
| Green ear downy mildew (graminicola downy mildew) | *Sclerospora graminicola* |
| Leaf spots, minor | *Alternaria alternata, Ascochyta maydis, A. tritici, A. zeicola, Bipolaris victoriae = Helminthosporium victoriae* (teleomorph: *Cochliobolus victoriae*), *C. sativus* (anamorph: *Bipolaris sorokiniana = H. sorokinianum = H. sativum*), *Epicoccum nigrum, Exserohilum prolatum = Drechslera prolata* (teleomorph: *Setosphaeria prolata*) *Graphium penicillioides, Leptosphaeria maydis, Leptothyrium zeae, Ophiosphaerella herpotricha*, (anamorph: *Scolecosporiella* sp.), *Paraphaeosphaeria michotii, Phoma* sp., *Septoria zeae, S. zeicola, S. zeina* |
| Northern corn leaf blight (white blast, crown stalk rot, stripe) | *Setosphaeria turcica* (anamorph: *Exserohilum turcicum = Helminthosporium turcicum*) |
| Northern corn leaf spot Helminthosporium ear rot (race 1) | *Cochliobolus carbonum* (anamorph: *Bipolaris zeicola = Helminthosporium carbonum*) |
| Phaeosphaeria leaf spot | *Phaeosphaeria maydis = Sphaerulina maydis* |
| Rostratum leaf spot (*Helminthosporium* leaf disease, ear and stalk rot) | *Setosphaeria rostrata*, (anamorph: *xserohilum rostratum = Helminthosporium rostratum*) |
| Java downy mildew | *Peronosclerospora maydis = Sclerospora maydis* |
| Philippine downy mildew | *Peronosclerospora philippinensis = Sclerospora philippinensis* |
| Sorghum downy mildew | *Peronosclerospora sorghi = Sclerospora sorghi* |

TABLE 3-continued

Diseases caused by necrotrophic and/or hemibiotrophic fungi and Oomycetes

| Disease | Pathogen |
|---|---|
| Spontaneum downy mildew | *Peronosclerospora spontanea* = *Sclerospora spontanea* |
| Sugarcane downy mildew | *Peronosclerospora sacchari* = *Sclerospora sacchari* |
| Sclerotium ear rot (southern blight) | *Sclerotium rolfsii* Sacc. (teleomorph: *Athelia rolfsii*) |
| Seed rot-seedling blight | *Bipolaris sorokiniana, B. zeicola* = *Helminthosporium carbonum, Diplodia maydis, Exserohilum pedicillatum, Exserohilum turcicum* = *Helminthosporium turcicum, Fusarium avenaceum, F. culmorum, F. moniliforme, Gibberella zeae* (anamorph: *F. graminearum*), *Macrophomina phaseolina, Penicillium* spp., *Phomopsis* sp., *Pythium* spp., *Rhizoctonia solani, R. zeae, Sclerotium rolfsii, Spicaria* sp. |
| Selenophoma leaf spot | *Selenophoma* sp. |
| Yellow leaf blight | *Ascochyta ischaemi, Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea, Polymyxa graminis,*

Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), Plasmopara (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (rhizoctonia root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (*Fungi imperfecti*) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (verticillium wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, more preferably heminecrotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales (rust), previously known as Uredinales, among which in particular the Melompsoraceae. Preferred are Phakopsoraceae, more preferably *Phakopsora*. Especially preferred are *Phakopsora pachyrhizi* and/or *Phakopsora meibomiae*.

Also preferred rust fungi are selected from the group of *Puccinia, Gymnosporangium, Juniperus, Cronartium, Hemileia,* and *Uromyces*; preferably *Puccinia sorghi, Gymnosporangium junlperi-virginianae, Juniperus virginiana, Cronartium ribicola, Hemilela vastatrix Puccinia graminis, Puccinia coronata, Uromyces phaseoli, Puccinia hemerocallidis, Puccinia persistens* subsp. *Triticina, Puccinia striiformis, Puccinia graminis* causes, and/or *Uromyces appendeculatus*.

Further preferred pathogens, preferably pathogens of maize, are pathogens causing stalk rot diseases, in particular *Fusarium* stalk rot, *Gibberella* stalk rot, *Diplodia* stalk rot, and Charcoal rot and pathogens causing anthracnose. Preferred pathogens causing *Fusarium* stalk rot are *Fusarium verticillioides, Fusarium proliferatum* or *Fusarium subglutinans*. A preferred pathogen causing *Gibberella* stalk rot is *Fusarium graminearum*. A preferred pathogen causing *Diplodia* stalk rot is *Diplodia maydis*. A preferred pathogen causing Charcoal rot is *Macrophomina phaseolina*. A preferred pathogen causing anthracnose is *Colletotrichum graminicola*.

HCP6 Expression Constructs and Vector Constructs

A recombinant vector construct comprising:
(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35, or a functional fragment thereof, or an orthologue or a paralogue thereof, or a splice variant thereof;
(ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 2, 4, 13, 15, 17, 19, 21, 23, 25, or 27, a functional fragment thereof, an orthologue or a paralogue thereof; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or
(iv) a nucleic acid encoding the same HCP6 protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35;
(ii) a nucleic acid coding for a protein comprising an amino acid sequence having at least 80%, at least 90%, at least 95%, at least 98%, at least 99% sequence identity, or even 100% sequence identity with SEQ ID NO: 2, 4, 13, 15, 17, 19, 21, 23, 25, or 27; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or
(iv) a nucleic acid encoding the same HCP6 protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 1,
(ii) a nucleic acid coding for a protein having at least 80%, at least 90%, at least 95%, at least 98%, at least 99% sequence identity, or even 100% sequence identity with SEQ ID NO: 2; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
(iv) a nucleic acid encoding the same HCP6 protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 6;
(ii) a nucleic acid coding for a protein having at least 80%, at least 90%, at least 95%, at least 98%, at least 99% sequence identity, or even 100% sequence identity with SEQ ID NO: 2; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
(iv) a nucleic acid encoding the same HCP6 protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

In the case of a genomic library, the natural genetic environment of the nucleic acid sequence is preferably retained, at least in part. The environment preferably flanks the nucleic acid sequence at least on one side and has a sequence length of at least 50 bp, preferably at least 500 bp, especially preferably at least 1000 bp, most preferably at least 5000 bp.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

In preferred embodiments, the increase in the protein amount and/or activity of the HCP6 protein takes place in a constitutive or tissue-specific manner. In especially preferred embodiments, an essentially pathogen-induced increase in the protein amount and/or protein activity takes place, for example by recombinant expression of the HCP6 nucleic acid under the control of a fungal-inducable promoter. In particular, the expression of the HCP6 nucleic acid takes place on fungal infected sites, where, however, preferably the expression of the HCP6 nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruitpreferred, ovule-preferred, male tissue-preferred, seed-preferred, integument-preferred, tuber-preferred, stalk-preferred, pericarp-preferred, leaf-preferred, stigma-preferred, pollenpreferred, anther-preferred, a petal-preferred, sepal-preferred, pedicel-preferred, siliquepreferred, stem-preferred, root-preferred promoters and/or the like. Seed preferred promoters are preferentially expressed during seed development and/or germination. For example, seed preferred promoters can be embryo-preferred, endosperm preferred and seed coat preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosinpromoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-spezific promoters may be selected from the group consisting of:

WIR5 (=GstA1); acc. X56012; Dudler & Schweizer,

GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998), GLP2a, acc. AJ237942, Schweizer P., Christoffel A. and Dudler R., Plant J. 20, 541 (1999); Prx7, acc. AJ003141, Kristensen B. K., Ammitzböll H., Rasmussen S. K. and Nielsen K. A., Molecular Plant Pathology, 2(6), 311 (2001);

GerA, acc. AF250933; Wu S., Druka A., Horvath H., Kleinhofs A., Kannangara G. and von Wettstein D., Plant Phys Biochem 38, 685 (2000);

OsROC1, acc. AP004656

RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999); Chitinase ChtC2-Promoter from potato (Ancillo et al., Planta. 217(4), 566, (2003));

AtProT3 Promoter (Grallath et al., Plant Physiology. 137(1), 117 (2005));

SHN-Promoters from *Arabidopsis* (AP2/EREBP transcription factors involved in cutin and wax production) (Aaron et al., Plant Cell. 16(9), 2463 (2004)); and/or GSTA1 from wheat (Dudler et al., WP2005306368 and Altpeter et al., Plant Molecular Biology. 57(2), 271 (2005)).

Mesophyll-specific promoters may be selected from the group consisting of:

PPCZm1 (=PEPC); Kausch A. P., Owen T. P., Zachwieja S. J., Flynn A. R. and Sheen J., Plant Mol. Biol. 45, 1 (2001);

OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);

OsPPDK, acc. AC099041;

TaGF-2.8, acc. M63223; Schweizer P., Christoffel A. and Dudler R., Plant J. 20, 541 (1999);

TaFBPase, acc. X53957;

TaWIS1, acc. AF467542; US 200220115849;

HvBIS1, acc. AF467539; US 200220115849;

ZmMIS1, acc. AF467514; US 200220115849;

HvPR1a, acc. X74939; Bryngelsson et al., Mol. Plant Microbe Interacti. 7 (2), 267 (1994);

HvPR1b, acc. X74940; Bryngelsson et al., Mol. Plant Microbe Interact. 7(2), 267 (1994);

HvB1,3gluc; acc. AF479647;

HvPrx8, acc. AJ276227; Kristensen et al., Molecular Plant Pathology, 2(6), 311 (2001);

and/or

HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of

PcUbi promoter from parsley (WO 03/102198)

CaMV 35S promoter: Cauliflower Mosaic Virus 35S promoter (Benfey et al. 1989 EMBO J. 8(8): 2195-2202), STPT promoter: *Arabidopsis thaliana* Short Triose phosphate translocator promoter (Accession NM_123979)

Act1 promoter: *Oryza sativa* actin 1 gene promoter (McElroy et al. 1990 PLANT CELL 2(2) 163-171 a) and/or EF1A2 promoter: *Glycine max* translation elongation factor EF1 alpha (US 20090133159).

In preferred embodiments, the increase in the protein quantity or function of the HCP6 protein takes place in a constitutive or tissue-specific manner. In especially preferred embodiments, an essentially pathogen-induced increase in the protein quantity or protein function takes place, for example by exogenous expression of the HCP6 nucleic acid under the control of a fungal-inducible promoter, preferably a rust-inducible promoter. In particular, the expression of the HCP6 nucleic acid takes place on fungal infected sites, where, however, preferably the expression of the HCP6 nucleic acid sequence remains essentially unchanged in tissues not infected by fungus.

Preferably, the HCP6 nucleic acid is under the control of a rust induced mesophyll specific promoter. More preferably, the promoter is the rust induced mesophyll specific promoter 820.

A preferred terminator is the terminator of the cathepsin D inhibitor gene from *Solanum tuberosum*.

Preferred promoter-terminator combinations with the gene of interest in between are a promoter from parsley, preferably, the parsley ubiquitine promoter or the maize ubiquitin promoter, in combination with the terminator of the cathepsin D inhibitor gene from *Solanum tuberosum*. Another preferred promoter-terminator combination is the rust induced mesophyll specific promoter 820 in combination with the terminator of the cathepsin D inhibitor gene from *Solanum tuberosum*.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

Transgenic Organisms; Transgenic Plants, Plant Parts, and Plant Cells

A preferred embodiment is a transgenic plant, transgenic plant part, or transgenic plant cell overexpressing an exogenous HCP6 protein. Preferably, the HCP6 protein overexpressed in the plant, plant part or plant cell is encoded by a nucleic acid comprising (i) an exogenous nucleic acid having at least 60% identity with SEQ ID NO: 6, 1, 3, 5, 7, 12, 14, 16, 18, 20, 22, 24, 26, 28, 29, 30, 31, 32, 33, 34, or 35, or a functional fragment, thereof, an orthologue or a paralogue thereof, or a splice variant thereof; or by (ii) an exogenous nucleic acid encoding a protein comprising an amino acid sequence having at least 60% identity with SEQ ID NO: 2, 4, 13, 15, 17, 19, 21, 23, 25, or 27, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or by (iv) an exogenous nucleic acid encoding the same HCP6 protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35; or comprises an exogenous nucleic acid encoding a protein having at least 80%, at least 90%, at least 95%, at least 98%, at least 99% sequence identity, or even 100% sequence identity with SEQ ID NO: 2, 4, 13, 15, 17, 19, 21, 23, 25, or 27.

A preferred embodiment is a transgenic plant, transgenic plant part, or transgenic plant cell overexpressing an exogenous HCP6 protein. Preferably, the HCP6 protein overexpressed in the plant, plant part or plant cell is encoded by
(i) an exogenous nucleic acid having at least 60% identity with SEQ ID NO: 1 or a functional fragment, thereof, an orthologue or a paralogue thereof, or a splice variant thereof; or by
(ii) an exogenous nucleic acid encoding a protein having at least 60% identity with SEQ ID NO: 2, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
(iv) an exogenous nucleic acid encoding the same HCP6 protein as the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous HCP6 protein. Preferably, the HCP6 protein overexpressed in the plant, plant part or plant cell is encoded by
(i) an exogenous nucleic acid having at least 60% identity with SEQ ID NO: 6 or a functional fragment, thereof, an orthologue or a paralogue thereof, or a splice variant thereof; or by
(ii) an exogenous nucleic acid encoding a protein having at least 60% identity with SEQ ID NO: 2, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
(iv) an exogenous nucleic acid encoding the same HCP6 protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 80%, at least 90%, at least 95%, at least 98%, at least 99% sequence identity, or even 100% sequence identity with SEQ ID NO: 2 or 4.

Most preferably, the exogenous nucleic acid has at least 80%, at least 90%, at least 95%, at least 98%, at least 99% sequence identity, or even 100% sequence identity with SEQ ID NO: 6; or comprises an exogenous nucleic acid encoding a protein having at least 80%, at least 90%, at least 95%, at least 98%, at least 99% sequence identity, or even 100% sequence identity with SEQ ID NO: 2.

In preferred embodiments, the protein amount of a HCP6 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the HCP6 nucleic acid.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et. al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et. al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the HCP6 nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, constructs or vectors or expression cassettes are not present in the genome of the original plant or are present in the genome of the transgenic plant not at their natural locus of the genome of the original plant.

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae,* also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C. O. Lehm), sugar pea (*Pisum sativum* L. convar. *axiphium* Alef emend. C. O. Lehm), also called snow pea, edible-podded pea or mangetout, (*Pisum granda sneida* L. convar. *sneidulo* p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, *dolichos* bean, lablab bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phacosporaceae, for example soybean rust, wherein the recombinant nucleic acid used to generate a transgenic plant comprises a promoter that is functional in the plant cell, operably linked to an HCP6 nucleic acid, which is preferably SEQ ID NO: 1, and a terminator regulatory sequence.

In one embodiment, the present invention refers to a method for the production of a transgenic plant, transgenic plant part, or transgenic plant cell having increased fungal resistance, comprising
(a) introducing a recombinant vector construct according to the present invention into a plant, a plant part or a plant cell and
(b) generating a transgenic plant from the plant, plant part or plant cell.

Preferably, the method for the production of the transgenic plant, transgenic plant part, or transgenic plant cell further comprises the step
(c) expressing the HCP6 protein, preferably encoded by a nucleic acid comprising
  (i) an exogenous nucleic acid having at least 60% identity with SEQ ID NO: 6, 1, 3, 5, 7, 12, 14, 16, 18, 20, 22, 24, 26, 28, 29, 30, 31, 32, 33, 34, or 35, a functional fragment thereof, an orthologue or a paralogue thereof, or a splice variant thereof;
  (ii) an exogenous nucleic acid encoding a protein comprising an amino acid sequence having at least 60% identity with SEQ ID NO: 2, 4, 13, 15, 17, 19, 21, 23, 25, or 27, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
  (iv) an exogenous nucleic acid encoding the same HCP6 protein as the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step
(c) expressing the HCP6 protein, preferably encoded by
  (i) an exogenous nucleic acid having at least 60% identity with SEQ ID NO: 1, a functional fragment thereof, an orthologue or a paralogue thereof, or a splice variant thereof;
  (ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
  (iv) an exogenous nucleic acid encoding the same HCP6 protein as the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step
(c) expressing the HCP6 protein, preferably encoded by
  (i) an exogenous nucleic acid having at least 60% identity with SEQ ID NO: 6, a functional fragment thereof, an orthologue or a paralogue thereof, or a splice variant thereof;
  (ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or by
  (iv) an exogenous nucleic acid encoding the same HCP6 protein as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing
  (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 6, 1, 3, 5, 7, 12, 14, 16, 18, 20, 22, 24, 26, 28, 29, 30, 31, 32, 33, 34, or 35, or a functional fragment thereof, or an orthologue or a paralogue thereof, or a splice variant thereof;
  (ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 4, 13, 15, 17, 19, 21, 23, 25, or 27, a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP6 protein; preferably wherein the nucleic acid molecute codes for a polypeptide which has essentially identical properties to the polypeptide described in SEQ ID NO: 2 or 4; preferably the encoded protein confers enhanced fungal resistance relative to control plants; and/or
  (iv) an exogenous nucleic acid encoding the same HCP6 polypeptide as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises
(i) the exogenous nucleic acid having at least 60% identity with SEQ ID NO: 6, 1, 3, 5, 7, 12, 14, 16, 18, 20, 22, 24, 26, 28, 29, 30, 31, 32, 33, 34, or 35, a functional fragment thereof, an orthologue or a paralogue thereof, or a splice variant thereof;
(ii) the exogenous nucleic acid encoding a protein comprising an amino acid sequence having at least 60% identity with SEQ ID NO: 2, 4, 13, 15, 17, 19, 21, 23, 25, or 27, or a functional fragment thereof, an orthologue or a paralogue thereof; preferably the encoded protein confers enhanced fungal resistance relative to control plants;
(iii) the exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or
(iv) the exogenous nucleic acid encoding the same HCP6 protein as the nucleic acids of (i) to (iii) above, but differing from the nucleic acids of (i) to (iii) above due to the degeneracy of the genetic code;
preferably, the step of harvesting the seeds of the transgenic plant and planting the seeds and growing the seeds to plants, wherein the grown plant(s) comprises
(i) the exogenous nucleic acid having at least 60% identity with SEQ ID NO: 6, 1, 3, 5, 7, 12, 14, 16, 18, 20, 22, 24, 26, 28, 29, 30, 31, 32, 33, 34, or 35, a functional fragment thereof, an orthologue or a paralogue thereof, or a splice variant thereof;
(ii) the exogenous nucleic acid encoding a protein comprising an amino acid sequence having at least 60% identity with SEQ ID NO: 2, 4, 13, 15, 17, 19, 21, 23, 25, or 27, or a functional fragment thereof, an orthologue or a paralogue thereof; preferably the encoded protein confers enhanced fungal resistance relative to control plants;
(iii) the exogenous nucleic acid capable of hybridizing under stringent conditions with a complementary sequence of any of the nucleic acids according to (i) or (ii); preferably encoding a HCP6 protein; preferably wherein the nucleic acid molecule codes for a polypeptide which has essentially identical properties to the polypeptide described in SEQ ID NO: 2 or 4; preferably the encoded protein confers enhanced fungal resistance relative to control plants; and/or
(iv) the exogenous nucleic acid encoding the same HCP6 protein as the nucleic acids of (i) to (iii) above, but differing from the nucleic acids of (i) to (iii) above due to the degeneracy of the genetic code;
is repeated more than one time, preferably, 1, 2, 3, 4, 5, 6, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the HCP6 gene or by directly screening for the HCP6 nucleic acid).

Furthermore, the use of the exogenous HCP6 nucleic acid or the recombinant vector construct comprising the HCP6 nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the HCP6 nucleic acid or HCP6 protein. The harvestable parts may be seeds, roots, leaves and/or flowers comprising the HCP6 nucleic acid or HCP6 protein or parts thereof. Preferred parts of soy plants are soy beans comprising the HCP6 nucleic acid or HCP6 protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the HCP6 nucleic acid or HCP6 protein.

Methods for Manufacturing a Product

In one embodiment the method for the production of a product comprises
a) growing the plants of the invention or obtainable by the methods of invention and
b) producing said product from or by the plants of the invention and/or parts, e.g. seeds, of these plants.

In a further embodiment the method comprises the steps
a) growing the plants of the invention, b) removing the harvestable parts as defined above from the plants and c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the HCP6 nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing an HCP6 protein, preferably encoded by a nucleic acid comprising
  (i) an exogenous nucleic acid having at least 60% identity with SEQ ID NO: 6, 1, 3, 5, 7, 12, 14, 16, 18, 20, 22, 24, 26, 28, 29, 30, 31, 32, 33, 34, or 35, a functional fragment thereof, an orthologue or a paralogue thereof, or a splice variant thereof;
  (ii) an exogenous nucleic acid encoding a protein comprising an amino acid sequence having at least 60% identity with SEQ ID NO: 2, 4, 13, 15, 17, 19, 21, 23, 25, or 27, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP6 protein; preferably wherein the nucleic acid molecute codes for a polypeptide which has essentially identical properties to the polypeptide described in SEQ ID NO: 2 or 4; preferably the encoded protein confers enhanced fungal resistance relative to control plants; and/or by
  (iv) an exogenous nucleic acid encoding the same HCP6 protein as the nucleic acids of (i) to (iii) above, but differing from the nucleic acids of (i) to (iii) above due to the degeneracy of the genetic code.

Another preferred embodiment is a method for plant improvement comprising
(a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding the HCP6 protein; and optionally
(f) producing propagation material from the plants expressing the nucleic acid encoding the HCP6 protein.

The transgenic plants may be selected by known methods as described above (e.g., by screening for the presence of one or more markers which are encoded by plant-expressible genes co-transferred with the HCP6 gene or screening for the HCP6 nucleic acid itself).

According to the present invention, the introduced HCP6 nucleic acid may be maintained in the plant cell stably if it is incorporated into a non-chromosomal autonomous replicon or integrated into the plant chromosomes. Whether present in an extra-chromosomal nonreplicating or replicating vector construct or a vector construct that is integrated into a chromosome, the exogenous HCP6 nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1

General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2

Cloning of Overexpression Vector Constructs

The cDNA was produced from *Arabidopsis thaliana* (ecotype Col-0) RNA by using the Superscript II cDNA synthesis kit (Invitrogen). All steps of cDNA preparation and purification were performed according as described in the manual.

First, the HCP6 sequence from ATG to Stop (SEQ ID NO: 1) was specifically amplified from the cDNA by PCR as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.25 mM of each dNTP, 100 ng cDNA of *Arabidopsis thaliana* (var Columbia-0), 10 pmol forward primer, 10 pmol reverse primer, 3% DMSO (v/v), 1.5 mM MgCl$_2$, 1 u Phusion hot-start, Pfu Ultra, Pfu Turbo or Herculase DNA polymerase.

The amplification cycles were as follows:
1 cycle of 120 seconds at 98° C., followed by 5 cycles with decreasing annealing temperature (1° C. per cycle) from 70° C. to 66° C. (each cycle: denaturation 20 sec at 98° C., 60 sec annealing 70° C. down to 66° C., and extension at 72° C. for 180 sec), followed by 30 cycles of in each case 20 seconds at 98° C., 60 seconds at 65° C. and 180 seconds at 72° C., followed by 1 cycle of 5 minutes at 72° C., then 4° C.

The primers (as shown in SEQ ID NO: 8 and 9) were designed in a way that they specifically bind to sequences around the start ATG and around the stop codon of the HCP6 coding sequence.

```
i) forward primer:
                                    (SEQ ID NO: 8)
5'- TGCATGGCTTCTTCTTCTTCCTCACCT -3' ii) reverse primer:
                                    (SEQ ID NO: 9)
5'- CGCGCTAGTGAATTGACAACACAACG -3'
```

The amplified fragment (2700 bp) was eluted and purified from an 1% agarose gel by using the Nucleospin Extract II Kit (Macherey and Nagel, Dueren, Germany). As the amount of amplified DNA was very low, a second PCR was performed to increase the amount of the fragment and to add attB recombination sites in front and behind the gene that facilitates BP reaction cloning of the HCP-6 fragment into an DONOR vector (Gateway system, (Invitrogen, Life Technologies, Carlsbad, Calif., USA).

The HCP6 full-length sequence including the attached attB-sites was specifically amplified from the eluted PCR fragment (see above) by PCR as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.25 mM of each dNTP, 10-50 ng template DNA derived from the previous PCR of, 10 pmol forward primer, 10 pmol reverse primer, 3% DMSO (v/v), 1.5 mM MgCl$_2$, 1 u Phusion hot-start, Pfu Ultra, Pfu Turbo or Herculase DNA polymerase.

The amplification cycles were as follows:
1 cycle of 120 seconds at 98° C., followed by 10 cycles with decreasing annealing temperature (1° C. per cycle) from 70° C. to 61° C. (each cycle: denaturation 30 sec at 98° C., 60 sec annealing 70° C. down to 61° C., and extension at 72° C. for 180 sec), followed by 20 cycles of in each case 30 seconds at 98° C., 60 seconds at 60° C. and 180 seconds at 72° C., followed by 1 cycle of 5 minutes at 72° C., then 4° C.

The primers (as shown in SEQ ID NO: 10 and 11) were designed in a way that an attB1-recombination site (Gateway system, Invitrogen Life Technologies, Carlsbad, Calif., USA) is located in front of the start-ATG and an attB2 recombination site is located directly downstream of the stop-codon.

```
i) forward primer:
                                    (SEQ ID NO: 10)
5'-GGGGACAAGTTTGTACAAAAAAGCAGGCTCTATGGCTTCTTC

TTCTTCCTCACCT-3' ii) reverse primer:
                                    (SEQ ID NO: 11)
5'GGGGACCACTTTGTACAAGAAAGCTGGGTCCTAGTGAATTGAC

AACACAACG -3'
```

The amplified fragments were transferred to a pENTRY-B vector by using the BP reaction (Gateway system, Invitrogen, Life Technologies, Carlsbad, Calif., USA) according to the protocol provided by the supplier in a way that the full-length HCP6 fragment is located in sense direction between the attL1 and attL2 recombination sites.

It is also possible to generate all DNA fragments mentioned in this invention by DNA synthesis (e.g. Geneart, Regensburg, Germany).

Figure 2:
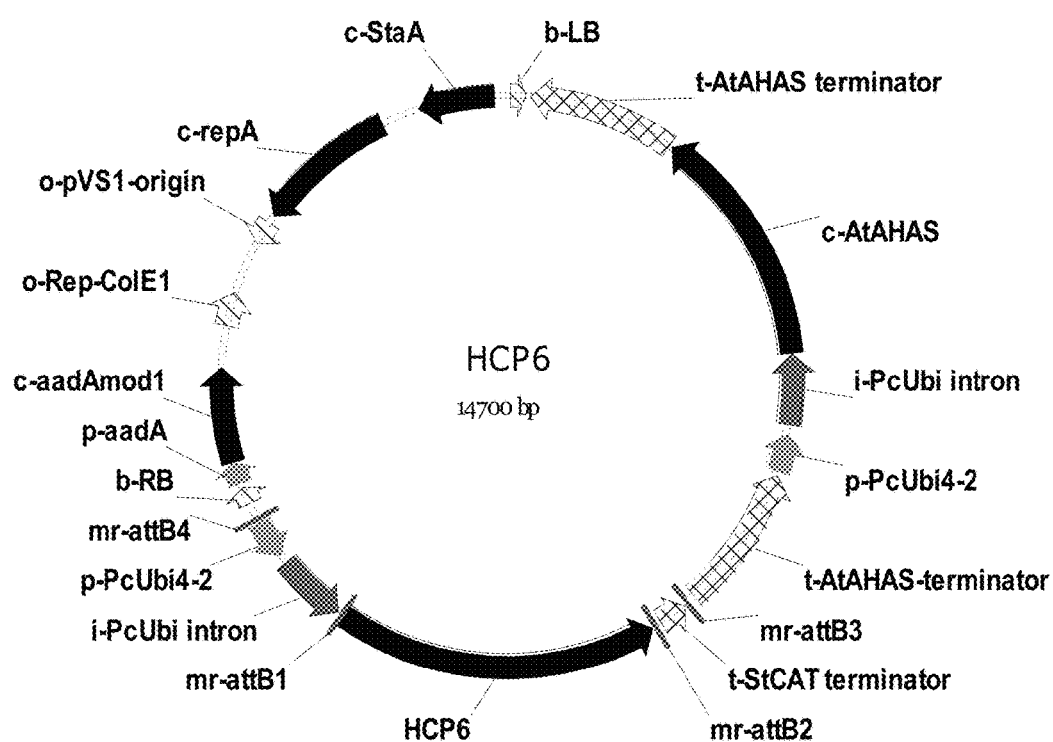

To obtain the binary plant transformation vector, a triple LR reaction (Gateway system, Invitrogen, Life Technologies, Carlsbad, Calif., USA) was performed according to manufacturer's protocol by using a pENTRY-A vector containing a parsley ubiquitine promoter, the HCP6 full-length gene in a pENTRY-B vector and a pENTRY-C vector containing the terminator of the cathepsin D inhibitor gene from *Solanum tuberosum*. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection under control of a pcUbi-promoter (see FIG. 2). The recombination reaction was transformed into *E. coli* (DHSalpha), mini-prepped and screened by specific restriction digestions. A positive clone containing the construct was sequenced and submitted soy transformation.

Example 3

Soy Transformation

The expression vector constructs (see example 2) were transformed into soy.
3.1 Sterilization and Germination of Soy Seeds
Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 pEinstein/rrs) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 µl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the Agrobacteria were pelleted by centrifugation for 10 min at 5,500×g at 20° C. The pellet was resuspended in liquid CCM to the desired density ($OD_{600}$ 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a coculture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soyplants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any pre-formed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol. Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 $\mu E/m^2 s$. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4

Pathogen Assay 4.1. Growth of Plants

10 $T_1$ plants per event were potted and grown for 3-4 weeks in the phytochamber (16 h-day-und 8 h-night-Rhythm at a temperature of 16 and 22° C. and a humidity of 75%) till the first 2 trifoliate leaves were fully expanded.

4.2 Inoculation

The plants were inoculated with spores of *P. pachyrhizi*.

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×10 spores/ml. For the microscopy, a density of >5×$10^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5

Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6

Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 44 T1 soybean plants (5 independent events, 7-10 plants each) expressing HCP6 protein were inoculated with spores of *Phakopsora pachyrhizi* The macroscopic disease symptoms of soy against *P. pachyrhizi* of the inoculated soybean plants were scored 14 days after inoculation.

The average of the percentage of the leaf area showing fungal colonies or strong yellowing/browning on all leaves was considered as diseased leaf area. At all 44 soybean T1 plants expressing HCP6 (expression checked by RT-PCR) were evaluated in parallel to non-transgenic control plants. Non-transgenic soy plants grown in parallel to the transgenic plants were used as control. The average of the diseased leaf area is shown in FIG. 8 for plants expressing recombinant HCP6 compared with wildtype plants. Overexpression of HCP6 reduces the diseased leaf area in comparison to non-transgenic control plants by 26.1% in average over all events and plants generated. This data clearly indicates that the in-planta expression of the HCP6 expression vector construct lead to a lower disease scoring of transgenic plants compared to non-transgenic controls. So, the expression of HCP6 (as shown in SEQ ID NO: 1 (nucleic acid) and SEQ ID NO: 2 (protein), respectively) in soybean significantly ($p<0.05$) increases the resistance of soy against soybean rust.

Example 7

Construction of Maize Expression Cassettes

The nucleic acid sequence encoding the long version of the cDNA of HCP6 (as shown in SEQ ID NO:7) was synthesized in a way that enables further cloning. The expression cassettes were then assembled in a vector by cloning the synthesized DNA encoding the HCP6 gene from *Arabidopsis thaliana* downstream of a SCBV254 promoter (Sugarcane Bacilliform Virus promoter fragment ScBV-254) and upstream of a t-nos terminator (3'UTR of Nopaline Synthase from *Agrobacterium tumefaciens*). An intron from the rice Met1 gene was also cloned in between of the promoter and the HCP6 sequence.

Plant transformation binary vectors such as pBi-nAR were used (Höfgen & Willmitzer 1990, Plant Sci. 66:221-230). Further examples for plant binary vectors are the pSUN300 or pSUN2-GW vectors and the pPZP vectors (Hajdukiewicz et al., Plant Molecular Biology 25: 989-994, 1994). As target a binary plant transformation vector was used which is composed of: (1) a Kanamycin resistance cassette for bacterial selection (2) a pVS1 origin for replication in Agrobacteria (3) a ColE1 origin of replication for stable maintenance in *E. coli* and (4) between the right and left border an ZmAHAS gene as selectable marker under control of a ZmAHAS-promoter.

Construction of the binary vectors was performed by ligation of the HCP6 expression cassette, as described above, into the binary vector. The recombinant vector containing the HCP6 expression cassette was transformed into Top10 cells (Invitrogen) using standard conditions. Transformed cells were selected on LB agar containing 50 μg/ml kanamycin grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al., 1989, "Molecular Cloning: A Laboratory Manual," 2nd Edition, Cold Spring Harbor Laboratory Press, Cold Spring Harbor, N.Y.).

Example 8

Maize Transformation

*Agrobacterium* cells harboring a plasmid containing the gene of interest and the mutated maize AHAS gene were grown in YP medium supplemented with appropriate antibiotics for 1-2 days. One loop of *Agrobacterium* cells was collected and suspended in 1.8 ml M-LS002 medium (LS-inf). The cultures were incubated while shaking at 1,200 rpm for 5 min-3 hrs. Corn cobs were harvested at 8-11 days after pollination. The cobs were sterilized in 20% Clorox solution for 5 min, followed by spraying with 70% Ethanol and then thoroughly rinsed with sterile water. Immature embryos 0.8-2.0 mm in size were dissected into the tube containing *Agrobacterium* cells in LS-inf solution.

The constructs were transformed into immature embryos by a protocol modified from Japan Tobacco *Agrobacterium* mediated plant transformation method (U.S. Pat. Nos. 5,591,616; 5,731,179; 6,653,529; and U.S. Patent Application Publication No. 2009/0249514). Two types of plasmid vectors were used for transformation. One type had only one T-DNA border on each of left and right side of the border, and selectable marker gene and gene of interest were between the left and right T-DNA borders. The other type was so called "two T-DNA constructs" as described in Japan Tobacco U.S. Pat. No. 5,731,179. In the two DNA constructs, the selectable marker gene was located between one set of T-DNA borders and the gene of interest was included in between the second set of T-DNA borders. Either plasmid vector can be used. The plasmid vector was electroporated into *Agrobacterium*.

*Agrobacterium* infection of the embryos was carried out by inverting the tube several times. The mixture was poured onto a filter paper disk on the surface of a plate containing co-cultivation medium (M-LS-011). The liquid agro-solution was removed and the embryos were checked under a microscope and placed scutellum side up. Embryos were cultured in the dark at 22° C. for 2-4 days, and transferred to M-MS-101 medium without selection and incubated for four to seven days. Embryos were then transferred to M-LS-202 medium containing 0.75 µM imazethapyr and grown for three weeks at 27° C. to select for transformed callus cells.

Plant regeneration was initiated by transferring resistant calli to M-LS-504 medium supplemented with 0.75 µM imazethapyr and growing under light at 27° C. for two to three weeks. Regenerated shoots were then transferred to a rooting box with M-MS-618 medium (0.5 µM imazethapyr). Plantlets with roots were transferred to soil-less potting mixture and grown in a growth chamber for a week, then transplanted to larger pots and maintained in a greenhouse until maturity.

Transgenic maize plant production is also described, for example, in U.S. Pat. Nos. 5,591,616 and 6,653,529; U.S. Patent Application Publication No. 2009/0249514; and WO/2006136596, each of which are hereby incorporated by reference in their entirety. Transformation of maize may be made using *Agrobacterium* transformation; as described in U.S. Pat. Nos. 5,591,616; 5,731,179; U.S. Patent Application Publication No. 2002/0104132, and the like. Transformation of maize (*Zea mays* L.) can also be performed with a modification of the method described by Ishida et al. (Nature Biotech., 1996, 14:745-750). The inbred line A188 (University of Minnesota) or hybrids with A188 as a parent are good sources of donor material for transformation (Fromm et al., Biotech, 1990, 8:833), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system is described in WO 94/00977 and WO 95/06722. Vectors are constructed as described. Various selection marker genes are used including the maize gene encoding a mutated acetohydroxy acid synthase (AHAS) enzyme (U.S. Pat. No. 6,025,541). Similarly, various promoters are used to regulate the trait gene to provide constitutive, developmental, inducible, tissue or environmental regulation of gene transcription.

Excised embryos can be used and can be grown on callus induction medium, then maize regeneration medium, containing imidazolinone as a selection agent. The Petri dishes are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

Example 9

Fusarium and Colletotrichum Resistance Screening

Transgenic plants are grown in greenhouse or phytochamber under standard growing conditions in a controlled environment (20-25° C., 60-90% humidity). Shortly after plants enter the reproductive phase the transgenic plants are inoculated near the base of the stalk using a fungal suspension of spores (105 spores in PBS solution) of *Fusarium* ssp. or *Colletotrichum graminicola*. Plants are incubated for 2-4 weeks at 20-25° C. and 60-90% humidity.

For scoring the disease, stalks were split and the progression of the disease is scored by observation of the characteristic brown to black color of the fungus as it grows up the stalk. Disease ratings were conducted by assigning a visual score. Per experiment the diseased leaf area of more than 10 transgenic plants (and wild-type plants as control) is scored. For analysis the average of the diseased leaf area of the non-transgenic mother plant is set to 100% to calculate the relative diseased leaf area of the transgenic lines The expression of the HCP6 gene will lead to enhanced resistance of corn against *Fusarium* ssp. And *Colletotrichum graminicola*.

SEQUENCE LISTING

<160> NUMBER OF SEQ ID NOS: 35

<210> SEQ ID NO 1
<211> LENGTH: 2694
<212> TYPE: DNA
<213> ORGANISM: Arabidopsis thaliana
<220> FEATURE:
<221> NAME/KEY: source
<222> LOCATION: 1..2694
<223> OTHER INFORMATION: /organism="Arabidopsis thaliana"
      /note="Nucleotide sequence HCP6 splice variant 1"
      /mol_type="unassigned DNA"

<400> SEQUENCE: 1

```
atggcttctt cttcttcctc acctcgcaac tggagataca atgtcttcac gagcttccat     60
ggaccagacg tccgtattaa atttctcagt catttacgtc aacagtttat ttacaatgga    120
attactatgt tcgatgacaa cgggatcgaa agaagccaaa ttatcgctcc agctctcaaa    180
aaagccattg gagaatcgag gatcgcgatc ttattgctct cgaagaacta tgcttcttcc    240
agttggtctt tggatgagct attggagatt ttaaagtgca agaagatat agggcaaata    300
gtgatgactg tcttctacga agttgatcct tctgatgtcc gcaaccaaac cggagatttt    360
gggattgctt ttaaagaaac ttgtgctcat aaaacagagg aggagaggca aaatggacc    420
caagctttga cctatgtggg caacattgcc ggagaagact taaacactg gcccaatgaa    480
gctaaaatga tcgagaagat tgcaagagat gtttcagata tactaaacgt cacaccgtgt    540
agggattttg atggcatggt tggactaaac gatcatttga gggaaatgga gtctttgcta    600
gatttaaaga atgatggagt taagattgtt ggaatctctg gtcctgcagg cattggtaaa    660
agtaccattg ctacagcttt acatggtcga ctctctaaca tgtttcagcg tacttgtttt    720
gtggacaatc ttagggaaag ctataagatt ggtcttgatg agtatcgttt gaagttgcac    780
ttacaacagc aacttcttgc atatgtttta aatcaggata aaattagggt gggccattta    840
agtgtgatga agaaaggct tgacgacttg agggttctta ttattcttga tgatgtggag    900
catctatatc aactagaggc tttggctgat atcaggtggt ttggtcctgg aagtagggtg    960
atagtgacca ctgaaaacag agagattttg ctgcaacatg gtatcaagga tatataccat   1020
gtgggttttc catcagaagg agaagctcta atgatctttt gtctatctgc ttttagacaa   1080
ccctctccac cttatggttt tttgaagctt acatatgaag ttgcaagtat tgtgggtaat   1140
cttccattgg gtctgcatgt tttggggacg ttattgtggg aaaaagtca ggctgactgg   1200
attgaagaac taccaaggtt gaaagactgt cttgatggaa gaattgagag tgtattgaaa   1260
gttggctatg agagtttata tgagaaagac caagctcttt ttctcctcat tgcagtctac   1320
ttcaattatg attatgttga ttatgtgaca tccatgctag aaaatactaa cgtattggat   1380
gttagacttg ggttgaaaaa actagctaat agatgtctta caaaataga tatagaccat   1440
aatcgcaaaa gtagagtcgt aatgaaccgg ttgctacaag taatggctcg agaagttatt   1500
tccaaacaaa aaatttccaa acgaaagatt ctagaagatc cccaggatat tgttatgtt   1560
ctagaagagg caaagggtaa aggatcagct ttaggattat cattggacgt agcagagatc   1620
aaagaattag taataaacaa aaaggctttt aaaaaaatgt gcaatcttct catcttaaaa   1680
gtctttaatg ggacggatcc ccgagatagt aaattgcacg taccagagga gatggagctt   1740
ccatctagca taaggttact acattgggag gcatacccga gaaaatcttt tagatttggt   1800
ccagaaaatc tcgtcacact caacatggag tacagtgagc tcgagaagct atggaagga   1860
actcagccac ttgcaaatct caaggagatg aacttgtgtg ggtcatcttg tttgaaggaa   1920
```

-continued

```
ctcccagatc tttcgaaagc agcaaatctg gagagattgg atgtggctga gtgcaatgct    1980
ttggtagaga ttccatcctc agttgcgaat cttcacaaaa tagttaactt acacatggaa    2040
tcctgtgaaa gtctagaagt cattccaact ctcatcaact tggcatctct taagattatc    2100
aacatacatg attgcccacg gttgaaaagt tttccagatg ttcccaccag cctcgaggaa    2160
cttgtgatag agaaaacagg ggtacaagaa ttgcctgcat catttaggca ttgcactggt    2220
gttactactc tttatatatg ttccaataga aatctcaaga ccttctcaac acatctcccc    2280
atgggtctaa ggaagctaga cctaagcaat tgtggtattg agtgggttac agatagcatc    2340
aaagatcttc ataatctata ttaccttaaa ctatcaggct gcaaaagact tgtgtctttg    2400
ccagaactcc cttgttcgct cgagtgtcta tttgcagagg attgtacatc actagaaaga    2460
gtaagtgact ctctaaacat tccaaatgcg cagttcaatt tcatcaaatg cttcacattg    2520
gatagagaag cacgacgagc gattattcaa caatcgtttg ttcatgggaa tgttatctta    2580
ccagcaagag aagtacttga agaagtcgat taccgagcga gaggaaattg cttaacaatt    2640
cctccttctg ctttcaacag atttaaggtt tgcgttgtgt tgtcaattca ctag          2694
```

<210> SEQ ID NO 2
<211> LENGTH: 897
<212> TYPE: PRT
<213> ORGANISM: Arabidopsis thaliana
<220> FEATURE:
<223> OTHER INFORMATION: Amino acid sequence from HCP6 splice variant 1

<400> SEQUENCE: 2

```
Met Ala Ser Ser Ser Ser Pro Arg Asn Trp Arg Tyr Asn Val Phe
1               5                   10                  15

Thr Ser Phe His Gly Pro Asp Val Arg Ile Lys Phe Leu Ser His Leu
            20                  25                  30

Arg Gln Gln Phe Ile Tyr Asn Gly Ile Thr Met Phe Asp Asp Asn Gly
        35                  40                  45

Ile Glu Arg Ser Gln Ile Ile Ala Pro Ala Leu Lys Lys Ala Ile Gly
    50                  55                  60

Glu Ser Arg Ile Ala Ile Leu Leu Leu Ser Lys Asn Tyr Ala Ser Ser
65                  70                  75                  80

Ser Trp Ser Leu Asp Glu Leu Leu Glu Ile Leu Lys Cys Lys Glu Asp
                85                  90                  95

Ile Gly Gln Ile Val Met Thr Val Phe Tyr Glu Val Asp Pro Ser Asp
            100                 105                 110

Val Arg Asn Gln Thr Gly Asp Phe Gly Ile Ala Phe Lys Glu Thr Cys
        115                 120                 125

Ala His Lys Thr Glu Glu Glu Arg Gln Lys Trp Thr Gln Ala Leu Thr
    130                 135                 140

Tyr Val Gly Asn Ile Ala Gly Glu Asp Phe Lys His Trp Pro Asn Glu
145                 150                 155                 160

Ala Lys Met Ile Glu Lys Ile Ala Arg Asp Val Ser Asp Ile Leu Asn
                165                 170                 175

Val Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
        195                 200                 205

Ile Val Gly Ile Ser Gly Pro Ala Gly Ile Gly Lys Ser Thr Ile Ala
    210                 215                 220
```

```
Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Leu Asp Glu Tyr Arg
            245                 250                 255

Leu Lys Leu His Leu Gln Gln Gln Leu Leu Ala Tyr Val Leu Asn Gln
                260                 265                 270

Asp Lys Ile Arg Val Gly His Leu Ser Val Met Lys Glu Arg Leu Asp
            275                 280                 285

Asp Leu Arg Val Leu Ile Ile Leu Asp Asp Val Glu His Leu Tyr Gln
        290                 295                 300

Leu Glu Ala Leu Ala Asp Ile Arg Trp Phe Gly Pro Gly Ser Arg Val
305                 310                 315                 320

Ile Val Thr Thr Glu Asn Arg Glu Ile Leu Gln His Gly Ile Lys
                325                 330                 335

Asp Ile Tyr His Val Gly Phe Pro Ser Glu Gly Glu Ala Leu Met Ile
                340                 345                 350

Phe Cys Leu Ser Ala Phe Arg Gln Pro Ser Pro Tyr Gly Phe Leu
        355                 360                 365

Lys Leu Thr Tyr Glu Val Ala Ser Ile Cys Gly Asn Leu Pro Leu Gly
    370                 375                 380

Leu His Val Leu Gly Thr Leu Leu Trp Gly Lys Ser Gln Ala Asp Trp
385                 390                 395                 400

Ile Glu Glu Leu Pro Arg Leu Lys Asp Cys Leu Asp Gly Arg Ile Glu
                405                 410                 415

Ser Val Leu Lys Val Gly Tyr Glu Ser Leu Tyr Glu Lys Asp Gln Ala
        420                 425                 430

Leu Phe Leu Leu Ile Ala Val Tyr Phe Asn Tyr Asp Tyr Val Asp Tyr
    435                 440                 445

Val Thr Ser Met Leu Glu Asn Thr Asn Val Leu Asp Val Arg Leu Gly
    450                 455                 460

Leu Lys Lys Leu Ala Asn Arg Cys Leu Ile Gln Ile Asp Ile Asp His
465                 470                 475                 480

Asn Arg Lys Ser Arg Val Val Met Asn Arg Leu Leu Gln Val Met Ala
                485                 490                 495

Arg Glu Val Ile Ser Lys Gln Lys Ile Ser Lys Arg Lys Ile Leu Glu
                500                 505                 510

Asp Pro Gln Asp Ile Cys Tyr Val Leu Glu Glu Ala Lys Gly Lys Gly
        515                 520                 525

Ser Ala Leu Gly Leu Ser Leu Asp Val Ala Glu Ile Lys Glu Leu Val
    530                 535                 540

Ile Asn Lys Lys Ala Phe Lys Met Cys Asn Leu Leu Ile Leu Lys
545                 550                 555                 560

Val Phe Asn Gly Thr Asp Pro Arg Asp Ser Lys Leu His Val Pro Glu
                565                 570                 575

Glu Met Glu Leu Pro Ser Ser Ile Arg Leu Leu His Trp Glu Ala Tyr
        580                 585                 590

Pro Arg Lys Ser Phe Arg Phe Gly Pro Glu Asn Leu Val Thr Leu Asn
    595                 600                 605

Met Glu Tyr Ser Glu Leu Glu Lys Leu Trp Lys Gly Thr Gln Pro Leu
    610                 615                 620

Ala Asn Leu Lys Glu Met Asn Leu Cys Gly Ser Ser Cys Leu Lys Glu
625                 630                 635                 640

Leu Pro Asp Leu Ser Lys Ala Ala Asn Leu Glu Arg Leu Asp Val Ala
```

-continued

```
                    645                 650                 655
Glu Cys Asn Ala Leu Val Glu Ile Pro Ser Ser Val Ala Asn Leu His
                660                 665                 670
Lys Ile Val Asn Leu His Met Glu Ser Cys Glu Ser Leu Glu Val Ile
                675                 680                 685
Pro Thr Leu Ile Asn Leu Ala Ser Leu Lys Ile Ile Asn Ile His Asp
    690                 695                 700
Cys Pro Arg Leu Lys Ser Phe Pro Asp Val Pro Thr Ser Leu Glu Glu
705                 710                 715                 720
Leu Val Ile Glu Lys Thr Gly Val Gln Glu Leu Pro Ala Ser Phe Arg
                725                 730                 735
His Cys Thr Gly Val Thr Thr Leu Tyr Ile Cys Ser Asn Arg Asn Leu
                740                 745                 750
Lys Thr Phe Ser Thr His Leu Pro Met Gly Leu Arg Lys Leu Asp Leu
                755                 760                 765
Ser Asn Cys Gly Ile Glu Trp Val Thr Asp Ser Ile Lys Asp Leu His
770                 775                 780
Asn Leu Tyr Tyr Leu Lys Leu Ser Gly Cys Lys Arg Leu Val Ser Leu
785                 790                 795                 800
Pro Glu Leu Pro Cys Ser Leu Glu Cys Leu Phe Ala Glu Asp Cys Thr
                805                 810                 815
Ser Leu Glu Arg Val Ser Asp Ser Leu Asn Ile Pro Asn Ala Gln Phe
                820                 825                 830
Asn Phe Ile Lys Cys Phe Thr Leu Asp Arg Glu Ala Arg Arg Ala Ile
                835                 840                 845
Ile Gln Gln Ser Phe Val His Gly Asn Val Ile Leu Pro Ala Arg Glu
    850                 855                 860
Val Leu Glu Glu Val Asp Tyr Arg Ala Arg Gly Asn Cys Leu Thr Ile
865                 870                 875                 880
Pro Pro Ser Ala Phe Asn Arg Phe Lys Val Cys Val Val Leu Ser Ile
                885                 890                 895
His
```

<210> SEQ ID NO 3
<211> LENGTH: 3354
<212> TYPE: DNA
<213> ORGANISM: Arabidopsis thaliana
<220> FEATURE:
<221> NAME/KEY: source
<222> LOCATION: 1..3354
<223> OTHER INFORMATION: /organism="Arabidopsis thaliana"
    /note="Nucleotide sequence HCP6 splice variant 2, AT1G56520.2"
    /mol_type="unassigned DNA"

<400> SEQUENCE: 3

```
atggcttctt cttcttcctc acctcgcaac tggagataca atgtcttcac gagcttccat      60
ggaccagacg tccgtattaa atttctcagt catttacgtc aacagtttat ttacaatgga     120
attactatgt tcgatgacaa cgggatcgaa agaagccaaa ttatcgctcc agctctcaaa     180
aaagccattg agaatcgag  gatcgcgatc ttattgctct cgaagaacta tgcttcttcc     240
agttggtctt tggatgagct attggagatt ttaaagtgca agaagatat  agggcaaata     300 gtgatgactg tcttctacga agttgatcct tctgatgtcc gcaaccaaac cggagatttt     360
gggattgctt ttaagaaac  ttgtgctcat aaaacagagg aggagaggca aaatggacc      420 caagctttga cctatgtggg caacattgcc ggagaagact taaacactg  gcccaatgaa     480
```

```
gctaaaatga tcgagaagat tgcaagagat gtttcagata tactaaacgt cacaccgtgt    540
agggattttg atggcatggt tggactaaac gatcatttga gggaaatgga gtctttgcta    600
gatttaaaga atgatggagt taagattgtt ggaatctctg gtcctgcagg cattggtaaa    660
agtaccattg ctacagcttt acatggtcga ctctctaaca tgtttcagcg tacttgtttt    720
gtggacaatc ttagggaaag ctataagatt ggtcttgatg agtatcgttt gaagttgcac    780
ttacaacagc aacttcttgc atatgtttta aatcaggata aaattagggt gggccattta    840
agtgtgatga agaaaggct tgacgacttg agggttctta ttattcttga tgatgtggag     900
catctatatc aactagaggc tttggctgat atcaggtggt ttggtcctgg aagtagggtg    960
atagtgacca ctgaaaacag agagattttg ctgcaacatg gtatcaagga tatataccat   1020
gtgggttttc catcgaagg agaagctcta atgatctttt gtctatctgc ttttagacaa    1080
ccctctccac cttatggttt tttgaagctt acatatgaag ttgcaagtat tgtgggtaat    1140
cttccattgg gtctgcatgt tttggggacg ttattgtggg aaaaagtca ggctgactgg    1200
attgaagaac taccaaggtt gaaagactgt cttgatggaa gaattgagag tgtattgaaa   1260
gttggctatg agagtttata tgagaaagac caagctcttt ttctcctcat tgcagtctac   1320
ttcaattatg attatgttga ttatgtgaca tccatgctag aaaatactaa cgtattggat   1380
gttagacttg ggttgaaaaa actagctaat agatgtctta tacaaataga tatagaccat   1440
aatcgcaaaa gtagagtcgt aatgaaccgg ttgctacaag taatggctcg agaagttatt   1500
tccaaacaaa aaatttccaa acgaaagatt ctagaagatc cccaggatat tgttatgtt    1560
ctagaagagg caagggtaa aggatcagct ttaggattat cattggacgt agcagagatc    1620
aaagaattag taataaacaa aaaggctttt aaaaaaatgt gcaatcttct catcttaaaa   1680
gtctttaatg ggacggatcc ccgagatagt aaattgcacg taccagagga gatggagctt   1740
ccatctagca taaggttact acattgggag gcatacccga gaaaatcttt tagatttggt   1800
ccagaaaatc tcgtcacact caacatggag tacagtgagc tcgagaagct atggaaagga   1860
actcagccac ttgcaaatct caaggagatg aacttgtgtg gtcatcttg tttgaaggaa    1920
ctcccagatc tttcgaaagc agcaaatctg gagagattgg atgtggctga gtgcaatgct   1980
ttggtagaga ttccatcctc agttgcgaat cttcacaaaa tagttaactt acacatggaa   2040
tcctgtgaaa gtctagaagt cattccaact ctcatcaact tggcatctct taagattatc   2100
aacatacatg attgcccacg gttgaaaagt tttccagatg ttcccaccag cctcgaggaa   2160
cttgtgatag agaaaacagg ggtacaagaa ttgcctgcat catttaggca ttgcactggt   2220
gttactactc tttatatatg ttccaataga aatctcaaga ccttctcaac acatctcccc   2280
atgggtctaa ggaagctaga cctaagcaat tgtggtattg agtgggttac agatagcatc   2340
aaagatcttc ataatctata ttaccttaaa ctatcaggct gcaaaagact tgtgtctttg   2400
ccagaactcc cttgttcgct cgagtgtcta tttgcagagg attgtacatc actagaaaga   2460
gtaagtgact ctctaaacat tccaaatgcg cagttcaatt tcatcaaatg cttcacattg   2520
gatagagaag cacgacgagc gattattcaa caatcgtttg ttcatgggaa tgttatctta   2580
ccagcaagag aagtacttga agaagtcgat taccgagcga gaggaaattg cttaacaatt   2640
cctccttctg ctttcaacag atttaaggtt tgcgttgtgt tagtcattgg cgactcagta   2700
aaatccgctt ccgaggattt ccaactacaa accgtctaca cgttccaaac ggaacatgtc   2760
tttatatttg acattagctt cccattaatt tttaatggac gaaagataat gctcaagttc   2820
ttcggtggtt acgctcgcat tattgaatgt ggtgtccaga tcttgatgga cgaaacggac   2880
```

-continued

```
ggaagcaaca aagggttatt tgaaaatgta gaatggcgta catataaatc ctacgaagaa    2940
gcagttgaaa aagaagagta tcaatgggat acaaatcaat ccgaagaaga agaagaagat    3000
gatctatggg atacacatga atccaacgaa gcattcgaca agaagaccaa tgactacgaa    3060
tctgctccca ccgcatatga agacatctgc ttgaatcctt cacctaagct agatccgatt    3120
ccaaatccaa cagcctcatc ttcacggccg ttgtctcgtt ttactttccc agattcggcg    3180
gcggcgtttg ctacccctcg aatagatgat gaagcgtcca ataaagacga caatgaagag    3240
ggagacaaat ctgaaattgt gtccgaagac aaagatgaag ataccgccca cgacggtgac    3300
taccaatcaa tatcaagcaa gttgcttcat atgttatctc tttgcgttaa ttga          3354
```

<210> SEQ ID NO 4
<211> LENGTH: 1117
<212> TYPE: PRT
<213> ORGANISM: Arabidopsis thaliana
<220> FEATURE:
<223> OTHER INFORMATION: Amino acid sequence from HCP6 splice variant 2, AT1G56520.2

<400> SEQUENCE: 4

```
Met Ala Ser Ser Ser Ser Pro Arg Asn Trp Arg Tyr Asn Val Phe
1               5                   10                  15

Thr Ser Phe His Gly Pro Asp Val Arg Ile Lys Phe Leu Ser His Leu
            20                  25                  30

Arg Gln Gln Phe Ile Tyr Asn Gly Ile Thr Met Phe Asp Asp Asn Gly
        35                  40                  45

Ile Glu Arg Ser Gln Ile Ile Ala Pro Ala Leu Lys Lys Ala Ile Gly
    50                  55                  60

Glu Ser Arg Ile Ala Ile Leu Leu Leu Ser Lys Asn Tyr Ala Ser Ser
65                  70                  75                  80

Ser Trp Ser Leu Asp Glu Leu Leu Glu Ile Leu Lys Cys Lys Glu Asp
                85                  90                  95

Ile Gly Gln Ile Val Met Thr Val Phe Tyr Glu Val Asp Pro Ser Asp
            100                 105                 110

Val Arg Asn Gln Thr Gly Asp Phe Gly Ile Ala Phe Lys Glu Thr Cys
        115                 120                 125

Ala His Lys Thr Glu Glu Arg Gln Lys Trp Thr Gln Ala Leu Thr
    130                 135                 140

Tyr Val Gly Asn Ile Ala Gly Glu Asp Phe Lys His Trp Pro Asn Glu
145                 150                 155                 160

Ala Lys Met Ile Glu Lys Ile Ala Arg Asp Val Ser Asp Ile Leu Asn
                165                 170                 175

Val Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
        195                 200                 205

Ile Val Gly Ile Ser Gly Pro Ala Gly Ile Gly Lys Ser Thr Ile Ala
    210                 215                 220

Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Leu Asp Glu Tyr Arg
                245                 250                 255

Leu Lys Leu His Leu Gln Gln Gln Leu Leu Ala Tyr Val Leu Asn Gln
            260                 265                 270
```

-continued

Asp Lys Ile Arg Val Gly His Leu Ser Val Met Lys Glu Arg Leu Asp
275                 280                 285

Asp Leu Arg Val Leu Ile Ile Leu Asp Asp Val Glu His Leu Tyr Gln
290                 295                 300

Leu Glu Ala Leu Ala Asp Ile Arg Trp Phe Gly Pro Gly Ser Arg Val
305                 310                 315                 320

Ile Val Thr Thr Glu Asn Arg Glu Ile Leu Leu Gln His Gly Ile Lys
                325                 330                 335

Asp Ile Tyr His Val Gly Phe Pro Ser Glu Gly Glu Ala Leu Met Ile
                340                 345                 350

Phe Cys Leu Ser Ala Phe Arg Gln Pro Ser Pro Pro Tyr Gly Phe Leu
355                 360                 365

Lys Leu Thr Tyr Glu Val Ala Ser Ile Cys Gly Asn Leu Pro Leu Gly
370                 375                 380

Leu His Val Leu Gly Thr Leu Leu Trp Gly Lys Ser Gln Ala Asp Trp
385                 390                 395                 400

Ile Glu Glu Leu Pro Arg Leu Lys Asp Cys Leu Asp Gly Arg Ile Glu
                405                 410                 415

Ser Val Leu Lys Val Gly Tyr Glu Ser Leu Tyr Glu Lys Asp Gln Ala
                420                 425                 430

Leu Phe Leu Leu Ile Ala Val Tyr Phe Asn Tyr Asp Tyr Val Asp Tyr
            435                 440                 445

Val Thr Ser Met Leu Glu Asn Thr Asn Val Leu Asp Val Arg Leu Gly
            450                 455                 460

Leu Lys Lys Leu Ala Asn Arg Cys Leu Ile Gln Ile Asp Ile Asp His
465                 470                 475                 480

Asn Arg Lys Ser Arg Val Val Met Asn Arg Leu Leu Gln Val Met Ala
                485                 490                 495

Arg Glu Val Ile Ser Lys Gln Lys Ile Ser Lys Arg Lys Ile Leu Glu
                500                 505                 510

Asp Pro Gln Asp Ile Cys Tyr Val Leu Glu Glu Ala Lys Gly Lys Gly
                515                 520                 525

Ser Ala Leu Gly Leu Ser Leu Asp Val Ala Glu Ile Lys Glu Leu Val
530                 535                 540

Ile Asn Lys Lys Ala Phe Lys Lys Met Cys Asn Leu Leu Ile Leu Lys
545                 550                 555                 560

Val Phe Asn Gly Thr Asp Pro Arg Asp Ser Lys Leu His Val Pro Glu
                565                 570                 575

Glu Met Glu Leu Pro Ser Ser Ile Arg Leu Leu His Trp Glu Ala Tyr
                580                 585                 590

Pro Arg Lys Ser Phe Arg Phe Gly Pro Glu Asn Leu Val Thr Leu Asn
            595                 600                 605

Met Glu Tyr Ser Glu Leu Glu Lys Leu Trp Lys Gly Thr Gln Pro Leu
610                 615                 620

Ala Asn Leu Lys Glu Met Asn Leu Cys Gly Ser Ser Cys Leu Lys Glu
625                 630                 635                 640

Leu Pro Asp Leu Ser Lys Ala Ala Asn Leu Glu Arg Leu Asp Val Ala
                645                 650                 655

Glu Cys Asn Ala Leu Val Glu Ile Pro Ser Ser Val Ala Asn Leu His
                660                 665                 670

Lys Ile Val Asn Leu His Met Glu Ser Cys Glu Ser Leu Glu Val Ile
                675                 680                 685

Pro Thr Leu Ile Asn Leu Ala Ser Leu Lys Ile Ile Asn Ile His Asp

-continued

```
            690                 695                 700
Cys Pro Arg Leu Lys Ser Phe Pro Asp Val Pro Thr Ser Leu Glu Glu
705                 710                 715                 720

Leu Val Ile Glu Lys Thr Gly Val Gln Glu Leu Pro Ala Ser Phe Arg
                725                 730                 735

His Cys Thr Gly Val Thr Thr Leu Tyr Ile Cys Ser Asn Arg Asn Leu
                740                 745                 750

Lys Thr Phe Ser Thr His Leu Pro Met Gly Leu Arg Lys Leu Asp Leu
                755                 760                 765

Ser Asn Cys Gly Ile Glu Trp Val Thr Asp Ser Ile Lys Asp Leu His
            770                 775                 780

Asn Leu Tyr Tyr Leu Lys Leu Ser Gly Cys Lys Arg Leu Val Ser Leu
785                 790                 795                 800

Pro Glu Leu Pro Cys Ser Leu Glu Cys Leu Phe Ala Glu Asp Cys Thr
                805                 810                 815

Ser Leu Glu Arg Val Ser Asp Ser Leu Asn Ile Pro Asn Ala Gln Phe
                820                 825                 830

Asn Phe Ile Lys Cys Phe Thr Leu Asp Arg Glu Ala Arg Arg Ala Ile
                835                 840                 845

Ile Gln Gln Ser Phe Val His Gly Asn Val Ile Leu Pro Ala Arg Glu
850                 855                 860

Val Leu Glu Glu Val Asp Tyr Arg Ala Arg Gly Asn Cys Leu Thr Ile
865                 870                 875                 880

Pro Pro Ser Ala Phe Asn Arg Phe Lys Val Cys Val Val Leu Val Ile
                885                 890                 895

Gly Asp Ser Val Lys Ser Ala Ser Glu Asp Phe Gln Leu Gln Thr Val
                900                 905                 910

Tyr Thr Phe Gln Thr Glu His Val Phe Ile Phe Asp Ile Ser Phe Pro
                915                 920                 925

Leu Ile Phe Asn Gly Arg Lys Ile Met Leu Lys Phe Phe Gly Gly Tyr
            930                 935                 940

Ala Arg Ile Ile Glu Cys Gly Val Gln Ile Leu Met Asp Glu Thr Asp
945                 950                 955                 960

Gly Ser Asn Lys Gly Leu Phe Glu Asn Val Glu Trp Arg Thr Tyr Lys
                965                 970                 975

Ser Tyr Glu Glu Ala Val Glu Lys Glu Glu Tyr Gln Trp Asp Thr Asn
                980                 985                 990

Gln Ser Glu Glu Glu Glu Glu Asp Asp Leu Trp Asp Thr His Glu Ser
            995                 1000                1005

Asn Glu Ala Phe Asp Lys Glu Asp His Asp Tyr Glu Ser Ala Pro Thr
            1010                1015                1020

Ala Tyr Glu Asp Ile Cys Leu Asn Pro Ser Pro Lys Leu Asp Pro Ile
1025                1030                1035                1040

Pro Asn Pro Thr Ala Ser Ser Arg Pro Leu Ser Arg Phe Thr Phe
                1045                1050                1055

Pro Asp Ser Ala Ala Ala Phe Ala Thr Pro Arg Ile Asp Asp Glu Ala
                1060                1065                1070

Ser Asn Lys Asp Asp Asn Glu Glu Gly Asp Lys Ser Glu Ile Val Ser
            1075                1080                1085

Glu Asp Lys Asp Glu Asp Thr Ala His Asp Gly Asp Tyr Gln Ser Ile
            1090                1095                1100

Ser Ser Lys Leu Leu His Met Leu Ser Leu Cys Val Asn
1105                1110                1115
```

<210> SEQ ID NO 5
<211> LENGTH: 4311
<212> TYPE: DNA
<213> ORGANISM: Arabidopsis thaliana
<220> FEATURE:
<221> NAME/KEY: source
<222> LOCATION: 1..4311
<223> OTHER INFORMATION: /organism="Arabidopsis thaliana"
    /note="Nucleotide sequence HCP6 genomic sequence (TAIR accession
    number 6530301567)"
    /mol_type="genomic DNA"

<400> SEQUENCE: 5

```
attcttatcc aagactcaaa atctgtgatt ttgaaccact caagatcatc tctcatggct      60
tcttcttctt cctcacctcg caactggaga tacaatgtct tcacgagctt ccatggacca     120
gacgtccgta ttaaatttct cagtcattta cgtcaacagt ttatttacaa tggaattact     180
atgttcgatg acaacgggat cgaaagaagc caaattatcg ctccagctct caaaaaagcc     240
attggagaat cgaggatcgc gatcttattg ctctcgaaga actatgcttc ttccagttgg     300
tctttggatg agctattgga gattttaaag tgcaaagaag atatagggca aatagtgatg     360
actgtcttct acgaagttga tccttctgat gtccgcaacc aaaccggaga ttttgggatt     420
gcttttaaag aaacttgtgc tcataaaaca gaggaggaga ggcaaaaatg gacccaagct     480
ttgacctatg tgggcaacat tgccggagaa gactttaaac actggtttgt atttagttaa     540
gtacagttta tttttcttat gatgaataat ggtgttttat gattttatgt gggatgacat     600
gggttgtgaa gtttggaatt tgattaatct gataaatttg aaactttaa gtatatttga     660 cagggatttt gctatggtat gttatagcgt gtaatgaata ggagtttgat tactatagtt     720
ataaatatca attctttaag tatatttgat caaaatttgt tgtggttcta attactgtta     780
tatttcgtcg ttatgaatat cagatattaa ttaatatctg atattgcatt ctattttaga     840
gtaggtttaa ttgttgaggg gaaccataaa tcggtagtgt ccatgcaagg aaacagagga     900
atggtctctt tatgattttt tctcatgaat tttctttct ttttgttagg cccaatgaag     960
ctaaaatgat cgagaagatt gcaagagatg tttcagatat actaaacgtc acaccgtgta    1020
gggattttga tggcatggtt ggactaaacg atcatttgag ggaaatggag tctttgctag    1080
atttaaagaa tgatggagtt aagattgttg aatctctgg tcctgcaggc attggtaaaa    1140
gtaccattgc tacagcttta catggtcgac tctctaacat gtttcagcgt acttgttttg    1200
tggacaatct tagggaaagc tataagattg gtcttgatga gtatcgtttg aagttgcact    1260
tacaacagca acttcttgca tatgttttaa atcaggataa aattagggtg ggccatttaa    1320
gtgtgatgaa agaaaggctt gacgacttga gggttcttat tattcttgat gatgtggagc    1380
atctatatca actagaggct ttggctgata tcaggtggtt tggtcctgga agtagggtga    1440
tagtgaccac tgaaaacaga gagattttgc tgcaacatgg tatcaaggat atataccatg    1500
tgggttttcc atcagaagga gaagctctaa tgatcttttg tctatctgct tttagacaac    1560
cctctccacc ttatggtttt ttgaagctta catatgaagt tgcaagtatt tgtggtaatc    1620
ttccattggg tctgcatgtt ttgggacgt tattgtgggg aaaaagtcag gctgactgga    1680
ttgaagaact accaaggttg aaagactgtc ttgatggaag aattgagagt gtattgaaag    1740 tggctatga gagttatat gagaaagacc aagctctttt tctcctcatt gcagtctact    1800
tcaattatga ttatgttgat tatgtgacat ccatgctaga aaatactaac gtattggatg    1860
ttagacttgg gttgaaaaaa ctagctaata gatgtcttat acaaatagat atagaccata    1920
```

```
atcgcaaaag tagagtcgta atgaaccggt tgctacaagt aatggctcga gaagttattt    1980
ccaaacaaaa aatttccaaa cgaaagattc tagaagatcc ccaggatatt tgttatgttc    2040
tagaagaggc aaaggtatgt tttcttaatt taaggggtt tgcattactt accatgttat     2100
tgtttgagca tattatctct ggccactaac aagttgtttg aatatttgt tagggtaaag     2160 gatcagcttt aggattatca ttggacgtag cagagatcaa agaattagta ataaacaaaa    2220
aggcttttaa aaaatgtgc aatcttctca tcttaaaagt cttaatggg acggatcccc      2280 gagatagtaa attgcacgta ccagaggaga tggagcttcc atctagcata aggttactac    2340
attgggaggc atacccgaga aaatctttta gatttggtcc agaaaatctc gtcacactca    2400
acatggagta cagtgagctc gagaagctat ggaaaggaac tcaggtaagt tacttacgtg    2460
tgttgatggg aaatgagata tttgatgttg gcaatagtct aatagcacat tttgttctga    2520
ttttcacgtt cagccacttg caaatctcaa ggagatgaac ttgtgtgggt catcttgttt    2580
gaaggaactc ccagatcttt cgaaagcagc aaatctggag agattggatg tggctgagtg    2640
caatgctttg gtagagattc catcctcagt tgcgaatctt cacaaaatag ttaacttaca    2700 catgaatcc tgtgaaagtc tagaagtcat tccaactctc atcaacttgg catctcttaa     2760
gattatcaac atacatgatt gcccacggtt gaaaagtttt ccagatgttc ccaccagcct    2820
cgaggaactt gtgatagaga aaacaggggt acaagaattg cctgcatcat ttaggcattg    2880
cactggtgtt actactcttt atatatgttc aatagaaat ctcaagacct tctcaacaca     2940
tctccccatg ggtctaagga agctagacct aagcaattgt ggtattgagt gggttacaga    3000
tagcatcaaa gatcttcata atctatatta ccttaaacta tcaggctgca aaagacttgt    3060
gtctttgcca gaactccctt gttcgctcga gtgtctattt gcagaggatt gtacatcact    3120
agaaagagta agtgactctc taaacattcc aaatgcgcag ttcaatttca tcaaatgctt    3180
cacattggat agagaagcac gacgagcgat tattcaacaa tcgtttgttc atgggaatgt    3240
tatcttacca gcaagagaag tacttgaaga agtcgattac cgagcgagag gaaattgctt    3300
aacaattcct ccttctgctt tcaacagatt taaggtttgc gttgtgttgt caattcacta    3360
gacgatgtcg aagaattcga gtcttacaaa gcttacgaac taggacttgc atgtcattgc    3420
agagtcattg gcgactcagt aaaatccgct tccgaggatt tccaactaca aaccgtctac    3480
acgttccaaa cggaacatgt ctttatattt gacattagct tcccattaat ttttaatgga    3540
cgaaagataa tgctcaagtt cttcggtggt tacgctcgca ttattgaatg tggtgtccag    3600 atcttgatgac acgaaacgga cggaagcaac aaagggttat ttgaaaatgt agaatggcgt    3660
acatataaat cctacgaaga agcagttgaa aagaagagt atcaatggga tacaaatcaa     3720
tccgaagaag aagaagaaga tgatctatgg gatacacatg aatccaacga agcattcgac    3780
aaagaagacc atgactacga atctgctccc accgcatatg aagacatctg cttgaatcct    3840
tcacctaagc tagatccgat tccaaatcca acagcctcat cttcacggcc gttgtctcgt    3900
tttactttcc cagattcggc ggcggcgttt gctacccctc gaatagatga tgaagcgtcc    3960 aataagacg acaatgaaga gggagacaaa tctgaaattg tgtccgaaga caaagatgaa     4020
gataccgccc acgacggtga ctaccaatca atatcaagca agttgcttca tatgttatct    4080
ctttgcgtta attgatttcg ttaggctatc tacttgtgtg atgaactgat gattctatgc    4140
tttatgtaga cataaactta tttcatgttg cttttgtatt tggcacataa atttttttt     4200 tttaaagaaa tagagacttg tagttgtcaa atttatttca tgtcatgaag tatatttcta    4260
```
tatctctaga tctctctcat gttttgggga aatatatgg aaaaatccct a         4311

<210> SEQ ID NO 6
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
      /note="Nucleotide sequence HCP6 splice variant 1, codon
      optimized"
      /mol_type="unassigned DNA"

<400> SEQUENCE: 6

```
atggctagct ctagctctag tcctaggaac tggcgttata acgtgttcac tagctttcac      60
ggccccgacg ttaggattaa gttccttagt caccttaggc agcagtttat ctataacggg     120
atcactatgt tcgacgataa cgggatcgag cgtagtcaga ttatcgctcc agctcttaag     180
aaggctatcg gcgagtctag gatcgctatc ctgctcctta gtaagaacta cgctagctct     240
agttggtcac tcgacgagct tctcgagatc cttaagtgta agaggatat cggtcagatc      300
gtgatgaccg tgttctacga ggttgaccct agcgacgtta ggaatcagac tggcgatttc     360
gggatcgcct ttaaagagac ttgcgctcac aagaccgaag aggaacgtca aaagtggact     420
caggctctta cctacgtggg taatattgcc ggcgaggact ttaagcactg gcctaacgaa     480
gctaagatga tcgagaagat cgctagggac gttagcgata tccttaacgt gacccctgt     540
agggacttcg acggaatggt tggacttaac gatcaccta gagagatgga atcactcctc     600
gaccttaaga acgacggcgt taagatcgtg ggaattagtg gaccagctgg gatcggtaag     660
tctactattg ctactgcact tcacggtagg cttagtaata tgtttcagag gacctgcttc     720
gtggataacc ttagagagtc ctataagatc ggcctcgacg agtataggct aagcttcac     780
cttcagcagc agctcttggc ctacgtgctt aatcaggata agattagagt gggtcacctt     840
agcgtgatga aggaaaggct cgacgatctt agggtgctga ttattctcga cgacgttgag     900
cacctctatc agcttgaagc tctcgccgat attaggtggt tcggaccagg atctaggtg      960
atcgtgacta ccgagaatag ggaaatcctc cttcagcacg ggattaagga tatctatcac    1020
gtgggcttcc ctagcgaagg tgaggctctt atgatcttct gccttagcgc ttttaggcag    1080
cctagtccac cttacggatt ccttaagctc acctacgaag tggctagtat ctgcggtaac    1140
cttccacttg gacttcacgt gttgggaacc cttttgtggg gtaagagtca ggctgattgg    1200
atcgaggaac tccctaggct taaggattgc ctcgacggta ggattgagtc agttcttaag    1260
gtgggctacg agtcactcta cgagaaggat caggctctct cctcccttat cgccgtttac    1320
tttaactacg actacgttga ctacgtgacc tctatgctcg agaacactaa cgtgctcgac    1380
gttaggctcg gccttaagaa gcttgctaac cgttgcctga ttcagattga tatcgatcac    1440
aaccgtaagt ctagggtggt gatgaatagg ctccttcagg tgatggctag ggaagtgatt    1500
agtaagcaga agattagtaa gcgtaagatc ctcgaggacc ctcaggatat ttgctacgtg    1560
ttggaagagg ctaagggtaa gggatcagct ctcggactta gtcttgacgt ggccgagatt    1620
aaggaactcg tgattaacaa gaaagccttt aagaagatgt gtaacctcct gatccttaaa    1680
gtgtttaacg gcaccgaccc tagggactct aagcttcacg ttccagaaga gatggaactg    1740
cctagctcta ttaggctgct tcactgggag gcttaccta ggaagtcttt tagattcggc     1800
ccagagaacc tcgtgaccct taatatggaa tactcagagc ttgagaagct ctggaaggga    1860
```

| | |
|---|---:|
| actcagccac tcgctaacct taaagagatg aacctctgcg gctctagctg ccttaaagag | 1920 |
| cttccagatc ttagtaaggc cgctaaccct gagaggcttg acgttgcaga gtgtaacgct | 1980 |
| ctcgttgaga tccctagctc agtggctaac cttcacaaga tcgttaacct tcacatggaa | 2040 |
| tcctgcgagt cactcgaggt tatccctacc cttattaacc tcgctagcct taagattatt | 2100 |
| aacattcacg actgccctag acttaagtcc ttcccagatg tgcctactag ccttgaggaa | 2160 |
| ctggtgattg aaaagaccgg cgttcaagag ctgcccgcta gttttagaca ctgtaccggt | 2220 |
| gtgactaccc tctatatctg ctctaaccgt aaccttaaga cctttagcac tcacctccct | 2280 |
| atgggcctta ggaagctcga tcttagtaac tgcggaatcg agtgggtgac cgactctatt | 2340 |
| aaggaccttc acaacctcta ctaccttaag cttagcggct gtaagaggct cgttagcctt | 2400 |
| ccagaacttc cttgctcact tgagtgcctc ttcgctgagg attgcactag tcttgagcgt | 2460 |
| gttagcgact cacttaatat ccctaacgct cagtttaact ttattaagtg cttcacccctc | 2520 |
| gatagggaag ctaggcgtgc tattattcag cagtccttcg ttcacggtaa cgtgatcctt | 2580 |
| ccagctagag aggtgctcga agaggttgac tatagagcta ggggaaactg cctcactatc | 2640 |
| cccctagtg cctttaatag gtttaaggtg tgcgtggtgc tctcaatcca ttaa | 2694 |

<210> SEQ ID NO 7
<211> LENGTH: 3354
<212> TYPE: DNA
<213> ORGANISM: Artificial Sequence
<220> FEATURE:
<221> NAME/KEY: source
<222> LOCATION: 1..3354
<223> OTHER INFORMATION: /organism="Artificial Sequence"
    /note="Nucleotide sequence HCP6 splice variant 2, codon
    optimized"
    /mol_type="unassigned DNA"

<400> SEQUENCE: 7

| | |
|---|---:|
| atggctagct ctagctctag tcctaggaac tggcgttata acgtgttcac tagctttcac | 60 |
| ggcccccacg ttaggattaa gttccttagt caccttaggc agcagtttat ctataacggg | 120 |
| atcactatgt tcgacgataa cgggatcgag cgtagtcaga ttatcgctcc agctcttaag | 180 |
| aaggctatcg gcgagtctag gatcgctatc ctgctcctta gtaagaacta cgctagctct | 240 |
| agttggtcac tcgacgagct tctcgagatc cttaagtgta agaggatat cggtcagatc | 300 |
| gtgatgaccg tgttctacga ggttgaccct agcgacgtta ggaatcagac tggcgatttc | 360 |
| gggatcgcct ttaaagagac ttgcgctcac aagaccgaag aggaacgtca aaagtggact | 420 |
| caggctctta cctacgtggg taatattgcc ggcgaggact ttaagcactg gcctaacgaa | 480 |
| gctaagatga tcgagaagat cgctagggac gttagcgata tccttaacgt gaccccttgt | 540 |
| agggacttcg acggaatggt tggacttaac gatcacctta gagagatgga atcactcctc | 600 |
| gaccttaaga acgacggcgt taagatcgtg ggaattagtg gaccagctgg gatcggtaag | 660 |
| tctactattg ctactgcact tcacggtagg cttagtaata tgtttcagag gacctgcttc | 720 |
| gtggataacc ttagagagtc ctataagatc ggcctcgacg agtataggct taagcttcac | 780 |
| cttcagcagc agctcttggc ctacgtgctt aatcaggata agattagagt gggtcacctt | 840 |
| agcgtgatga aggaaaggct cgacgatctt agggtgctga ttattctcga cgacgttgag | 900 |
| cacctctatc agcttgaagc tctcgccgat attaggtggt tcggaccagg atctagggtg | 960 |
| atcgtgacta ccgagaatag ggaaatcctc cttcagcacg ggattaagga tatctatcac | 1020 |
| gtgggcttcc ctagcgaagg tgaggctctt atgatcttct gccttagcgc ttttaggcag | 1080 |

```
cctagtccac cttacggatt ccttaagctc acctacgaag tggctagtat ctgcggtaac    1140
cttccacttg gacttcacgt gttgggaacc cttttgtggg gtaagagtca ggctgattgg    1200
atcgaggaac tccctaggct taaggattgc ctcgacggta ggattgagtc agttcttaag    1260
gtgggctacg agtcactcta cgagaaggat caggctctct tcctccttat cgccgtttac    1320
tttaactacg actacgttga ctacgtgacc tctatgctcg agaacactaa cgtgctcgac    1380
gttaggctcg gccttaagaa gcttgctaac cgttgcctga ttcagattga tatcgatcac    1440
aaccgtaagt ctagggtggt gatgaatagg ctccttcagg tgatggctag ggaagtgatt    1500
agtaagcaga agattagtaa gcgtaagatc ctcgaggacc ctcaggatat ttgctacgtg    1560
ttggaagagg ctaagggtaa gggatcagct ctcggactta gtcttgacgt ggccgagatt    1620
aaggaactcg tgattaacaa gaaagccttt aagaagatgt gtaacctcct gatccttaaa    1680
gtgtttaacg gcaccgaccc tagggactct aagcttcacg ttccagaaga gatggaactg    1740
cctagctcta ttaggctgct tcactgggag gcttacccta ggaagtcttt tagattcggc    1800
ccagagaacc tcgtgaccct taatatgaaa tactcagagc ttgagaagct ctggaaggga    1860
actcagccac tcgctaacct taaagagatg aacctctgcg gctctagctg ccttaaagag    1920
cttccagatc ttagtaaggc cgctaacctt gagaggcttg acgttgcaga gtgtaacgct    1980
ctcgttgaga tccctagctc agtggctaac cttcacaaga tcgttaacct tcacatggaa    2040
tcctgcgagt cactcgaggt tatccctacc cttattaacc tcgctagcct taagattatt    2100
aacattcacg actgccctag acttaagtcc ttcccagatg tgcctactag ccttgaggaa    2160
ctggtgattg aaaagaccgg cgttcaagag ctgcccgcta gttttagaca ctgtaccggt    2220
gtgactaccc tctatatctg ctctaaccgt aaccttaaga cctttagcac tcacctccct    2280
atgggcctta ggaagctcga tcttagtaac tgcggaatcg agtgggtgac cgactctatt    2340
aaggaccttc acaacctcta ctaccttaag cttagcggct gtaagaggct cgttagcctt    2400
ccagaacttc cttgctcact tgagtgcctc ttcgctgagg attgcactag tcttgagcgt    2460
gttagcgact cacttaatat ccctaacgct cagtttaact ttattaagtg cttcacccctc    2520
gatagggaag ctaggcgtgc tattattcag cagtccttcg ttcacggtaa cgtgatcctt    2580
ccagctagag aggtgctcga agaggttgac tatagagcta ggggaaactg cctcactatc    2640
cccctagtg cctttaatag gtttaaggtg tgcgtggtgc tcgtgatcgg cgactcagtt    2700
aagtcagcta gcgaggactt tcagcttcag accgtttaca cctttcagac cgagcacgtg    2760
ttcatcttcg atattagctt ccccctgatc tttaacggcc gtaagattat gcttaagttc    2820
ttcggcggct acgctaggat tatcgagtgc ggagttcaga tcctgatgga cgaaactgac    2880
ggatctaaca agggcctctt cgagaacgtt gagtggagga cctataagtc ctacgaagag    2940
gccgttgaga agaagagta tcagtgggac actaatcagt ccgaagaaga ggaagaggac    3000
gacctctggg atactcacga atctaacgag gccttcgata aggaagatca cgactacgag    3060
tcagctccta ccgcttacga ggatatctgc cttaacccta gccctaagct cgaccctatt    3120
cctaacccta ccgctagttc tagtaggccc cttagtaggt tcaccttccc agattcagct    3180
gctgctttcg ctactcctag aattgacgac gaggctagta caaggacga taacgaagag    3240
ggcgataagt cagagatcgt tagcgaggat aaggacgagg atactgctca cgacggcgac    3300
tatcagtcta ttagctctaa gttgcttcac atgcttagcc tctgcgttaa ctaa           3354
```

<210> SEQ ID NO 8
<211> LENGTH: 27

```
<212> TYPE: DNA
<213> ORGANISM: Artificial Sequence
<220> FEATURE:
<221> NAME/KEY: source
<222> LOCATION: 1..27
<223> OTHER INFORMATION: /organism="Artificial Sequence"
      /note="HCP6 forward primer"
      /mol_type="unassigned DNA"

<400> SEQUENCE: 8
tgcatggctt cttcttcttc ctcacct                                27

<210> SEQ ID NO 9
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /organism="Artificial Sequence"
      /note="HCP6 reverse primer"
      /mol_type="unassigned DNA"

<400> SEQUENCE: 9
cgcgctagtg aattgacaac acaacg                                 26

<210> SEQ ID NO 10
<211> LENGTH: 55
<212> TYPE: DNA
<213> ORGANISM: Artificial Sequence
<220> FEATURE:
<221> NAME/KEY: source
<222> LOCATION: 1..55
<223> OTHER INFORMATION: /organism="Artificial Sequence"
      /note="HCP6 forward primer (ATG-attB1)"
      /mol_type="unassigned DNA"

<400> SEQUENCE: 10
ggggacaagt ttgtacaaaa aagcaggctc tatggcttct tcttcttcct cacct    55

<210> SEQ ID NO 11
<211> LENGTH: 52
<212> TYPE: DNA
<213> ORGANISM: Artificial Sequence
<220> FEATURE:
<221> NAME/KEY: source
<222> LOCATION: 1..52
<223> OTHER INFORMATION: /organism="Artificial Sequence"
      /note="HCP6 reverse primer (stop-attB2)"
      /mol_type="unassigned DNA"

<400> SEQUENCE: 11
ggggaccact ttgtacaaga aagctgggtc ctagtgaatt gacaacacaa cg       52

<210> SEQ ID NO 12
<211> LENGTH: 2691
<212> TYPE: DNA
<213> ORGANISM: Artificial Sequence
<220> FEATURE:
<221> NAME/KEY: source
<222> LOCATION: 1..2691
<223> OTHER INFORMATION: /organism="Artificial Sequence"
      /note="Nucleotide sequence HCP6, variant 1"
      /mol_type="unassigned DNA"

<400> SEQUENCE: 12
atgatgagca gcagctgcag ccccagaaac tggagataca acgtgttcac cagcttccac    60
ggccccgacg tgagaatcca ctgggcagc agaatgagaa acaactgggc ctacaacatc    120
```

```
atctgcatgt acgaggagca gatcctggac aagagccaga tcatgatgcc cgccctgaag    180
agagccgccg gcgagaccaa gctggccggc atgctgatgt gcaagaacta cgccaccagc    240
agcttctgcg ccgacgagat gctggagggc ctgaagagca aggacgagct ggcccagatc    300
gtgatgacca tctactacga gctggagccc tgcgacctgc accagaacag catcgagttc    360
ggcatcgcct tcaaggagac ctgcgcccac aagaccgagg aggagagaca gaagtggacc    420
caggccctga cctacgtggg caacatcgcc ggcgacgact ccaccacta ccccccaggag   480 gccaagctgg ccgaccacat catcagagac gtgaccgaca tcgcccaggc cacccccctgc  540 agagacttcg acggcatggt gggcctgaac gaccacctga gagagatgga gagcctgctg    600
gacctgaaga cgacggcgt gaagatcgtg ggcatcagcg gccccgccgg catcggcaag     660
agcaccatcg ccaccgccct gcacggcaga ctgagcaaca tgttccagag aacctgcttc    720
gtggacaacc tgagagagag ctacaagatc ggcggcgagg agttcaagct gaaggtgaga    780
atccagcagc agggcctggg ctacctgggc cagcaggacc acggcagagt ggccaagatc    840
accgccggca aggagagagg cgacgacgcc agaggcgtga tgatcatcga cgacgtggac    900
aagatgttcc agatggaggc cgtggccgag atcagatact tcggccccct gtgccacggc    960
atgctgagca ccgagaacca cgagatgctg atcaaccacg catcagaga ggcctggaga    1020 gtggcctacc ccagcgacgt ggacgccctg gtggtgtggt gcggctgcgc cttcagaaac   1080
cccagccccc cctacatgta catgaaggtg accttcgacg tggtgaccgt gaccctgcag    1140
ctgcccggcg cgccacat catggtgacc ctgatgtggg cagatgcaa cgccgactgg     1200 atcgaggagc tgcccagact gaaggactgc ctggacggca gaatcgagag cgtgctgaag    1260
gtgggctacg agagcctgta cgagaaggac caggccctgt cctgctgat cgccgtgtac    1320 ttcaactacg actacgtgga ctacgtgacc agcatgctgg agaacaccaa cgtgctggac    1380
gtgcacggcg tgggccacaa gctgatgcag cacagcggcg cccagatcga gatcgaccac    1440
cagagaagat gcagaatcgt gatgcagaga ctgctgcaga tgatggccaa ggacctgatc    1500
agcaagaaca gaatcagcag aagaaagatc atcgacgacc ccaacgagct gaccttcgtg    1560
ctggacgacg tgagactgaa gggcagcatc ctggccatga ccatggagat cgtggaggtg    1620
agagacatcg gcatccagag aaaggccttc agaaagatct gccagggcgt gctggtgaag    1680
gtgtacaaca tgagcgaccc cagagagtgc agactgcacg tgcccgacga cggcgacctg    1740
cccaccagca tcagactgat gagattcgac gcctaccccc acaagagcta cagatggggc    1800
cccgagaacc tggtgaccct gaacatggag tacagcgagc tggagaagct gtggaagggc    1860
acccagcccc tggccaacct gaaggagatg aacctgtgcg gcagcagctg cctgaaggag    1920
ctgcccgacc tgagcaaggc cgccaacctg gagagactgg acgtggccga gtgcaacgcc    1980
ctggtggaga tccccagcag cgtggccaac ctgcacaaga tcgtgaacct gcacatggag    2040
agctgcgaga gcctggaggt gatccccacc ctgatcaacc tggccagcct gaagatcatc    2100
aacatccacg actgccccag actgaagagc ttccccgacg tgcccaccag cctggaggag    2160
ctggtgatcg agaagaccgg cgtgcaggag ctgccgcca gcttcagaca ctgcaccggc    2220
gtgaccaccc tgtacatctg cagcaacaga aacctgaaga ccttcagcac ccacctgccc    2280
atgggcctga aaagctgga cctgagcaac tgcggcatcg agtgggtgac cgacagcatc    2340
aaggacctgc acaacctgta cacctgaag ctgagcggct gcaagagact ggtgagcctg    2400
cccgagctgc cctgcagcct ggagtgcctg ttcgccgagg actgcaccag cctggagaga    2460
gtgagcgaca gcctgaacat ccccaacgcc cagttcaact tcatgcactg ctactgcggc    2520
```

-continued

```
gagagagagg ccaagcacat gctgatgaac aacagctggg tgcacggcaa catcgccatg   2580
cccgccagag acatcctgga ggacgtggag tacaaggcca aggccagtg cctgagcgtg    2640 ccccccacca tctaccagca cttcagaatg tgcggcgtgg gcaccatcca c            2691
```

<210> SEQ ID NO 13
<211> LENGTH: 897
<212> TYPE: PRT
<213> ORGANISM: Artificial Sequence
<220> FEATURE:
<223> OTHER INFORMATION: Amino acid sequence HCP6, variant 1

<400> SEQUENCE: 13

```
Met Met Ser Ser Cys Ser Pro Arg Asn Trp Arg Tyr Asn Val Phe
1               5                  10                  15

Thr Ser Phe His Gly Pro Asp Val Arg Ile His Trp Gly Ser Arg Met
            20                  25                  30

Arg Asn Asn Trp Ala Tyr Asn Ile Ile Cys Met Tyr Glu Glu Gln Ile
        35                  40                  45

Leu Asp Lys Ser Gln Ile Met Met Pro Ala Leu Lys Arg Ala Ala Gly
    50                  55                  60

Glu Thr Lys Leu Ala Gly Met Leu Met Cys Lys Asn Tyr Ala Thr Ser
65                  70                  75                  80

Ser Phe Cys Ala Asp Glu Met Leu Glu Gly Leu Lys Ser Lys Asp Glu
                85                  90                  95

Leu Ala Gln Ile Val Met Thr Ile Tyr Tyr Glu Leu Glu Pro Cys Asp
            100                 105                 110

Leu His Gln Asn Ser Ile Glu Phe Gly Ile Ala Phe Lys Glu Thr Cys
        115                 120                 125

Ala His Lys Thr Glu Glu Glu Arg Gln Lys Trp Thr Gln Ala Leu Thr
    130                 135                 140

Tyr Val Gly Asn Ile Ala Gly Asp Asp Phe His His Tyr Pro Gln Glu
145                 150                 155                 160

Ala Lys Leu Ala Asp His Ile Ile Arg Asp Val Thr Asp Ile Ala Gln
                165                 170                 175

Ala Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
        195                 200                 205

Ile Val Gly Ile Ser Gly Pro Ala Gly Ile Gly Lys Ser Thr Ile Ala
    210                 215                 220

Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Gly Glu Glu Phe Lys
                245                 250                 255

Leu Lys Val Arg Ile Gln Gln Gln Gly Leu Gly Tyr Leu Gly Gln Gln
            260                 265                 270

Asp His Gly Arg Val Ala Lys Ile Thr Ala Gly Lys Glu Arg Gly Asp
        275                 280                 285

Asp Ala Arg Gly Val Met Ile Ile Asp Asp Val Asp Lys Met Phe Gln
    290                 295                 300

Met Glu Ala Val Ala Glu Ile Arg Tyr Phe Gly Pro Leu Cys His Gly
305                 310                 315                 320

Met Leu Ser Thr Glu Asn His Glu Met Leu Ile Asn His Gly Ile Arg
                325                 330                 335
```

-continued

```
Glu Ala Trp Arg Val Ala Tyr Pro Ser Asp Val Asp Ala Leu Val Val
                340                 345                 350
Trp Cys Gly Cys Ala Phe Arg Asn Pro Ser Pro Pro Tyr Met Tyr Met
                355                 360                 365
Lys Val Thr Phe Asp Val Thr Val Thr Leu Gln Leu Pro Gly Gly
        370                 375                 380
Ala His Ile Met Val Thr Leu Met Trp Gly Arg Cys Asn Ala Asp Trp
385                 390                 395                 400
Ile Glu Glu Leu Pro Arg Leu Lys Asp Cys Leu Asp Gly Arg Ile Glu
                405                 410                 415
Ser Val Leu Lys Val Gly Tyr Glu Ser Leu Tyr Glu Lys Asp Gln Ala
                420                 425                 430
Leu Phe Leu Leu Ile Ala Val Tyr Phe Asn Tyr Asp Tyr Val Asp Tyr
        435                 440                 445
Val Thr Ser Met Leu Glu Asn Thr Asn Val Leu Asp Val His Gly Val
        450                 455                 460
Gly His Lys Leu Met Gln His Ser Gly Ala Gln Ile Glu Ile Asp His
465                 470                 475                 480
Gln Arg Arg Cys Arg Ile Val Met Gln Arg Leu Leu Gln Met Met Ala
                485                 490                 495
Lys Asp Leu Ile Ser Lys Asn Arg Ile Ser Arg Arg Lys Ile Ile Asp
                500                 505                 510
Asp Pro Asn Glu Leu Thr Phe Val Leu Asp Asp Val Arg Leu Lys Gly
        515                 520                 525
Ser Ile Leu Ala Met Thr Met Glu Ile Val Glu Val Arg Asp Ile Gly
        530                 535                 540
Ile Gln Arg Lys Ala Phe Arg Lys Ile Cys Gln Gly Val Leu Val Lys
545                 550                 555                 560
Val Tyr Asn Met Ser Asp Pro Arg Glu Cys Arg Leu His Val Pro Asp
                565                 570                 575
Asp Gly Asp Leu Pro Thr Ser Ile Arg Leu Met Arg Phe Asp Ala Tyr
                580                 585                 590
Pro His Lys Ser Tyr Arg Trp Gly Pro Glu Asn Leu Val Thr Leu Asn
        595                 600                 605
Met Glu Tyr Ser Glu Leu Glu Lys Leu Trp Lys Gly Thr Gln Pro Leu
        610                 615                 620
Ala Asn Leu Lys Glu Met Asn Leu Cys Gly Ser Ser Cys Leu Lys Glu
625                 630                 635                 640
Leu Pro Asp Leu Ser Lys Ala Ala Asn Leu Glu Arg Leu Asp Val Ala
                645                 650                 655
Glu Cys Asn Ala Leu Val Glu Ile Pro Ser Ser Val Ala Asn Leu His
                660                 665                 670
Lys Ile Val Asn Leu His Met Glu Ser Cys Glu Ser Leu Glu Val Ile
        675                 680                 685
Pro Thr Leu Ile Asn Leu Ala Ser Leu Lys Ile Ile Asn Ile His Asp
        690                 695                 700
Cys Pro Arg Leu Lys Ser Phe Pro Asp Val Pro Thr Ser Leu Glu Glu
705                 710                 715                 720
Leu Val Ile Glu Lys Thr Gly Val Gln Glu Leu Pro Ala Ser Phe Arg
                725                 730                 735
His Cys Thr Gly Val Thr Thr Leu Tyr Ile Cys Ser Asn Arg Asn Leu
        740                 745                 750
```

| | | | | | | | | | | |
|---|---|---|---|---|---|---|---|---|---|---|
| Lys | Thr | Phe | Ser | Thr | His | Leu | Pro | Met | Gly | Leu | Arg | Lys | Leu | Asp | Leu |
| | | | 755 | | | | 760 | | | | 765 | | | | |
| Ser | Asn | Cys | Gly | Ile | Glu | Trp | Val | Thr | Asp | Ser | Ile | Lys | Asp | Leu | His |
| | 770 | | | | | 775 | | | | | 780 | | | | |
| Asn | Leu | Tyr | Tyr | Leu | Lys | Leu | Ser | Gly | Cys | Lys | Arg | Leu | Val | Ser | Leu |
| 785 | | | | | 790 | | | | | 795 | | | | | 800 |
| Pro | Glu | Leu | Pro | Cys | Ser | Leu | Glu | Cys | Leu | Phe | Ala | Glu | Asp | Cys | Thr |
| | | | | 805 | | | | | 810 | | | | | 815 | |
| Ser | Leu | Glu | Arg | Val | Ser | Asp | Ser | Leu | Asn | Ile | Pro | Asn | Ala | Gln | Phe |
| | | | 820 | | | | | 825 | | | | | 830 | | |
| Asn | Phe | Met | His | Cys | Tyr | Cys | Gly | Glu | Arg | Glu | Ala | Lys | His | Met | Leu |
| | | 835 | | | | | 840 | | | | | 845 | | | |
| Met | Asn | Asn | Ser | Trp | Val | His | Gly | Asn | Ile | Ala | Met | Pro | Ala | Arg | Asp |
| | 850 | | | | | 855 | | | | | 860 | | | | |
| Ile | Leu | Glu | Asp | Val | Glu | Tyr | Lys | Ala | Arg | Gly | Gln | Cys | Leu | Ser | Val |
| 865 | | | | | 870 | | | | | 875 | | | | | 880 |
| Pro | Pro | Thr | Ile | Tyr | Gln | His | Phe | Arg | Met | Cys | Gly | Val | Gly | Thr | Ile |
| | | | | 885 | | | | | 890 | | | | | 895 | |
| His | | | | | | | | | | | | | | | |

<210> SEQ ID NO 14
<211> LENGTH: 2691
<212> TYPE: DNA
<213> ORGANISM: Artificial Sequence
<220> FEATURE:
<221> NAME/KEY: source
<222> LOCATION: 1..2691
<223> OTHER INFORMATION: /organism="Artificial Sequence"
    /note="Nucleotide sequence HCP6, variant 2"
    /mol_type="unassigned DNA"

<400> SEQUENCE: 14

```
atggccagct gctgcaccag ccccagaaac tggagataca acgtgttcac cagcttccac      60
ggccccgacg tgagaatcaa gttcctgagc cacggcagaa accagtgggt gttcaacggc     120
ggctgcatgt acgacgacaa cctgatcgac agatgcaaca tcatgctgcc cgccctgaag     180
cacgccctgg gcgactgcaa gatcgtgatc ctgctggtga ccaagaactt cggcacctgc     240
tgctactgcg cgacgacgt gatcgagctg atgagatgca aggaggaggg cggcaacgtg     300
gtgatgtgcg gcttctggga gctggacccc agcgagatgc acaacaacac cctggagttc     360
ggcatcgcct tcaaggagac ctgcgcccac aagaccgagg aggagagaca gaagtggacc     420
caggccctga cctacgtggg caacatcgcc ggcgaggact tcaagcactg cccaacgag     480
gccaagatgc tggacagaat gatgagagag atcagcgaga tcgtgcaggt gagcccctgc     540
agagacttcg acggcatggt gggcctgaac gaccacctga gagagatgga gagcctgctg     600
gacctgaaga cgacggcgt gaagatcgtg ggcatcagcg cccgccgg catcggcaag     660
agcaccatcg ccaccgccct gcacggcaga ctgagcaaca tgttccagag aacctgcttc     720
gtggacaacc tgagagagag ctacaagatc ggcctggacg agtacagact gaagctgcac     780
ctgcagcagc agctgctggc ctacgtgctg aaccaggaca agatcagagt gggccacctg     840
agcgtgatga aggagagact ggacgacctg agagtgctga tcatcctgga cgacgtggag     900
cacctgtacc agctggaggc cctggccgac atcagatggt tcggccccgg cagcagagtg     960
atcgtgacca ccgagaacag agagatcctg ctgcagcacg gcatcaagga catctaccac    1020
gtgggcttcc ccagcgaggg cgaggccctg atgatcttct gcctgagcgc cttcagacag    1080
```

```
cccacccccc cctggggctt cgccagagtg accttcgagg tgctgagcct gtgcatgaac      1140
atgcccctgg gcatccacct gggcggctgc atcgtgtgga tgcactgcaa cgccgactgg      1200
atcgacgaca tccccagaat gagagagacc atggacggcc acctggagag cgccgtgaag      1260
gtgggctacg agagcctgta cgagaaggac caggccctgt tcctgctgat cgccgtgtac      1320
ttcaactacg actacgtgga ctacgtgacc agcatgctgg agaacaccaa cgtgctggac      1380
gtgcacctgg tgctgcacca cgccgtgcag aagaccctgg ccaggccga ggccgaccac       1440
cagagacact gcaagatcat cgcccagcac ggcctgaacg catcctgag agaggtgatc       1500
accaagaacc acatcagcag acacaagatc gtggaggagc cccaggacat gacctgggtg      1560
ctggacgagg gcaagggcag agtgtgcatg ctgatgctga ccctggacat catggacatg      1620
agagaggccg gcatccagca caagctgttc aagaagatga ccaacctgat catgctgcac      1680
ctgtaccagg gcagcgaccc cagagagtgc aagctgagaa tccccgacga gatggaggtg      1740
ccctgctgcg tgaagggcgg ccactacgag gtgtaccccc acaagtgctt ccactacggc      1800
cccgagaacc tggtgaccct gaacatggag tacagcgagc tggagaagct gtggaagggc      1860
acccagcccc tggccaacct gaaggagatg aacctgtgcg gcagcagctg cctgaaggag      1920
ctgcccgacc tgagcaaggc cgccaacctg agagactgg acgtggccga gtgcaacgcc       1980
ctggtggaga tccccagcag cgtggccaac ctgcacaaga tcgtgaacct gcacatggag      2040
agctgcgaga gcctggaggt gatccccacc ctgatcaacc tggccagcct gaagatcatc      2100
aacatccacg actgccccag actgaagagc ttccccgacg tgcccaccag cctggaggag      2160
ctggtgatcg agaagaccgg cgtgcaggag ctgcccgcca gcttcagaca ctgcaccggc      2220
gtgaccaccc tgtacatctg cagcaacaga aacctgaaga ccttcagcac ccacctgccc      2280
atgggcctga aaagctgga cctgagcaac tgcggcatcg agtgggtgac cgacagcatc      2340
aaggacctgc acaacctgta ctacctgaag ctgagcggct gcaagagact ggtgagcctg      2400
cccgagctgc cctgcagcct ggagtgcctg ttcgccgagg actgcaccag cctggagaga      2460
gtgagcgaca gcctgaacat ccccaacgcc cagttccagt cgtgagaaac ctggtgcctg      2520
gagagagacg tgaagaagat catcatcaac cagacctggg ccacggcaa catggccggc       2580
cccgccagag acctgatgga ggagggcgac tggcacggca gggccagag cctgagcatc       2640
ccccctgcc tgtacaacaa gtggcacatc agcgtggtga tcaccatcag a               2691
```

<210> SEQ ID NO 15
<211> LENGTH: 897
<212> TYPE: PRT
<213> ORGANISM: Artificial Sequence
<220> FEATURE:
<223> OTHER INFORMATION: Amino acid sequence HCP6, variant 2

<400> SEQUENCE: 15

```
Met Ala Ser Cys Cys Thr Ser Pro Arg Asn Trp Arg Tyr Asn Val Phe
1               5                   10                  15

Thr Ser Phe His Gly Pro Asp Val Arg Ile Lys Phe Leu Ser His Gly
            20                  25                  30

Arg Asn Gln Trp Val Phe Asn Gly Gly Cys Met Tyr Asp Asp Asn Leu
        35                  40                  45

Ile Asp Arg Cys Asn Ile Met Leu Pro Ala Leu Lys His Ala Leu Gly
    50                  55                  60

Asp Cys Lys Ile Val Ile Leu Leu Val Thr Lys Asn Phe Gly Thr Cys
65                  70                  75                  80
```

-continued

```
Cys Tyr Cys Gly Asp Val Ile Glu Leu Met Arg Cys Lys Glu Glu
             85                  90                  95
Gly Gly Asn Val Val Met Cys Gly Phe Trp Glu Leu Asp Pro Ser Glu
            100                 105                 110
Met His Asn Asn Thr Leu Glu Phe Gly Ile Ala Phe Lys Glu Thr Cys
            115                 120                 125
Ala His Lys Thr Glu Glu Arg Gln Lys Trp Thr Gln Ala Leu Thr
        130                 135                 140
Tyr Val Gly Asn Ile Ala Gly Glu Asp Phe Lys His Trp Pro Asn Glu
145                 150                 155                 160
Ala Lys Met Leu Asp Arg Met Met Arg Glu Ile Ser Glu Ile Val Gln
                165                 170                 175
Val Ser Pro Cys Arg Asp Phe Asp Gly Met Val Gly Leu Asn Asp His
            180                 185                 190
Leu Arg Glu Met Glu Ser Leu Leu Asp Leu Lys Asn Asp Gly Val Lys
        195                 200                 205
Ile Val Gly Ile Ser Gly Pro Ala Gly Ile Gly Lys Ser Thr Ile Ala
        210                 215                 220
Thr Ala Leu His Gly Arg Leu Ser Asn Met Phe Gln Arg Thr Cys Phe
225                 230                 235                 240
Val Asp Asn Leu Arg Glu Ser Tyr Lys Ile Gly Leu Asp Glu Tyr Arg
                245                 250                 255
Leu Lys Leu His Leu Gln Gln Gln Leu Leu Ala Tyr Val Leu Asn Gln
            260                 265                 270
Asp Lys Ile Arg Val Gly His Leu Ser Val Met Lys Glu Arg Leu Asp
        275                 280                 285
Asp Leu Arg Val Leu Ile Ile Leu Asp Asp Val Glu His Leu Tyr Gln
        290                 295                 300
Leu Glu Ala Leu Ala Asp Ile Arg Trp Phe Gly Pro Gly Ser Arg Val
305                 310                 315                 320
Ile Val Thr Thr Glu Asn Arg Glu Ile Leu Leu Gln His Gly Ile Lys
                325                 330                 335
Asp Ile Tyr His Val Gly Phe Pro Ser Glu Gly Glu Ala Leu Met Ile
            340                 345                 350
Phe Cys Leu Ser Ala Phe Arg Gln Pro Thr Pro Pro Trp Gly Phe Ala
        355                 360                 365
Arg Val Thr Phe Glu Val Leu Ser Leu Cys Met Asn Met Pro Leu Gly
        370                 375                 380
Ile His Leu Gly Gly Cys Ile Val Trp Met His Cys Asn Ala Asp Trp
385                 390                 395                 400
Ile Asp Asp Ile Pro Arg Met Arg Glu Thr Met Asp Gly His Leu Glu
                405                 410                 415
Ser Ala Val Lys Val Gly Tyr Glu Ser Leu Tyr Glu Lys Asp Gln Ala
            420                 425                 430
Leu Phe Leu Leu Ile Ala Val Tyr Phe Asn Tyr Asp Tyr Val Asp Tyr
        435                 440                 445
Val Thr Ser Met Leu Glu Asn Thr Asn Val Leu Asp Val His Leu Val
        450                 455                 460
Leu His His Ala Val Gln Lys Thr Leu Gly Gln Ala Glu Ala Asp His
465                 470                 475                 480
Gln Arg His Cys Lys Ile Ile Ala Gln His Gly Leu Asn Gly Ile Leu
                485                 490                 495
Arg Glu Val Ile Thr Lys Asn His Ile Ser Arg His Lys Ile Val Glu
```

```
                    500                 505                 510
Glu Pro Gln Asp Met Thr Trp Val Leu Asp Glu Gly Lys Gly Arg Val
            515                 520                 525
Cys Met Leu Met Leu Thr Leu Asp Ile Met Asp Met Arg Glu Ala Gly
            530                 535                 540
Ile Gln His Lys Leu Phe Lys Lys Met Thr Asn Leu Ile Met Leu His
545                 550                 555                 560
Leu Tyr Gln Gly Ser Asp Pro Arg Glu Cys Lys Leu Arg Ile Pro Asp
            565                 570                 575
Glu Met Glu Val Pro Cys Cys Val Lys Gly His Tyr Glu Val Tyr
            580                 585                 590
Pro His Lys Cys Phe His Tyr Gly Pro Glu Asn Leu Val Thr Leu Asn
            595                 600                 605
Met Glu Tyr Ser Glu Leu Glu Lys Leu Trp Lys Gly Thr Gln Pro Leu
            610                 615                 620
Ala Asn Leu Lys Glu Met Asn Leu Cys Gly Ser Ser Cys Leu Lys Glu
625                 630                 635                 640
Leu Pro Asp Leu Ser Lys Ala Ala Asn Leu Glu Arg Leu Asp Val Ala
            645                 650                 655
Glu Cys Asn Ala Leu Val Glu Ile Pro Ser Ser Val Ala Asn Leu His
            660                 665                 670
Lys Ile Val Asn Leu His Met Glu Ser Cys Glu Ser Leu Glu Val Ile
            675                 680                 685
Pro Thr Leu Ile Asn Leu Ala Ser Leu Lys Ile Ile Asn Ile His Asp
            690                 695                 700
Cys Pro Arg Leu Lys Ser Phe Pro Asp Val Pro Thr Ser Leu Glu Glu
705                 710                 715                 720
Leu Val Ile Glu Lys Thr Gly Val Gln Glu Leu Pro Ala Ser Phe Arg
            725                 730                 735
His Cys Thr Gly Val Thr Thr Leu Tyr Ile Cys Ser Asn Arg Asn Leu
            740                 745                 750
Lys Thr Phe Ser Thr His Leu Pro Met Gly Leu Arg Lys Leu Asp Leu
            755                 760                 765
Ser Asn Cys Gly Ile Glu Trp Val Thr Asp Ser Ile Lys Asp Leu His
770                 775                 780
Asn Leu Tyr Tyr Leu Lys Leu Ser Gly Cys Lys Arg Leu Val Ser Leu
785                 790                 795                 800
Pro Glu Leu Pro Cys Ser Leu Glu Cys Leu Phe Ala Glu Asp Cys Thr
            805                 810                 815
Ser Leu Glu Arg Val Ser Asp Ser Leu Asn Ile Pro Asn Ala Gln Phe
            820                 825                 830
Gln Phe Val Arg Thr Trp Cys Leu Glu Arg Asp Val Lys Lys Ile Ile
            835                 840                 845
Ile Asn Gln Thr Trp Gly His Gly Asn Met Ala Gly Pro Ala Arg Asp
            850                 855                 860
Leu Met Glu Glu Gly Asp Trp His Gly Arg Gly Gln Ser Leu Ser Ile
865                 870                 875                 880
Pro Pro Cys Leu Tyr Asn Lys Trp His Ile Ser Val Val Ile Thr Ile
            885                 890                 895
Arg

<210> SEQ ID NO 16
<211> LENGTH: 2691
```

```
<212> TYPE: DNA
<213> ORGANISM: Artificial Sequence
<220> FEATURE:
<221> NAME/KEY: source
<222> LOCATION: 1..2691
<223> OTHER INFORMATION: /organism="Artificial Sequence"
      /note="Nucleotide sequence HCP6, variant 3"
      /mol_type="unassigned DNA"

<400> SEQUENCE: 16
```

| | | | | |
|---|---|---|---|---|
| atggcctgca | ccagcaccag | ccccacaac | tggagataca | acgtgttcac cagcttccac | 60 |
| ggccccgacg | tgagaatcag | attcatgtgc | aagctgagac | agcagttcat ctaccagggc | 120 |
| atcaccatgt | gggacgacaa | cggcatcgag | agaagccaga | tcatcgcccc catcctgaga | 180 |
| agactggccg | gcgagagcag | aatcgtgatc | atgctgctga | ccaagaacta cgccagcagc | 240 |
| agctacagcc | tggacgagct | gctggagatc | ctgaagtgca | aggacgacat catcaacatc | 300 |
| gccggcaccg | tgttctggga | gatggagccc | agcgaggtga | aaaccagac cgccgacttc | 360 |
| ggcatcgcct | tcaaggagac | ctgcgcccac | aagaccgagg | aggagagaca gaagtggacc | 420 |
| caggccctga | cctacgtggg | caacatcgcc | ggcgaggact | tcaagagatg cccaacgag | 480 |
| ggcagaatga | tcgagcacat | catgagagac | ggcagcgagc | tggtgcagat cacccccctgc | 540 |
| agagacttcg | acggcatggt | gggcctgaac | gaccacctga | gagagatgga gagcctgctg | 600 |
| gacctgaaga | cgacggcgt | gaagatcgtg | ggcatcagcg | ccccgccgg catcggcaag | 660 |
| agcaccatcg | ccaccgccct | gcacggcaga | ctgagcaaca | tgttccagag aacctgcttc | 720 |
| gtggacaacc | tgagagagag | ctacaagatc | ggcctggagg | agtggagaat caagctgcac | 780 |
| gcccagaacc | agatgatcat | cttcgtgatc | cagaacgaca | gatcagagt ggtgagaatg | 840 |
| accgtgatga | aggacaagct | ggaggagctg | aagatcgcca | tcgtgctgga cgaggtggag | 900 |
| aagctgtaca | acatcgaggt | gctgatggac | atcagatggt | tcggcccgg cagccacatg | 960 |
| gtggtgacca | ccgacaacag | agagatcctg | ctgcagaagc | tggccaagga catcttccac | 1020 |
| gtgctgtacc | ccagcgaggg | cgaggccctg | ggcatctggt | gcatgagcgt gttcaagaac | 1080 |
| cccagccccc | cctacggctt | catcaagatg | acctacgaca | tggtgagcat ctgcatcaac | 1140 |
| ctgcccatca | tggtgcacgt | gctgggcagc | ctgctgtggg | gcagaaccca ggccgagtgg | 1200 |
| atcgaggagc | tgcccagact | gaaggactgc | ctgacggca | gaatcgagag cgtgctgaag | 1260 |
| gtgggctacg | agagcctgta | cgagaaggac | caggccctgt | tcctgctgat cgccgtgtac | 1320 |
| ttcaactacg | actacgtgga | ctacgtgacc | agcatgctgg | agaacaccaa cgtgctggac | 1380 |
| gtgaagctgg | gcctgaagaa | gggcggccag | agaaccctga | tcaacgccga catcgaccac | 1440 |
| aacagaaagt | gcagagtggt | gatgaacaga | atgctgaacg | tgatcgtgaa ggaggtgatc | 1500 |
| tgcaagcaga | gatcagcaa | gagaaagatc | ctggacgacc | cccaggagat ctgcttcctg | 1560 |
| ctggaggagg | ccaagctgaa | gatcagcgcc | gtgggcctgt | gcctggagat ggccgacatc | 1620 |
| cacgacctgg | tggcccagaa | gaaggcctgg | aagaagatgt | gcaacctgct gatcgtgcac | 1680 |
| gtgtggaacg | gcaccgagcc | caaggagagc | agactgcaca | tccccgacga ggccgagatc | 1740 |
| ccctgcacca | tcagactgat | ccactgggag | gtgtaccccc | acagaagctt cagattcggc | 1800 |
| cccgagaacc | tggtgaccct | gaacatggag | tacagcgagc | tggagaagct gtggaagggc | 1860 |
| acccagcccc | tggccaacct | gaaggagatg | aacctgtgcg | gcagcagctg cctgaaggag | 1920 |
| ctgcccgacc | tgagcaaggc | cgccaacctg | gagagactgg | acgtggccga gtgcaacgcc | 1980 |
| ctggtggaga | tccccagcag | cgtggccaac | ctgcacaaga | tcgtgaacct gcacatggag | 2040 |

```
agctgcgaga gcctggaggt gatccccacc ctgatcaacc tggccagcct gaagatcatc    2100
aacatccacg actgcccag actgaagagc ttccccgacg tgcccaccag cctggaggag    2160
ctggtgatcg agaagaccgg cgtgcaggag ctgcccgcca gcttcagaca ctgcaccggc    2220
gtgaccaccc tgtacatctg cagcaacaga aacctgaaga ccttcagcac ccacctgccc    2280
atgggcctga aaagctgga cctgagcaac tgcggcatcg agtgggtgac cgacagcatc    2340
aaggacctgc acaacctgta ctacctgaag ctgagcggct gcaagagact ggtgagcctg    2400
cccgagctgc cctgcagcct ggagtgcctg ttcgccgagg actgcaccag cctggagaga    2460
gtgagcgaca gcctgaacat ccccaacgcc cagttcaact tcatcaagtg cttctgcctg    2520
gagcacgagg cccacaaggc cgtgatcaac cagagcttcc tgcacatgca gatcggcatc    2580
cccgccagag agggcctgga ggaggtggac ttccacatcc acggcaactg catctgcggc    2640
ccccccaccg ccttcaacag attcaaggtg tgcgtggtgc tgagcgccca c            2691
```

<210> SEQ ID NO 17
<211> LENGTH: 897
<212> TYPE: PRT
<213> ORGANISM: Artificial Sequence
<220> FEATURE:
<223> OTHER INFORMATION: Amino acid sequence HCP6, variant 3

<400> SEQUENCE: 17

```
Met Ala Cys Thr Ser Thr Ser Pro His Asn Trp Arg Tyr Asn Val Phe
1               5                   10                  15

Thr Ser Phe His Gly Pro Asp Val Arg Ile Arg Phe Met Cys Lys Leu
            20                  25                  30

Arg Gln Gln Phe Ile Tyr Gln Gly Ile Thr Met Trp Asp Asp Asn Gly
        35                  40                  45

Ile Glu Arg Ser Gln Ile Ile Ala Pro Ile Leu Arg Arg Leu Ala Gly
    50                  55                  60

Glu Ser Arg Ile Val Ile Met Leu Leu Thr Lys Asn Tyr Ala Ser Ser
65                  70                  75                  80

Ser Tyr Ser Leu Asp Glu Leu Leu Glu Ile Leu Lys Cys Lys Asp Asp
                85                  90                  95

Ile Ile Asn Ile Ala Gly Thr Val Phe Trp Glu Met Glu Pro Ser Glu
            100                 105                 110

Val Arg Asn Gln Thr Ala Asp Phe Gly Ile Ala Phe Lys Glu Thr Cys
        115                 120                 125

Ala His Lys Thr Glu Glu Arg Gln Lys Trp Thr Gln Ala Leu Thr
    130                 135                 140

Tyr Val Gly Asn Ile Ala Gly Glu Asp Phe Lys Arg Trp Pro Asn Glu
145                 150                 155                 160

Gly Arg Met Ile Glu His Ile Met Arg Asp Gly Ser Glu Leu Val Gln
                165                 170                 175

Ile Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
        195                 200                 205

Ile Val Gly Ile Ser Gly Pro Ala Gly Ile Gly Lys Ser Thr Ile Ala
    210                 215                 220

Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Leu Glu Glu Trp Arg
                245                 250                 255
```

```
Ile Lys Leu His Ala Gln Asn Gln Met Ile Ile Phe Val Ile Gln Asn
            260                 265                 270

Asp Lys Ile Arg Val Val Arg Met Thr Val Met Lys Asp Lys Leu Glu
            275                 280                 285

Glu Leu Lys Ile Ala Ile Val Leu Asp Glu Val Glu Lys Leu Tyr Asn
            290                 295                 300

Ile Glu Val Leu Met Asp Ile Arg Trp Phe Gly Pro Gly Ser His Met
305                 310                 315                 320

Val Val Thr Thr Asp Asn Arg Glu Ile Leu Leu Gln Lys Leu Ala Lys
                325                 330                 335

Asp Ile Phe His Val Leu Tyr Pro Ser Glu Gly Glu Ala Leu Gly Ile
            340                 345                 350

Trp Cys Met Ser Val Phe Lys Asn Pro Ser Pro Tyr Gly Phe Ile
            355                 360                 365

Lys Met Thr Tyr Asp Met Val Ser Ile Cys Ile Asn Leu Pro Ile Met
            370                 375                 380

Val His Val Leu Gly Ser Leu Leu Trp Gly Arg Thr Gln Ala Glu Trp
385                 390                 395                 400

Ile Glu Glu Leu Pro Arg Leu Lys Asp Cys Leu Asp Gly Arg Ile Glu
                405                 410                 415

Ser Val Leu Lys Val Gly Tyr Glu Ser Leu Tyr Glu Lys Asp Gln Ala
            420                 425                 430

Leu Phe Leu Leu Ile Ala Val Tyr Phe Asn Tyr Asp Tyr Val Asp Tyr
            435                 440                 445

Val Thr Ser Met Leu Glu Asn Thr Asn Val Leu Asp Val Lys Leu Gly
            450                 455                 460

Leu Lys Lys Gly Gly Gln Arg Thr Leu Ile Asn Ala Asp Ile Asp His
465                 470                 475                 480

Asn Arg Lys Cys Arg Val Val Met Asn Arg Met Leu Asn Val Ile Val
                485                 490                 495

Lys Glu Val Ile Cys Lys Gln Lys Ile Ser Lys Arg Lys Ile Leu Asp
            500                 505                 510

Asp Pro Gln Glu Ile Cys Phe Leu Leu Glu Gly Ala Lys Leu Lys Ile
            515                 520                 525

Ser Ala Val Gly Leu Cys Leu Glu Met Ala Asp Ile His Asp Leu Val
            530                 535                 540

Ala Gln Lys Lys Ala Trp Lys Lys Met Cys Asn Leu Leu Ile Val His
545                 550                 555                 560

Val Trp Asn Gly Thr Glu Pro Lys Glu Ser Arg Leu His Ile Pro Asp
                565                 570                 575

Glu Ala Glu Ile Pro Cys Thr Ile Arg Leu Ile His Trp Glu Val Tyr
            580                 585                 590

Pro His Arg Ser Phe Arg Phe Gly Pro Glu Asn Leu Val Thr Leu Asn
            595                 600                 605

Met Glu Tyr Ser Glu Leu Glu Lys Leu Trp Lys Gly Thr Gln Pro Leu
            610                 615                 620

Ala Asn Leu Lys Glu Met Asn Leu Cys Gly Ser Ser Cys Leu Lys Glu
625                 630                 635                 640

Leu Pro Asp Leu Ser Lys Ala Ala Asn Leu Glu Arg Leu Asp Val Ala
                645                 650                 655

Glu Cys Asn Ala Leu Val Glu Ile Pro Ser Ser Val Ala Asn Leu His
            660                 665                 670
```

| | | | | | | | | | | | |
|---|---|---|---|---|---|---|---|---|---|---|---|
|Lys|Ile|Val|Asn|Leu|His|Met|Glu|Ser|Cys|Glu|Ser|Leu|Glu|Val|Ile|
| | | |675| | | |680| | | |685|

Pro Thr Leu Ile Asn Leu Ala Ser Leu Lys Ile Asn Ile His Asp
    690                    695                    700

Cys Pro Arg Leu Lys Ser Phe Pro Asp Val Pro Thr Ser Leu Glu Glu
705                    710                    715                    720

Leu Val Ile Glu Lys Thr Gly Val Gln Glu Leu Pro Ala Ser Phe Arg
              725                    730                    735

His Cys Thr Gly Val Thr Thr Leu Tyr Ile Cys Ser Asn Arg Asn Leu
          740                    745                    750

Lys Thr Phe Ser Thr His Leu Pro Met Gly Leu Arg Lys Leu Asp Leu
      755                    760                    765

Ser Asn Cys Gly Ile Glu Trp Val Thr Asp Ser Ile Lys Asp Leu His
770                    775                    780

Asn Leu Tyr Tyr Leu Lys Leu Ser Gly Cys Lys Arg Leu Val Ser Leu
785                    790                    795                    800

Pro Glu Leu Pro Cys Ser Leu Glu Cys Leu Phe Ala Glu Asp Cys Thr
              805                    810                    815

Ser Leu Glu Arg Val Ser Asp Ser Leu Asn Ile Pro Asn Ala Gln Phe
          820                    825                    830

Asn Phe Ile Lys Cys Phe Cys Leu Glu His Glu Ala His Lys Ala Val
      835                    840                    845

Ile Asn Gln Ser Phe Leu His Met Gln Ile Gly Ile Pro Ala Arg Glu
850                    855                    860

Gly Leu Glu Glu Val Asp Phe His Ile His Gly Asn Cys Ile Cys Gly
865                    870                    875                    880

Pro Pro Thr Ala Phe Asn Arg Phe Lys Val Cys Val Val Leu Ser Ala
              885                    890                    895

His

<210> SEQ ID NO 18
<211> LENGTH: 2691
<212> TYPE: DNA
<213> ORGANISM: Artificial Sequence
<220> FEATURE:
<221> NAME/KEY: source
<222> LOCATION: 1..2691
<223> OTHER INFORMATION: /organism="Artificial Sequence"
    /note="Nucleotide sequence HCP6, variant 4"
    /mol_type="unassigned DNA"

<400> SEQUENCE: 18
atggccagca ccagcagcag ccccagaaac tggagataca acgtgttcac cagcttccac    60
ggccccgacg tgagaatcaa gtacctgagc cacctgagac agaactggat gtaccagggc   120
atgaccatgt acgacgacaa cggcatcgag agatgccagg tgatcatccc cgccctgaag   180
aaggccatgg gcgagagcag aatcgccatc ctgggcctga ccaagcagta cgtgtgcagc   240
agcttcagcc tggacgagat gatcgagatc ctgaagtgca aggaggacat cctgaacatc   300
gtgatgaccg tgttctggga cgtggacccc agcgaggtga cagcagag cgtggacttc   360 ggcatcgcct tcaaggagac ctgcgcccac aagaccgagg aggagagaca gaagtggacc   420
caggccctga cctacgtggg caacatcgcc ggcgaggagt tcaagcactg gccccaggag   480
atcaaggtgc tggagaagat cgccaaggag gtgagcgaca tgctgaacgg cacccctgc   540 agagacttcg acggcatggt gggcctgaac gaccacctga gagagatgga gagcctgctg   600
gacctgaaga cgacggcgt gaagatcgtg ggcatcagcg gccccgccgg catcggcaag   660

| | |
|---|---|
| agcaccatcg ccaccgccct gcacggcaga ctgagcaaca tgttccagag aacctgcttc | 720 |
| gtggacaacc tgagagagag ctacaagatc ggcctggagg agtacagact gaaggtgcac | 780 |
| ctgcagaacc agatgatgct gtacgtgctg aaccaggaca aggtgagagt ggcccacatc | 840 |
| agcgtgatga aggagagaat cgacgagctg agaatgctga tcatcctgga cgacgtggac | 900 |
| aagctgtaca acctggaggc cctgctggac atcagatact tcggccccgc cagccacatc | 960 |
| atcgtgacca ccgagaacag agaggtgctg ctgaaccacg cgccaaggca catctggcac | 1020 |
| gtgggctacc ccagcgacgt ggagctgatg ggcatcttct gcctgagcgc cttcagaaac | 1080 |
| ccctgccccc cctggggctt cctgaagatc accttcgagg tggccagcat caccggcaac | 1140 |
| ctgcccgtga tgctgaagat gctgggcacc ctgctgtaca tcaagagcaa cgccgactgg | 1200 |
| atcgaggagc tgcccagact gaaggactgc ctggacggca aatcgagag cgtgctgaag | 1260 |
| gtgggctacg agagcctgta cgagaaggac caggccctgt cctgctgat cgccgtgtac | 1320 |
| ttcaactacg actacgtgga ctacgtgacc agcatgctgg agaacaccaa cgtgctggac | 1380 |
| gtgcacctgg gcctgcacaa gctggcccag agaagcatgg cccagatcga catcgaccac | 1440 |
| aacagacaca gcaaggtggt gatgcagaga ctgctgcagg tgatggccag agaggtgctg | 1500 |
| agcaagcaga agatcagcaa gagaaagatc ggcgaggagc cccaggacgc ctgctacgtg | 1560 |
| ctggaggagg ccaagggcaa gggctgcgcc ggcggcctga gcgtggacgt gggcgacatc | 1620 |
| cacgagctgg tgatcaacaa gaaggccttc aagaagatgt gcaacctgct gatcggcaag | 1680 |
| gtgttccagg gcaccgaccc cagagacagc aagctgcacg tgcccgacga gatggacgcc | 1740 |
| cccagcagca tcagagccct gaagtgggag atgtacccca agaagacctg gagatggggc | 1800 |
| cccgagaacc tggtgaccct gaacatggag tacagcgagc tggagaagct gtggaagggc | 1860 |
| acccagcccc tggccaacct gaaggagatg aacctgtgcg gcagcagctg cctgaaggag | 1920 |
| ctgcccgacc tgagcaaggc cgccaacctg gagagactgg acgtggccga gtgcaacgcc | 1980 |
| ctggtggaga tccccagcag cgtggccaac ctgcacaaga tcgtgaacct gcacatggag | 2040 |
| agctgcgaga gcctggaggt gatccccacc ctgatcaacc tggccagcct gaagatcatc | 2100 |
| aacatccacg actgccccag actgaagagc ttccccgacg tgcccaccag cctggaggag | 2160 |
| ctggtgatcg agaagaccgg cgtgcaggag ctgcccgcca gcttcagaca ctgcaccggc | 2220 |
| gtgaccaccc tgtacatctg cagcaacaga aacctgaaga ccttcagcac ccacctgccc | 2280 |
| atgggcctga aaagctgga cctgagcaac tgcggcatcg agtgggtgac cgacagcatc | 2340 |
| aaggacctgc acaacctgta ctacctgaag ctgagcggct gcaagagact ggtgagcctg | 2400 |
| cccgagctgc cctgcagcct ggagtgcctg ttcgccgagg actgcaccag cctggagaga | 2460 |
| gtgagcgaca gcctgaacat ccccaacgcc cagttcaact tcctgaagtg ctggaccctg | 2520 |
| gagagagagg gcagaagagc catcatccag cagagcttcg tgcacgccaa cgtgggcatg | 2580 |
| cccgccaagg acatcctgga ggaggtggag tacagactga gaggccagtg cctgaccatc | 2640 |
| ccccccagcg ccttccagag attccacgcc tgcgtgatcc tgagcatcca c | 2691 |

<210> SEQ ID NO 19
<211> LENGTH: 897
<212> TYPE: PRT
<213> ORGANISM: Artificial Sequence
<220> FEATURE:
<223> OTHER INFORMATION: Amino acid sequence HCP6, variant 4

<400> SEQUENCE: 19

```
Met Ala Ser Thr Ser Ser Pro Arg Asn Trp Arg Tyr Asn Val Phe
1               5                   10                  15

Thr Ser Phe His Gly Pro Asp Val Arg Ile Lys Tyr Leu Ser His Leu
                20                  25                  30

Arg Gln Asn Trp Met Tyr Gln Gly Met Thr Met Tyr Asp Asp Asn Gly
            35                  40                  45

Ile Glu Arg Cys Gln Val Ile Ile Pro Ala Leu Lys Lys Ala Met Gly
        50                  55                  60

Glu Ser Arg Ile Ala Ile Leu Gly Leu Thr Lys Gln Tyr Val Cys Ser
65                  70                  75                  80

Ser Phe Ser Leu Asp Glu Met Ile Glu Ile Leu Lys Cys Lys Glu Asp
                85                  90                  95

Ile Leu Asn Ile Val Met Thr Val Phe Trp Asp Val Asp Pro Ser Glu
            100                 105                 110

Val Arg Gln Gln Ser Val Asp Phe Gly Ile Ala Phe Lys Glu Thr Cys
        115                 120                 125

Ala His Lys Thr Glu Glu Arg Gln Lys Trp Thr Gln Ala Leu Thr
        130                 135                 140

Tyr Val Gly Asn Ile Ala Gly Glu Phe Lys His Trp Pro Gln Glu
145                 150                 155                 160

Ile Lys Val Leu Glu Lys Ile Ala Lys Glu Val Ser Asp Met Leu Asn
                165                 170                 175

Gly Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
        195                 200                 205

Ile Val Gly Ile Ser Gly Pro Ala Gly Ile Gly Lys Ser Thr Ile Ala
        210                 215                 220

Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Leu Glu Glu Tyr Arg
                245                 250                 255

Leu Lys Val His Leu Gln Asn Gln Met Met Leu Tyr Val Leu Asn Gln
            260                 265                 270

Asp Lys Val Arg Val Ala His Ile Ser Val Met Lys Glu Arg Ile Asp
        275                 280                 285

Glu Leu Arg Met Leu Ile Ile Leu Asp Asp Val Asp Lys Leu Tyr Asn
        290                 295                 300

Leu Glu Ala Leu Leu Asp Ile Arg Tyr Phe Gly Pro Ala Ser His Ile
305                 310                 315                 320

Ile Val Thr Thr Glu Asn Arg Glu Val Leu Leu Asn His Gly Ala Lys
                325                 330                 335

Asp Ile Trp His Val Gly Tyr Pro Ser Asp Val Glu Leu Met Gly Ile
            340                 345                 350

Phe Cys Leu Ser Ala Phe Arg Asn Pro Cys Pro Pro Trp Gly Phe Leu
        355                 360                 365

Lys Ile Thr Phe Glu Val Ala Ser Ile Thr Gly Asn Leu Pro Val Met
        370                 375                 380

Leu Lys Met Leu Gly Thr Leu Leu Tyr Ile Lys Ser Asn Ala Asp Trp
385                 390                 395                 400

Ile Glu Glu Leu Pro Arg Leu Lys Asp Cys Leu Asp Gly Arg Ile Glu
                405                 410                 415

Ser Val Leu Lys Val Gly Tyr Glu Ser Leu Tyr Glu Lys Asp Gln Ala
```

-continued

```
                420                 425                 430
Leu Phe Leu Leu Ile Ala Val Tyr Phe Asn Tyr Asp Tyr Val Asp Tyr
            435                 440                 445

Val Thr Ser Met Leu Glu Asn Thr Asn Val Leu Asp Val His Leu Gly
        450                 455                 460

Leu His Lys Leu Ala Gln Arg Ser Met Ala Gln Ile Asp Ile Asp His
465                 470                 475                 480

Asn Arg His Ser Lys Val Val Met Gln Arg Leu Leu Gln Val Met Ala
                485                 490                 495

Arg Glu Val Leu Ser Lys Gln Lys Ile Ser Lys Arg Lys Ile Gly Glu
            500                 505                 510

Glu Pro Gln Asp Ala Cys Tyr Val Leu Glu Glu Ala Lys Gly Lys Gly
        515                 520                 525

Cys Ala Gly Gly Leu Ser Val Asp Val Gly Asp Ile His Glu Leu Val
    530                 535                 540

Ile Asn Lys Lys Ala Phe Lys Lys Met Cys Asn Leu Leu Ile Gly Lys
545                 550                 555                 560

Val Phe Gln Gly Thr Asp Pro Arg Asp Ser Lys Leu His Val Pro Asp
                565                 570                 575

Glu Met Asp Ala Pro Ser Ser Ile Arg Ala Leu Lys Trp Glu Met Tyr
            580                 585                 590

Pro Lys Lys Thr Trp Arg Trp Gly Pro Glu Asn Leu Val Thr Leu Asn
        595                 600                 605

Met Glu Tyr Ser Glu Leu Glu Lys Leu Trp Lys Gly Thr Gln Pro Leu
    610                 615                 620

Ala Asn Leu Lys Glu Met Asn Leu Cys Gly Ser Ser Cys Leu Lys Glu
625                 630                 635                 640

Leu Pro Asp Leu Ser Lys Ala Ala Asn Leu Glu Arg Leu Asp Val Ala
                645                 650                 655

Glu Cys Asn Ala Leu Val Glu Ile Pro Ser Ser Val Ala Asn Leu His
            660                 665                 670

Lys Ile Val Asn Leu His Met Glu Ser Cys Glu Ser Leu Glu Val Ile
        675                 680                 685

Pro Thr Leu Ile Asn Leu Ala Ser Leu Lys Ile Ile Asn Ile His Asp
    690                 695                 700

Cys Pro Arg Leu Lys Ser Phe Pro Asp Val Pro Thr Ser Leu Glu Glu
705                 710                 715                 720

Leu Val Ile Glu Lys Thr Gly Val Gln Glu Leu Pro Ala Ser Phe Arg
                725                 730                 735

His Cys Thr Gly Val Thr Thr Leu Tyr Ile Cys Ser Asn Arg Asn Leu
            740                 745                 750

Lys Thr Phe Ser Thr His Leu Pro Met Gly Leu Arg Lys Leu Asp Leu
        755                 760                 765

Ser Asn Cys Gly Ile Glu Trp Val Thr Asp Ser Ile Lys Asp Leu His
    770                 775                 780

Asn Leu Tyr Tyr Leu Lys Leu Ser Gly Cys Lys Arg Leu Val Ser Leu
785                 790                 795                 800

Pro Glu Leu Pro Cys Ser Leu Glu Cys Leu Phe Ala Glu Asp Cys Thr
                805                 810                 815

Ser Leu Glu Arg Val Ser Asp Ser Leu Asn Ile Pro Asn Ala Gln Phe
            820                 825                 830

Asn Phe Leu Lys Cys Trp Thr Leu Glu Arg Glu Gly Arg Arg Ala Ile
        835                 840                 845
```

Ile Gln Gln Ser Phe Val His Ala Asn Val Gly Met Pro Ala Lys Asp
    850                 855                 860

Ile Leu Glu Glu Val Glu Tyr Arg Leu Arg Gly Gln Cys Leu Thr Ile
865                 870                 875                 880

Pro Pro Ser Ala Phe Gln Arg Phe His Ala Cys Val Ile Leu Ser Ile
            885                 890                 895

His

<210> SEQ ID NO 20
<211> LENGTH: 2691
<212> TYPE: DNA
<213> ORGANISM: Artificial Sequence
<220> FEATURE:
<221> NAME/KEY: source
<222> LOCATION: 1..2691
<223> OTHER INFORMATION: /organism="Artificial Sequence"
      /note="Nucleotide sequence HCP6, variant 5"
      /mol_type="unassigned DNA"

<400> SEQUENCE: 20

| | |
|---|---:|
| atggccagca gctgcaccag ccccagaaac tggagataca acgtgttcac cagcttccac | 60 |
| ggccccgacg tgagaatcca cttcgccagc agactgagac agcagtacat ctggaacggc | 120 |
| atcaccatgt cgacgacaa cggcatcgac cacagccaga tcatggcccc cgccctgaag | 180 |
| aaggccatcg gcgagagcag aggcgccatc ctgggcgtga cccaccagta cgcctgcagc | 240 |
| acctggagcc tggacgacct gctggagatc gtgaagtgca aggaggacat cggcaacatc | 300 |
| gtggccaccg tgttctacga cgtggacccc agcgacgtga cagcagag cggcgacttc | 360 |
| ggcatcgcct tcaaggagac ctgcgcccac aagaccgagg aggagagaca gaagtggacc | 420 |
| caggccctga cctacgtggg caacatcgcc ggcgaggact tcaagcactg cccccaggag | 480 |
| gccaagatga tcgagagaat cctgagagag gtgagcgaca tcctgaacct gacccccctgc | 540 |
| agagacttcg acggcatggt gggcctgaac gaccacctga gagagatgga gagcctgctg | 600 |
| gacctgaaga cgacggcgt gaagatcgtg gcatcagcg gccccgccgg catcggcaag | 660 |
| agcaccatcg ccaccgccct gcacggcaga ctgagcaaca tgttccagag aacctgcttc | 720 |
| gtggacaacc tgagagagag ctacaagatc ggcctggacg agtacagact gaagatccac | 780 |
| ctgcagcagc agctgctggc ctacgtggtg aaccaggaca agatcagagt gggcaagctg | 840 |
| agcgtgatga aggacagact ggacgacctg agagtgctga tcatcctgga cgacgtggac | 900 |
| cacctgtaca acctggacgc cctggccgac atcagatggt tcggccccgg cagcagagtg | 960 |
| gtggtgacca ccgagcagag agacatcctg ctgaaccacg gcgtgaagga cgcctaccac | 1020 |
| gtgggcttcc ccaccgaggg cgaggccctg atgatcttct gcctgtgcgc ctacaagcag | 1080 |
| cccagccccc cctacctgtt cctgaagctg tgctacgagg tggccagcgt gagcctgaac | 1140 |
| ctgcccctgg gcatgcacgt gctgggcacc ctgatgtgga tcaagagcca ggccgactgg | 1200 |
| atcgaggagc tgcccagact gaaggactgc ctggacggca aatcgagag cgtgctgaag | 1260 |
| gtgggctacg agagcctgta cgagaaggac caggccctgt cctgctgat cgccgtgtac | 1320 |
| ttcaactacg actacgtgga ctacgtgacc agcatgctgg agaacaccaa cgtgctggac | 1380 |
| gtgagaatgg gcctgagaaa gctggccaac agatgcctga tccagatcga catcgacaga | 1440 |
| cagagaaagt gcagagtggt gatgaacaga ctgctgaacg tgatggccag agaggtgatc | 1500 |
| agcaagaaca agatcagcaa gagaaagatc ctggaggagc cccaggacat cagctacgtg | 1560 |
| ctggaggagg ccaagggcaa gggcagcgcc ctgggcggca gcctggacgg cgtggacatc | 1620 |

-continued

```
aaggagctgg tgatcaacaa gagagcctac aagaagatga gcaacctgct gatcctgaag   1680
gtgttcaacg gcaccgaccc cagagacagc aagctgcaca tgcccgacga gggcgagctg   1740
cccagcagca tcagagccct gcactgggag gcctacccca gacacagctt cagattcggc   1800
cccgagaacc tggtgaccct gaacatggag tacagcgagc tggagaagct gtggaagggc   1860
acccagcccc tggccaacct gaaggagatg aacctgtgcg gcagcagctg cctgaaggag   1920
ctgcccgacc tgagcaaggc cgccaacctg gagagactgg acgtggccga gtgcaacgcc   1980
ctggtggaga tccccagcag cgtggccaac ctgcacaaga tcgtgaacct gcacatggag   2040
agctgcgaga gcctggaggt gatccccacc ctgatcaacc tggccagcct gaagatcatc   2100
aacatccacg actgccccag actgaagagc ttccccgacg tgcccaccag cctggaggag   2160
ctggtgatcg agaagaccgg cgtgcaggag ctgcccgcca gcttcagaca ctgcaccggc   2220
gtgaccaccc tgtacatctg cagcaacaga aacctgaaga ccttcagcac ccacctgccc   2280
atgggcctga aaagctgga cctgagcaac tgcggcatcg agtgggtgac cgacagcatc   2340
aaggacctgc acaacctgta ctacctgaag ctgagcggct gcaagagact ggtgagcctg   2400
cccgagctgc cctgcagcct ggagtgcctg ttcgccgagg actgcaccag cctggagaga   2460
gtgagcgaca gcctgaacat ccccaacgcc cagttcaact tcgtgaagtg cttcagcctg   2520
gagagagagg ccagaagagc cgtgatccag cagagcttcg tgcacggcaa cgtgatcctg   2580
cccgccagag aggtgctgga cgaggtggac tacagagcca agggcaactg cctgaccatc   2640
cccccaccg ccttcaacag attcaaggtg tgcgccgccc tgagcatcca c             2691
```

<210> SEQ ID NO 21
<211> LENGTH: 897
<212> TYPE: PRT
<213> ORGANISM: Artificial Sequence
<220> FEATURE:
<223> OTHER INFORMATION: Amino acid sequence HCP6, variant 5

<400> SEQUENCE: 21

```
Met Ala Ser Ser Cys Thr Ser Pro Arg Asn Trp Arg Tyr Asn Val Phe
1               5                   10                  15

Thr Ser Phe His Gly Pro Asp Val Arg Ile His Phe Ala Ser Arg Leu
            20                  25                  30

Arg Gln Gln Tyr Ile Trp Asn Gly Ile Thr Met Phe Asp Asp Asn Gly
        35                  40                  45

Ile Asp His Ser Gln Ile Met Ala Pro Ala Leu Lys Lys Ala Ile Gly
    50                  55                  60

Glu Ser Arg Gly Ala Ile Leu Gly Val Thr His Gln Tyr Ala Cys Ser
65                  70                  75                  80

Thr Trp Ser Leu Asp Asp Leu Leu Glu Ile Val Lys Cys Lys Glu Asp
                85                  90                  95

Ile Gly Asn Ile Val Ala Thr Val Phe Tyr Asp Val Asp Pro Ser Asp
            100                 105                 110

Val Arg Gln Gln Ser Gly Asp Phe Gly Ile Ala Phe Lys Glu Thr Cys
        115                 120                 125

Ala His Lys Thr Glu Glu Glu Arg Gln Lys Trp Thr Gln Ala Leu Thr
    130                 135                 140

Tyr Val Gly Asn Ile Ala Gly Glu Asp Phe Lys His Trp Pro Gln Glu
145                 150                 155                 160

Ala Lys Met Ile Glu Arg Ile Leu Arg Glu Val Ser Asp Ile Leu Asn
                165                 170                 175
```

-continued

Leu Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
            195                 200                 205

Ile Val Gly Ile Ser Gly Pro Ala Gly Ile Gly Lys Ser Thr Ile Ala
210                 215                 220

Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Leu Asp Glu Tyr Arg
            245                 250                 255

Leu Lys Ile His Leu Gln Gln Gln Leu Leu Ala Tyr Val Val Asn Gln
            260                 265                 270

Asp Lys Ile Arg Val Gly Lys Leu Ser Val Met Lys Asp Arg Leu Asp
            275                 280                 285

Asp Leu Arg Val Leu Ile Ile Leu Asp Asp Val Asp His Leu Tyr Asn
            290                 295                 300

Leu Asp Ala Leu Ala Asp Ile Arg Trp Phe Gly Pro Gly Ser Arg Val
305                 310                 315                 320

Val Val Thr Thr Glu Gln Arg Asp Ile Leu Leu Asn His Gly Val Lys
            325                 330                 335

Asp Ala Tyr His Val Gly Phe Pro Thr Glu Gly Glu Ala Leu Met Ile
            340                 345                 350

Phe Cys Leu Cys Ala Tyr Lys Gln Pro Ser Pro Tyr Leu Phe Leu
            355                 360                 365

Lys Leu Cys Tyr Glu Val Ala Ser Val Ser Leu Asn Leu Pro Leu Gly
            370                 375                 380

Met His Val Leu Gly Thr Leu Met Trp Ile Lys Ser Gln Ala Asp Trp
385                 390                 395                 400

Ile Glu Glu Leu Pro Arg Leu Lys Asp Cys Leu Asp Gly Arg Ile Glu
            405                 410                 415

Ser Val Leu Lys Val Gly Tyr Glu Ser Leu Tyr Glu Lys Asp Gln Ala
            420                 425                 430

Leu Phe Leu Leu Ile Ala Val Tyr Phe Asn Tyr Asp Tyr Val Asp Tyr
            435                 440                 445

Val Thr Ser Met Leu Glu Asn Thr Asn Val Leu Asp Val Arg Met Gly
            450                 455                 460

Leu Arg Lys Leu Ala Asn Arg Cys Leu Ile Gln Ile Asp Ile Asp Arg
465                 470                 475                 480

Gln Arg Lys Cys Arg Val Val Met Asn Arg Leu Leu Asn Val Met Ala
            485                 490                 495

Arg Glu Val Ile Ser Lys Asn Lys Ile Ser Lys Arg Lys Ile Leu Glu
            500                 505                 510

Glu Pro Gln Asp Ile Ser Tyr Val Leu Glu Glu Ala Lys Gly Lys Gly
            515                 520                 525

Ser Ala Leu Gly Gly Ser Leu Asp Gly Val Asp Ile Lys Glu Leu Val
            530                 535                 540

Ile Asn Lys Arg Ala Tyr Lys Lys Met Ser Asn Leu Leu Ile Leu Lys
545                 550                 555                 560

Val Phe Asn Gly Thr Asp Pro Arg Asp Ser Lys Leu His Met Pro Asp
            565                 570                 575

Glu Gly Glu Leu Pro Ser Ser Ile Arg Ala Leu His Trp Glu Ala Tyr
            580                 585                 590

```
Pro Arg His Ser Phe Arg Phe Gly Pro Glu Asn Leu Val Thr Leu Asn
            595                 600                 605

Met Glu Tyr Ser Glu Leu Glu Lys Leu Trp Lys Gly Thr Gln Pro Leu
    610                 615                 620

Ala Asn Leu Lys Glu Met Asn Leu Cys Gly Ser Ser Cys Leu Lys Glu
625                 630                 635                 640

Leu Pro Asp Leu Ser Lys Ala Ala Asn Leu Glu Arg Leu Asp Val Ala
                645                 650                 655

Glu Cys Asn Ala Leu Val Glu Ile Pro Ser Ser Val Ala Asn Leu His
            660                 665                 670

Lys Ile Val Asn Leu His Met Glu Ser Cys Glu Ser Leu Glu Val Ile
        675                 680                 685

Pro Thr Leu Ile Asn Leu Ala Ser Leu Lys Ile Ile Asn Ile His Asp
    690                 695                 700

Cys Pro Arg Leu Lys Ser Phe Pro Asp Val Pro Thr Ser Leu Glu Glu
705                 710                 715                 720

Leu Val Ile Glu Lys Thr Gly Val Gln Glu Leu Pro Ala Ser Phe Arg
                725                 730                 735

His Cys Thr Gly Val Thr Thr Leu Tyr Ile Cys Ser Asn Arg Asn Leu
            740                 745                 750

Lys Thr Phe Ser Thr His Leu Pro Met Gly Leu Arg Lys Leu Asp Leu
        755                 760                 765

Ser Asn Cys Gly Ile Glu Trp Val Thr Asp Ser Ile Lys Asp Leu His
    770                 775                 780

Asn Leu Tyr Tyr Leu Lys Leu Ser Gly Cys Lys Arg Leu Val Ser Leu
785                 790                 795                 800

Pro Glu Leu Pro Cys Ser Leu Glu Cys Leu Phe Ala Glu Asp Cys Thr
                805                 810                 815

Ser Leu Glu Arg Val Ser Asp Ser Leu Asn Ile Pro Asn Ala Gln Phe
            820                 825                 830

Asn Phe Val Lys Cys Phe Ser Leu Glu Arg Glu Ala Arg Arg Ala Val
        835                 840                 845

Ile Gln Gln Ser Phe Val His Gly Asn Val Ile Leu Pro Ala Arg Glu
    850                 855                 860

Val Leu Asp Glu Val Asp Tyr Arg Ala Lys Gly Asn Cys Leu Thr Ile
865                 870                 875                 880

Pro Pro Thr Ala Phe Asn Arg Phe Lys Val Cys Ala Ala Leu Ser Ile
                885                 890                 895

His

<210> SEQ ID NO 22
<211> LENGTH: 2691
<212> TYPE: DNA
<213> ORGANISM: Artificial Sequence
<220> FEATURE:
<221> NAME/KEY: source
<222> LOCATION: 1..2691
<223> OTHER INFORMATION: /organism="Artificial Sequence"
     /note="Nucleotide sequence HCP6, variant 6"
     /mol_type="unassigned DNA"

<400> SEQUENCE: 22
atggccagca gcagcagcag ccccagaaac tggagataca acgtgttcac cagcttccac      60
ggccccgacg tgagaatcaa gtacgccagc cacggcagac agcagttcgc cttcaacggc     120
atcaccatgt tcgacgacaa cggcatcgac agaagccaga tcatcgcccc cgccctgaag     180
```

-continued

```
aaggccatcg gcgagagcag aatcctgatc ctgctggtga gcaagaacta cgccagcagc        240
tgctggagca tcgacgagat gctggagatc ctgaagtgca aggacgacgt gggccagatc        300
gtgatgaccg tgtactacga ggtggacccc accgacgtga gacagcagac cctggacttc        360
ggcatcgcct tcaaggagac ctgcgcccac aagaccgagg aggagagaca gaagtggacc        420
caggccctga cctacgtggg caacatcgcc ggcgaggact ggaagcacta ccccaacgag        480
gccaagggca tcgagaagct ggccagagac gtgagcgaca tcctgaacat gacccccctgc       540 agagacttcg acggcatggt gggcctgaac gaccacctga gagagatgga gagcctgctg       600
gacctgaaga cgacggcgt gaagatcgtg ggcatcagcg gccccgccgg catcggcaag        660
agcaccatcg ccaccgccct gcacggcaga ctgagcaaca tgttccagag aacctgcttc       720
gtggacaacc tgagagagag ctacaagatc ggcctggacg agtacagact gaagatgcac       780
ctgcagcagc agctgctggc ctacatgctg aaccaggaca agatcagagt gggccacgcc       840
agcatcatga aggagagact ggacgagctg agagtgctga tcatcctgga cgacgtggag       900
cacctgtacc agctggaggc cctgatggac atcagattct tcatgcccgg ctgcagagtg       960
atcgtgacca ccgagaacag agacatcctg ctgcagcacg gcatcaagga gatctaccac      1020
gtgggcttcc ccagcgaggg cgaggccctg atgatcttct gcggcagcgc cttcagacag      1080
cccagccccc cctacggctt cggcagactg acctacgagg tggccagcat cagcggcaac      1140
gtgcccgccg gcctgcacgt gctgggctgc ctgctgtggg gcaagagcca ggccgactgg      1200
atcgaggagc tgcccagact gaaggactgc ctggacggca gaatcgagag cgtgctgaag      1260
gtgggctaca gagcctgta cgagaaggac caggcccctgt tcctgctgat cgccgtgtac      1320
ttcaactacg actacgtgga ctacgtgacc agcatgctgg agaacaccaa cgtgctggac      1380
gtgagactgg gcgtgaagaa gctggccaac agatgcatca tcaacatcga catcgacaag      1440
aacaagaaga gcagagtgat gatgaacaga ctgctgcagg tgatgatgca cgaggtgatc      1500
agcaagcaga agatcagcca cagaaagatc atcgaggacc cccaggacat cagctacgtg      1560
ctggaggagg ccaagggcca cggcagcgcc ctgggcctga gcatcgacgt ggccgacctg      1620
aaggagctgg tgatcaacaa gaaggccttc aagaagatgt gcaacctgct gatcctgaag      1680
gtgtacaacg gctgcgaccc cagagagagc aagctgcacg tgcccgagga catggagctg      1740
cccagctgca tcagactgct gcacttcgag gcctacccca aaagagagctt ccactacggc      1800 cccgagaacc tggtgaccct gaacatggag tacagcgagc tggagaagct gtggaagggc      1860
acccagcccc tggccaacct gaaggagatg aacctgtgcg gcagcagctg cctgaaggag      1920
ctgcccgacc tgagcaaggc cgccaacctg gagagactgg acgtggccga gtgcaacgcc      1980
ctggtggaga tccccagcag cgtggccaac ctgcacaaga tcgtgaacct gcacatggag      2040
agctgcgaga gcctggaggt gatccccacc ctgatcaacc tggccagcct gaagatcatc      2100
aacatccacg actgccccag actgaagagc ttccccgacg tgcccaccag cctggaggag      2160
ctggtgatcg agaagaccgg cgtgcaggag ctgcccgcca gcttcagaca ctgcaccggc      2220
gtgaccaccc tgtacatctg cagcaacaga aacctgaaga ccttcagcac ccacctgccc      2280
atgggcctga aaagctgga cctgagcaac tgcggcatcg agtgggtgac cgacagcatc      2340
aaggacctgc acaacctgta cacctgaagg ctgagcggct gcaagagact ggtgagcctg      2400
cccgagctgc cctgcagcct ggagtgcctg ttcgccgagg actgcaccag cctggagaga      2460
gtgagcgaca gcctgaacat ccccaacgcc cagttcaact tcatcaagtg cttcaccctg      2520
gacagagagg ccagaagagc catcatccag cagagcttcg tgcacggcca ggtgatcctg      2580
```

```
cccgccagag aggtgctgga cgaggtggac tacagagccc acggcaactg cctgaccatc    2640 cccccaccc tgtggaacag attcaaggtg tgcgtggtgc tgagcatcca c              2691
```

<210> SEQ ID NO 23
<211> LENGTH: 897
<212> TYPE: PRT
<213> ORGANISM: Artificial Sequence
<220> FEATURE:
<223> OTHER INFORMATION: Amino acid sequence HCP6, variant 6

<400> SEQUENCE: 23

```
Met Ala Ser Ser Ser Ser Pro Arg Asn Trp Arg Tyr Asn Val Phe
1               5                   10                  15

Thr Ser Phe His Gly Pro Asp Val Arg Ile Lys Tyr Ala Ser His Gly
            20                  25                  30

Arg Gln Gln Phe Ala Phe Asn Gly Ile Thr Met Phe Asp Asp Asn Gly
        35                  40                  45

Ile Asp Arg Ser Gln Ile Ile Ala Pro Ala Leu Lys Lys Ala Ile Gly
    50                  55                  60

Glu Ser Arg Ile Leu Ile Leu Leu Val Ser Lys Asn Tyr Ala Ser Ser
65                  70                  75                  80

Cys Trp Ser Ile Asp Glu Met Leu Glu Ile Leu Lys Cys Lys Asp Asp
                85                  90                  95

Val Gly Gln Ile Val Met Thr Val Tyr Tyr Glu Val Asp Pro Thr Asp
            100                 105                 110

Val Arg Gln Gln Thr Leu Asp Phe Gly Ile Ala Phe Lys Glu Thr Cys
        115                 120                 125

Ala His Lys Thr Glu Glu Arg Gln Lys Trp Thr Gln Ala Leu Thr
    130                 135                 140

Tyr Val Gly Asn Ile Ala Gly Glu Asp Trp Lys His Tyr Pro Asn Glu
145                 150                 155                 160

Ala Lys Gly Ile Glu Lys Leu Ala Arg Asp Val Ser Asp Ile Leu Asn
                165                 170                 175

Met Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
        195                 200                 205

Ile Val Gly Ile Ser Gly Pro Ala Gly Ile Gly Lys Ser Thr Ile Ala
    210                 215                 220

Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Leu Asp Glu Tyr Arg
                245                 250                 255

Leu Lys Met His Leu Gln Gln Leu Leu Ala Tyr Met Leu Asn Gln
            260                 265                 270

Asp Lys Ile Arg Val Gly His Ala Ser Ile Met Lys Glu Arg Leu Asp
        275                 280                 285

Glu Leu Arg Val Leu Ile Ile Leu Asp Asp Val Glu His Leu Tyr Gln
    290                 295                 300

Leu Glu Ala Leu Met Asp Ile Arg Phe Phe Met Pro Gly Cys Arg Val
305                 310                 315                 320

Ile Val Thr Thr Glu Asn Arg Asp Ile Leu Leu Gln His Gly Ile Lys
                325                 330                 335

Glu Ile Tyr His Val Gly Phe Pro Ser Glu Gly Glu Ala Leu Met Ile
```

-continued

```
            340                 345                 350
Phe Cys Gly Ser Ala Phe Arg Gln Pro Ser Pro Tyr Gly Phe Gly
            355                 360                 365
Arg Leu Thr Tyr Glu Val Ala Ser Ile Ser Gly Asn Val Pro Ala Gly
            370                 375                 380
Leu His Val Leu Gly Cys Leu Leu Trp Gly Lys Ser Gln Ala Asp Trp
385                 390                 395                 400
Ile Glu Glu Leu Pro Arg Leu Lys Asp Cys Leu Asp Gly Arg Ile Glu
                    405                 410                 415
Ser Val Leu Lys Val Gly Tyr Glu Ser Leu Tyr Glu Lys Asp Gln Ala
                    420                 425                 430
Leu Phe Leu Leu Ile Ala Val Tyr Phe Asn Tyr Asp Tyr Val Asp Tyr
            435                 440                 445
Val Thr Ser Met Leu Glu Asn Thr Asn Val Leu Asp Val Arg Leu Gly
            450                 455                 460
Val Lys Lys Leu Ala Asn Arg Cys Ile Ile Asn Ile Asp Ile Asp Lys
465                 470                 475                 480
Asn Lys Lys Ser Arg Val Met Met Asn Arg Leu Leu Gln Val Met Met
                    485                 490                 495
His Glu Val Ile Ser Lys Gln Lys Ile Ser His Arg Lys Ile Ile Glu
                    500                 505                 510
Asp Pro Gln Asp Ile Ser Tyr Val Leu Glu Glu Ala Lys Gly His Gly
            515                 520                 525
Ser Ala Leu Gly Leu Ser Ile Asp Val Ala Asp Leu Lys Glu Leu Val
            530                 535                 540
Ile Asn Lys Lys Ala Phe Lys Lys Met Cys Asn Leu Leu Ile Leu Lys
545                 550                 555                 560
Val Tyr Asn Gly Cys Asp Pro Arg Glu Ser Lys Leu His Val Pro Glu
                    565                 570                 575
Asp Met Glu Leu Pro Ser Cys Ile Arg Leu Leu His Phe Glu Ala Tyr
                    580                 585                 590
Pro Arg Lys Ser Phe His Tyr Gly Pro Glu Asn Leu Val Thr Leu Asn
            595                 600                 605
Met Glu Tyr Ser Glu Leu Glu Lys Leu Trp Lys Gly Thr Gln Pro Leu
            610                 615                 620
Ala Asn Leu Lys Glu Met Asn Leu Cys Gly Ser Ser Cys Leu Lys Glu
625                 630                 635                 640
Leu Pro Asp Leu Ser Lys Ala Ala Asn Leu Glu Arg Leu Asp Val Ala
                    645                 650                 655
Glu Cys Asn Ala Leu Val Glu Ile Pro Ser Ser Val Ala Asn Leu His
                    660                 665                 670
Lys Ile Val Asn Leu His Met Glu Ser Cys Glu Ser Leu Glu Val Ile
            675                 680                 685
Pro Thr Leu Ile Asn Leu Ala Ser Leu Lys Ile Ile Asn Ile His Asp
            690                 695                 700
Cys Pro Arg Leu Lys Ser Phe Pro Asp Val Pro Thr Ser Leu Glu Glu
705                 710                 715                 720
Leu Val Ile Glu Lys Thr Gly Val Gln Glu Leu Pro Ala Ser Phe Arg
                    725                 730                 735
His Cys Thr Gly Val Thr Thr Leu Tyr Ile Cys Ser Asn Arg Asn Leu
                    740                 745                 750
Lys Thr Phe Ser Thr His Leu Pro Met Gly Leu Arg Lys Leu Asp Leu
            755                 760                 765
```

```
Ser Asn Cys Gly Ile Glu Trp Val Thr Asp Ser Ile Lys Asp Leu His
        770                 775                 780

Asn Leu Tyr Tyr Leu Lys Leu Ser Gly Cys Lys Arg Leu Val Ser Leu
785                 790                 795                 800

Pro Glu Leu Pro Cys Ser Leu Glu Cys Leu Phe Ala Glu Asp Cys Thr
                805                 810                 815

Ser Leu Glu Arg Val Ser Asp Ser Leu Asn Ile Pro Asn Ala Gln Phe
            820                 825                 830

Asn Phe Ile Lys Cys Phe Thr Leu Asp Arg Glu Ala Arg Arg Ala Ile
        835                 840                 845

Ile Gln Gln Ser Phe Val His Gly Gln Val Ile Leu Pro Ala Arg Glu
    850                 855                 860

Val Leu Asp Glu Val Asp Tyr Arg Ala His Gly Asn Cys Leu Thr Ile
865                 870                 875                 880

Pro Pro Thr Leu Trp Asn Arg Phe Lys Val Cys Val Val Leu Ser Ile
                885                 890                 895

His
```

<210> SEQ ID NO 24
<211> LENGTH: 2691
<212> TYPE: DNA
<213> ORGANISM: Artificial Sequence
<220> FEATURE:
<221> NAME/KEY: source
<222> LOCATION: 1..2691
<223> OTHER INFORMATION: /organism="Artificial Sequence"
      /note="Nucleotide sequence HCP6, variant 7"
      /mol_type="unassigned DNA"

<400> SEQUENCE: 24

```
atggccagct gcagcagcag ccccagaaac tggagataca acgtgttcac cagcttccac      60
ggccccgacg tgagaatcaa gttcctgagc cacctgcacc agcagttcat ctacaacggc     120
atcagcatgt tcgacgacaa cggcatcgag agaagccaga tcatcgcccc cgccctgaag     180
aaggccatgg cgagagcag aatcatcatc ctgctgctga gcaagaacta cgccagcagc     240
agctggagcc tggacgagct gctggagatc ctgaagtgca gagaggacct gggccagatc     300
gtgatgtgcg tgttctggga cgtggacccc agcgacgtgc accagcagtg cggcgacttc     360
ggcatcgcct tcaaggagac ctgcgcccac aagaccgagg aggagagaca gaagtggacc     420
caggccctga cctacgtggg caacatcgcc ggcgaggact tcaagcactg gcccaacgag     480
gccaagatga tcgagaagat cggcagagac gtgagcgaga tcctgaacgt gacccccctgc     540 agagacttcg acggcatggt gggcctgaac gaccacctga gagatgga gagcctgctg     600 gacctgaaga cgacggcgt gaagatcgtg ggcatcagcg gccccgccgg catcggcaag     660
agcaccatcg ccaccgccct gcacggcaga ctgagcaaca tgttccagag aacctgcttc     720
gtggacaacc tgagagagag ctacaagatc ggcatggacg agtacagact gaagctgaag     780
ctgcagcagc agatgatcgc ctacgtggcc aaccaggaca gatcagagt gggccacctg     840 agcgtgatga aggagagact ggacgacctg agagtgctga tcatcctgga cgacgtggag     900
cacctgtacc agatcgagat gatcgccgac atcagatggt cggcccccgg cagcagagtg     960
atcggcacca ccgagaacag agagatcctg ctgaaccacg gcatcaagga catctaccac    1020
gtgggcttcc ccagcgaggg cgaggccctg atgatcttct gcctgagcgc cttcagacag    1080
cccacccccc cctacggctt catgaagctg acctacgagg tggccagcat ctgcggcaac    1140
```

```
ctgcccctgg gcctgcacgt ggccggcacc ctgctgtgga tgaagagcca ggccgactgg    1200
atcgaggagc tgcccagact gaaggactgc ctggacggca gaatcgagag cgtgctgaag    1260
gtgggctacg agagcctgta cgagaaggac caggccctgt tcctgctgat cgccgtgtac    1320
ttcaactacg actacgtgga ctacgtgacc agcatgctgg agaacaccaa cgtgctggac    1380
gtgagactgg gcctgaagaa gctggccaac agaagcctga tccagatcga catcgaccac    1440
aacagaaaga gccacgtggt gatgaacaga ctggccaacg tgatggccag agaggtgatc    1500
agcaagcaga agatcagcaa gagaaagatc ctggacgacc ccaggacat  ctgctacgtg    1560 ctggacgagg ccaaggtgaa gggcagcgcc ctggccctga gcctggacgt ggccgagatc    1620
aaggagctgg tgatcaacaa gaaggccttc aagaagatgt gcaacctgct gatcctgaag    1680
gtgtacaacg gcaccgaccc cagagacagc aagctgcacg tgcccgacga gatggagctg    1740
cccaccagca tcagactgct gcactgggag gcctacccca gaaagagctt cagattcggc    1800
cccgagaacc tggtgaccct gaacatggag tacagcgagc tggagaagct gtggaagggc    1860
acccagcccc tggccaacct gaaggagatg aacctgtgcg gcagcagctg cctgaaggag    1920
ctgcccgacc tgagcaaggc cgccaacctg agagactgg  acgtggccga gtgcaacgcc    1980
ctggtggaga tccccagcag cgtggccaac ctgcacaaga tcgtgaacct gcacatggag    2040
agctgcgaga gcctggaggt gatccccacc ctgatcaacc tggccagcct gaagatcatc    2100
aacatccacg actgccccag actgaagagc ttccccgacg tgcccaccag cctggaggag    2160
ctggtgatcg agaagaccgg cgtgcaggag ctgcccgcca gcttcagaca ctgcaccggc    2220
gtgaccaccc tgtacatctg cagcaacaga aacctgaaga ccttcagcac ccacctgccc    2280
atgggcctga gaagctgga  cctgagcaac tgcggcatcg agtgggtgac cgacagcatc    2340
aaggacctgc acaacctgta ctacctgaag ctgagcggct gcaagagact ggtgagcctg    2400
cccgagctgc cctgcagcct ggagtgcctg ttcgccgagg actgcaccag cctggagaga    2460
gtgagcgaca gcctgaacat ccccaacgcc cagtggaact tcatcaagtg cttcaccctg    2520
gacagagagg ccagaagagc cggcatccag cagagcttcg tgcacggcaa cgtgatcctg    2580
cccgccagag aggtgctgga ggaggtggac tacagagcca gaggcaactg cctgaccatc    2640
ccccccagcg ccttcaacag attcagagtg tgcgtggtgc tgagcatcca c             2691
```

<210> SEQ ID NO 25
<211> LENGTH: 897
<212> TYPE: PRT
<213> ORGANISM: Artificial Sequence
<220> FEATURE:
<223> OTHER INFORMATION: Amino acid sequence HCP6, variant 7

<400> SEQUENCE: 25

```
Met Ala Ser Cys Ser Ser Pro Arg Asn Trp Arg Tyr Asn Val Phe
1               5                   10                  15

Thr Ser Phe His Gly Pro Asp Val Arg Ile Lys Phe Leu Ser His Leu
            20                  25                  30

His Gln Gln Phe Ile Tyr Asn Gly Ile Ser Met Phe Asp Asp Asn Gly
        35                  40                  45

Ile Glu Arg Ser Gln Ile Ala Pro Ala Leu Lys Lys Ala Met Gly
    50                  55                  60

Glu Ser Arg Ile Ile Ile Leu Leu Ser Lys Asn Tyr Ala Ser Ser
65                  70                  75                  80

Ser Trp Ser Leu Asp Glu Leu Leu Glu Ile Leu Lys Cys Arg Glu Asp
                85                  90                  95
```

```
Leu Gly Gln Ile Val Met Cys Val Phe Trp Asp Val Asp Pro Ser Asp
                100                 105                 110

Val His Gln Gln Cys Gly Asp Phe Gly Ile Ala Phe Lys Glu Thr Cys
            115                 120                 125

Ala His Lys Thr Glu Glu Glu Arg Gln Lys Trp Thr Gln Ala Leu Thr
    130                 135                 140

Tyr Val Gly Asn Ile Ala Gly Glu Asp Phe Lys His Trp Pro Asn Glu
145                 150                 155                 160

Ala Lys Met Ile Glu Lys Ile Gly Arg Asp Val Ser Glu Ile Leu Asn
                165                 170                 175

Val Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
    195                 200                 205

Ile Val Gly Ile Ser Gly Pro Ala Gly Ile Gly Lys Ser Thr Ile Ala
210                 215                 220

Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Met Asp Glu Tyr Arg
                245                 250                 255

Leu Lys Leu Lys Leu Gln Gln Gln Met Ile Ala Tyr Val Ala Asn Gln
            260                 265                 270

Asp Lys Ile Arg Val Gly His Leu Ser Val Met Lys Glu Arg Leu Asp
    275                 280                 285

Asp Leu Arg Val Leu Ile Ile Leu Asp Asp Val Glu His Leu Tyr Gln
    290                 295                 300

Ile Glu Met Ile Ala Asp Ile Arg Trp Phe Gly Pro Gly Ser Arg Val
305                 310                 315                 320

Ile Gly Thr Thr Glu Asn Arg Glu Ile Leu Leu Asn His Gly Ile Lys
                325                 330                 335

Asp Ile Tyr His Val Gly Phe Pro Ser Glu Gly Glu Ala Leu Met Ile
            340                 345                 350

Phe Cys Leu Ser Ala Phe Arg Gln Pro Thr Pro Pro Tyr Gly Phe Met
    355                 360                 365

Lys Leu Thr Tyr Glu Val Ala Ser Ile Cys Gly Asn Leu Pro Leu Gly
    370                 375                 380

Leu His Val Ala Gly Thr Leu Leu Trp Met Lys Ser Gln Ala Asp Trp
385                 390                 395                 400

Ile Glu Glu Leu Pro Arg Leu Lys Asp Cys Leu Asp Gly Arg Ile Glu
                405                 410                 415

Ser Val Leu Lys Val Gly Tyr Glu Ser Leu Tyr Glu Lys Asp Gln Ala
            420                 425                 430

Leu Phe Leu Leu Ile Ala Val Tyr Phe Asn Tyr Asp Tyr Val Asp Tyr
    435                 440                 445

Val Thr Ser Met Leu Glu Asn Thr Asn Val Leu Asp Val Arg Leu Gly
    450                 455                 460

Leu Lys Lys Leu Ala Asn Arg Ser Leu Ile Gln Ile Asp Ile Asp His
465                 470                 475                 480

Asn Arg Lys Ser His Val Val Met Asn Arg Leu Ala Asn Val Met Ala
                485                 490                 495

Arg Glu Val Ile Ser Lys Gln Lys Ile Ser Lys Arg Lys Ile Leu Asp
            500                 505                 510
```

```
Asp Pro Gln Asp Ile Cys Tyr Val Leu Asp Glu Ala Lys Val Lys Gly
            515                 520                 525

Ser Ala Leu Ala Leu Ser Leu Asp Val Ala Glu Ile Lys Glu Leu Val
    530                 535                 540

Ile Asn Lys Lys Ala Phe Lys Lys Met Cys Asn Leu Leu Ile Leu Lys
545                 550                 555                 560

Val Tyr Asn Gly Thr Asp Pro Arg Asp Ser Lys Leu His Val Pro Asp
                565                 570                 575

Glu Met Glu Leu Pro Thr Ser Ile Arg Leu Leu His Trp Glu Ala Tyr
            580                 585                 590

Pro Arg Lys Ser Phe Arg Phe Gly Pro Glu Asn Leu Val Thr Leu Asn
        595                 600                 605

Met Glu Tyr Ser Glu Leu Glu Lys Leu Trp Lys Gly Thr Gln Pro Leu
    610                 615                 620

Ala Asn Leu Lys Glu Met Asn Leu Cys Gly Ser Ser Cys Leu Lys Glu
625                 630                 635                 640

Leu Pro Asp Leu Ser Lys Ala Ala Asn Leu Glu Arg Leu Asp Val Ala
                645                 650                 655

Glu Cys Asn Ala Leu Val Glu Ile Pro Ser Ser Val Ala Asn Leu His
            660                 665                 670

Lys Ile Val Asn Leu His Met Glu Ser Cys Glu Ser Leu Glu Val Ile
        675                 680                 685

Pro Thr Leu Ile Asn Leu Ala Ser Leu Lys Ile Ile Asn Ile His Asp
    690                 695                 700

Cys Pro Arg Leu Lys Ser Phe Pro Asp Val Pro Thr Ser Leu Glu Glu
705                 710                 715                 720

Leu Val Ile Glu Lys Thr Gly Val Gln Glu Leu Pro Ala Ser Phe Arg
                725                 730                 735

His Cys Thr Gly Val Thr Thr Leu Tyr Ile Cys Ser Asn Arg Asn Leu
            740                 745                 750

Lys Thr Phe Ser Thr His Leu Pro Met Gly Leu Arg Lys Leu Asp Leu
        755                 760                 765

Ser Asn Cys Gly Ile Glu Trp Val Thr Asp Ser Ile Lys Asp Leu His
    770                 775                 780

Asn Leu Tyr Tyr Leu Lys Leu Ser Gly Cys Lys Arg Leu Val Ser Leu
785                 790                 795                 800

Pro Glu Leu Pro Cys Ser Leu Glu Cys Leu Phe Ala Glu Asp Cys Thr
                805                 810                 815

Ser Leu Glu Arg Val Ser Asp Ser Leu Asn Ile Pro Asn Ala Gln Trp
            820                 825                 830

Asn Phe Ile Lys Cys Phe Thr Leu Asp Arg Glu Ala Arg Ala Gly
        835                 840                 845

Ile Gln Gln Ser Phe Val His Gly Asn Val Ile Leu Pro Ala Arg Glu
    850                 855                 860

Val Leu Glu Glu Val Asp Tyr Arg Ala Arg Gly Asn Cys Leu Thr Ile
865                 870                 875                 880

Pro Pro Ser Ala Phe Asn Arg Phe Arg Val Cys Val Val Leu Ser Ile
                885                 890                 895

His

<210> SEQ ID NO 26
<211> LENGTH: 2691
<212> TYPE: DNA
<213> ORGANISM: Artificial Sequence
```

<220> FEATURE:
<221> NAME/KEY: source
<222> LOCATION: 1..2691
<223> OTHER INFORMATION: /organism="Artificial Sequence"
    /note="Nucleotide sequence HCP6, variant 8"
    /mol_type="unassigned DNA"

<400> SEQUENCE: 26

```
atggccagca gcagctgcag ccccagaaac tggagataca acgtgttcac cagcttccac      60
ggccccgacg tgagaatcaa gttcctgagc cacggcagac agcagttcat ctacaacggc     120
atcaccatgt tcgacgacaa cggcatcgag agaagccaga tcatcgcccc cgccctgaag     180
aaggccatcg cgacagcag aatcgccatc atgctgctga gcaagaacta cgccagcagc     240
agctggagcc tggaggagct gctggagatc ctgaagtgca aggaggacat cggccagatc     300
gtgatgaccg tgtggtacga ggtggacccc agcgacgtga cagcagac cggcgacttc      360
ggcatcgcct tcaaggagac ctgcgcccac aagaccgagg aggagagaca gaagtggacc     420
caggcccctga cctacgtggg caacatcgcc ggcgaggact caagcactg ccccaggag      480
gccaagatga tcgacaagat cgccagagac gtgagcgaca tcctgaacgt gaccccctgc     540
agagacttcg acggcatggt gggcctgaac gaccacctga gagagatgga gagcctgctg     600
gacctgaaga cgacggcgt gaagatcgtg ggcatcagcg gccccgccgg catcggcaag     660
agcaccatcg ccaccgccct gcacggcaga ctgagcaaca tgttccagag aacctgcttc     720
gtggacaacc tgagagagag ctacaagatc ggcctggacg agtggagact gaagctgcac     780
ctgcagcagc agctgctggc ctacgtgctg aaccaggaca agatcagagt gggccacctg     840
agcgtgatga aggagagact ggacgacctg agagtgctga tcatcctgga cgacgtggag     900
cacctgtacc agctggaggc cctgatggac atcagatggt tcggcccccgg cagcagagtg     960
atcgtgagca ccgagaacag agagatcctg ctgcagcacg gcatcaagga gatctaccac    1020
gtgggcttcc ccagcgaggg cgaggccctg atgatcttct gcctgagcgc cttcagacag    1080
cccagccccc cctacggctt cctgaagctg acctacgagg tggccagcat ctgcggcaac    1140
ctgcccctgg gcctgcacgt gctgggcacc ctgctgtggg gcaagagcca ggccgactgg    1200
atcgaggagc tgcccagact gaaggactgc ctggacggca aatcgagag cgtgctgaag    1260
gtgggctacg agagcctgta cgagaaggac caggccctgt cctgctgat cgccgtgtac    1320
ttcaactacg actacgtgga ctacgtgacc agcatgctgg agaacaccaa cgtgctggac    1380
gtgagactgg gcctgaagaa gctggccaac agatgcctga tccagatcga catcgagcac    1440
cagagaaaga gcagagtggt gatgaacaga ctgctgcagg tgatcgccag agaggtgatc    1500
agccaccaga aggtgagcaa gagaaagatc ctggaggacc ccaggacgt gtgctacgtg    1560
ctggaggagg ccaagggcaa gggcaccgcc ctgggcctga gctggacgt ggccgagatc    1620
aaggagctgg tgatcaacaa gaaggccttc aagagaatgt gcaacctgct gatcctgaag    1680
gtgttcaacg gcaccgaccc cagagacagc aagctgcacg tgcccgagga gatggagctg    1740
cccagcagca tcagactgct gcactgggag gccttcccca aaagagctt cagattcggc    1800
cccgagaacc tggtgaccct gaacatggag tacagcgagc tggagaagct gtggaagggc    1860
acccagcccc tggccaacct gaaggagatg aacctgtgcg cagcagctg cctgaaggag    1920
ctgcccgacc tgagcaaggc cgccaacctg gagagactgg acgtggccga gtgcaacgcc    1980
ctggtggaga tccccagcag cgtggccaac ctgcacaaga tcgtgaacct gcacatggag    2040
agctgcgaga gcctggaggt gatccccacc ctgatcaacc tggccagcct gaagatcatc    2100
```

-continued

```
aacatccacg actgccccag actgaagagc ttccccgacg tgcccaccag cctggaggag    2160
ctggtgatcg agaagaccgg cgtgcaggag ctgcccgcca gcttcagaca ctgcaccggc    2220
gtgaccaccc tgtacatctg cagcaacaga aacctgaaga ccttcagcac ccacctgccc    2280
atgggcctga aaagctggaa cctgagcaac tgcggcatcg agtgggtgac cgacagcatc    2340
aaggacctgc acaacctgta ctacctgaag ctgagcggct gcaagagact ggtgagcctg    2400
cccgagctgc cctgcagcct ggagtgcctg ttcgccgagg actgcaccag cctggagaga    2460
gtgagcgaca gcctgaacat ccccaacgcc cagttcaact tcatcaagtg cttcacccctg   2520 gacagagagg ccagaagagc catcatccag cagagcttcg tgcacggcaa cgtgatcctg    2580 ccctgagag aggtgctgga ggaggtggac tacagagcca gaggcaactg cctgaccatc     2640
ccccccagcg ccttcaacag atacaaggtg tgcgtggtgc tgaccatcca c             2691
```

<210> SEQ ID NO 27
<211> LENGTH: 897
<212> TYPE: PRT
<213> ORGANISM: Artificial Sequence
<220> FEATURE:
<223> OTHER INFORMATION: Amino acid sequence HCP6, variant 8

<400> SEQUENCE: 27

```
Met Ala Ser Ser Cys Ser Pro Arg Asn Trp Arg Tyr Asn Val Phe
1               5                   10                  15

Thr Ser Phe His Gly Pro Asp Val Arg Ile Lys Phe Leu Ser His Gly
            20                  25                  30

Arg Gln Gln Phe Ile Tyr Asn Gly Ile Thr Met Phe Asp Asp Asn Gly
        35                  40                  45

Ile Glu Arg Ser Gln Ile Ile Ala Pro Ala Leu Lys Lys Ala Ile Gly
    50                  55                  60

Asp Ser Arg Ile Ala Ile Met Leu Leu Ser Lys Asn Tyr Ala Ser Ser
65                  70                  75                  80

Ser Trp Ser Leu Glu Glu Leu Leu Glu Ile Leu Lys Cys Lys Glu Asp
                85                  90                  95

Ile Gly Gln Ile Val Met Thr Val Trp Tyr Glu Val Asp Pro Ser Asp
            100                 105                 110

Val Arg Gln Gln Thr Gly Asp Phe Gly Ile Ala Phe Lys Glu Thr Cys
        115                 120                 125

Ala His Lys Thr Glu Glu Arg Gln Lys Trp Thr Gln Ala Leu Thr
    130                 135                 140

Tyr Val Gly Asn Ile Ala Gly Glu Asp Phe Lys His Trp Pro Gln Glu
145                 150                 155                 160

Ala Lys Met Ile Asp Lys Ile Ala Arg Asp Val Ser Asp Ile Leu Asn
                165                 170                 175

Val Thr Pro Cys Arg Asp Phe Asp Gly Met Val Gly Leu Asn Asp His
            180                 185                 190

Leu Arg Glu Met Glu Ser Leu Leu Asp Leu Lys Asn Asp Gly Val Lys
        195                 200                 205

Ile Val Gly Ile Ser Gly Pro Ala Gly Ile Gly Lys Ser Thr Ile Ala
    210                 215                 220

Thr Ala Leu His Gly Arg Leu Ser Asn Met Phe Gln Arg Thr Cys Phe
225                 230                 235                 240

Val Asp Asn Leu Arg Glu Ser Tyr Lys Ile Gly Leu Asp Glu Trp Arg
                245                 250                 255

Leu Lys Leu His Leu Gln Gln Gln Leu Leu Ala Tyr Val Leu Asn Gln
```

```
                260                 265                 270
Asp Lys Ile Arg Val Gly His Leu Ser Val Met Lys Glu Arg Leu Asp
            275                 280                 285
Asp Leu Arg Val Leu Ile Ile Leu Asp Asp Val Glu His Leu Tyr Gln
            290                 295                 300
Leu Glu Ala Leu Met Asp Ile Arg Trp Phe Gly Pro Gly Ser Arg Val
305                 310                 315                 320
Ile Val Ser Thr Glu Asn Arg Glu Ile Leu Gln His Gly Ile Lys
                325                 330                 335
Glu Ile Tyr His Val Gly Phe Pro Ser Glu Gly Glu Ala Leu Met Ile
                340                 345                 350
Phe Cys Leu Ser Ala Phe Arg Gln Pro Ser Pro Tyr Gly Phe Leu
        355                 360                 365
Lys Leu Thr Tyr Glu Val Ala Ser Ile Cys Gly Asn Leu Pro Leu Gly
            370                 375                 380
Leu His Val Leu Gly Thr Leu Trp Gly Lys Ser Gln Ala Asp Trp
385                 390                 395                 400
Ile Glu Glu Leu Pro Arg Leu Lys Asp Cys Leu Asp Gly Arg Ile Glu
                405                 410                 415
Ser Val Leu Lys Val Gly Tyr Glu Ser Leu Tyr Glu Lys Asp Gln Ala
                420                 425                 430
Leu Phe Leu Leu Ile Ala Val Tyr Phe Asn Tyr Asp Tyr Val Asp Tyr
            435                 440                 445
Val Thr Ser Met Leu Glu Asn Thr Asn Val Leu Asp Val Arg Leu Gly
            450                 455                 460
Leu Lys Lys Leu Ala Asn Arg Cys Leu Ile Gln Ile Asp Ile Glu His
465                 470                 475                 480
Gln Arg Lys Ser Arg Val Val Met Asn Arg Leu Leu Gln Val Ile Ala
                485                 490                 495
Arg Glu Val Ile Ser His Gln Lys Val Ser Arg Lys Ile Leu Glu
            500                 505                 510
Asp Pro Gln Asp Val Cys Tyr Val Leu Glu Glu Ala Lys Gly Lys Gly
            515                 520                 525
Thr Ala Leu Gly Leu Ser Leu Asp Val Ala Glu Ile Lys Glu Leu Val
            530                 535                 540
Ile Asn Lys Lys Ala Phe Lys Arg Met Cys Asn Leu Leu Ile Leu Lys
545                 550                 555                 560
Val Phe Asn Gly Thr Asp Pro Arg Asp Ser Lys Leu His Val Pro Glu
                565                 570                 575
Glu Met Glu Leu Pro Ser Ser Ile Arg Leu Leu His Trp Glu Ala Phe
            580                 585                 590
Pro Arg Lys Ser Phe Arg Phe Gly Pro Glu Asn Leu Val Thr Leu Asn
            595                 600                 605
Met Glu Tyr Ser Glu Leu Glu Lys Leu Trp Lys Gly Thr Gln Pro Leu
            610                 615                 620
Ala Asn Leu Lys Glu Met Asn Leu Cys Gly Ser Ser Cys Leu Lys Glu
625                 630                 635                 640
Leu Pro Asp Leu Ser Lys Ala Ala Asn Leu Glu Arg Leu Asp Val Ala
                645                 650                 655
Glu Cys Asn Ala Leu Val Glu Ile Pro Ser Ser Val Ala Asn Leu His
                660                 665                 670
Lys Ile Val Asn Leu His Met Glu Ser Cys Glu Ser Leu Glu Val Ile
            675                 680                 685
```

```
Pro Thr Leu Ile Asn Leu Ala Ser Leu Lys Ile Ile Asn Ile His Asp
    690                 695                 700
Cys Pro Arg Leu Lys Ser Phe Pro Asp Val Pro Thr Ser Leu Glu Glu
705                 710                 715                 720
Leu Val Ile Glu Lys Thr Gly Val Gln Glu Leu Pro Ala Ser Phe Arg
                725                 730                 735
His Cys Thr Gly Val Thr Thr Leu Tyr Ile Cys Ser Asn Arg Asn Leu
            740                 745                 750
Lys Thr Phe Ser Thr His Leu Pro Met Gly Leu Arg Lys Leu Asp Leu
        755                 760                 765
Ser Asn Cys Gly Ile Glu Trp Val Thr Asp Ser Ile Lys Asp Leu His
770                 775                 780
Asn Leu Tyr Tyr Leu Lys Leu Ser Gly Cys Lys Arg Leu Val Ser Leu
785                 790                 795                 800
Pro Glu Leu Pro Cys Ser Leu Glu Cys Leu Phe Ala Glu Asp Cys Thr
                805                 810                 815
Ser Leu Glu Arg Val Ser Asp Ser Leu Asn Ile Pro Asn Ala Gln Phe
            820                 825                 830
Asn Phe Ile Lys Cys Phe Thr Leu Asp Arg Glu Ala Arg Arg Ala Ile
        835                 840                 845
Ile Gln Gln Ser Phe Val His Gly Asn Val Ile Leu Pro Leu Arg Glu
850                 855                 860
Val Leu Glu Glu Val Asp Tyr Arg Ala Arg Gly Asn Cys Leu Thr Ile
865                 870                 875                 880
Pro Pro Ser Ala Phe Asn Arg Tyr Lys Val Cys Val Val Leu Thr Ile
                885                 890                 895
His
```

<210> SEQ ID NO 28
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
      /note="Nucleotide sequence HCP6, variant 9"
      /mol_type="unassigned DNA"

<400> SEQUENCE: 28

```
atggcctcct cctcgtcgtc cccacgaaat tggagataca atgtgtttac gtcgttccac    60
ggtcctgatg tccgaataaa atttttgtcc catcttaggc aacaattcat atacaatggt   120
ataaccatgt tcgatgacaa tggaatagaa cgctcgcaaa tcatagctcc tgccttgaaa   180
aaagcgatag gtgaatcgcg gatagcaatt atgttactat ccaaaaatta tgcgtcatcg   240
tcctggagct tggatgaatt gcttgaaata ctaaaatgca aggaggacat agggcaaata   300
gtaatgactg tattttatga agtcgatccg tctgatgtac gcaaccaaac aggggacttt   360
ggaatagcgt tcaaggaaac gtgcgcacat aagacggagg aagagcgcca gaagtggacg   420
caagccttaa cgtatgtcgg gaacatagct ggagaagatt caaacattg gcccaatgag   480
gcaaaaatga ttgaaaaaat agccagagat gtaagtgaca ttctgaatgt gacgccctgc   540
agagattttg atggtatggt aggcctaaat gaccatttac gtgaaatgga gtccctttg    600
gatctaaaaa atgatggagt aaaaattgtt gggatcagcg tccggccgg cataggcaaa   660
tcgaccatcg caacagccct gcatgggcgc ctctcaaaca tgttccaaag gacgtgtttt   720
```

```
gtcgacaatc tgagggaatc gtacaaaatt ggtttagatg aataccggct caaactccat      780
ctccaacaac aactgatggc gtatgtcctg aaccaagaca aaatccgtgt gggacatctg      840
agcgttatga aggagcgact cgatgatcta cgcgtaatga taatcctgga tgatgtagaa      900
catttgtacc agttagaggc cctcgcagac atacgttggt ttggccctgg gtcacgtgta      960
attgtaacaa cagaaaaccg cgaaattcta ctccaacatg gcatcaaaga catttatcat     1020
gtcggttttc catccgaggg agaggctctt atgatttttt gtttgtccgc gttccgtcaa     1080
cccagccccc catatggttt tttaaaactg acatatgagg tcgcgtctat ttgtggaaat     1140
ctccctcttg gtctgcatgt catgggaact ctcatgtggg gaaaatcaca agccgactgg     1200
atagaagagc taccgcgtct aaaagactgt ttggatggcc gcatagagtc cgttctaaaa     1260
gtaggttatg aaagtctata tgaaaaagac caagcgttgt ttttactcat agcggtctat     1320
ttcaattatg attatgttga ttatgttaca tcgatgctag aaaatacgaa tgtcttagat     1380
gtgcgcttag gattaaaaaa actcgcaaat agatgcatga tacaaatcga cattgaccat     1440
aatagaaaat cgcgcgtagt aatgaatcgg ttactgcaag ttatggcccg agaggttatc     1500
agcaaacaaa aaatcagcaa aagaaaaata ttggaagatc cgcaagacat atgttatgtc     1560
atggaggaag cgaaaggaaa agggtctgcg ctaggtttat cgctcgatgt ggcagaaata     1620
aaagagctcg tcattaataa aaaggcgttc aaaaaaatgt gcaatttgat gattttgaag     1680
gtgttcaatg gaactgatcc gagagattca aaattgcatg tacccgagga atggagatg      1740 ccctcctcga tccgcatgct acattgggaa gcgtaccccc gtaaaagctt ccggtttgga     1800
cccgaaaatt tagtaacgct aaacatggag tatagtgaac tggaaaaatt atggaaaggg     1860
acgcaacctc tagccaatct caaagaaatg aatttgtgtg gttcgtcgtg tctcaaggaa     1920
ttacctgacc tgagtaaagc agcgaatcta gaacgtttag atgtggcgga atgcaatgcc     1980
ttggtcgaaa taccgtcttc agtcgcaaat ctccataaaa ttgtgaacct ccatatggag     2040
tcatgtgaat cactagaagt gatcccaacc ttgataaatt tagcatctct taaaatcatc     2100
aatattcatg attgtccgcg gctgaaatcg tttcctgacg tccccacctc actagaagag     2160
atggtcatcg agaaaactgg tgtacaggaa ctgcctgcgt ctttcaggca ttgtacaggc     2220
gttaccactc tgtacatttg ctcaaacagg aatctaaaaa cgttctccac gcatttaccc     2280
atgggtttga gaaaactcga tctatcgaat tgtggaattg aatgggtcac tgattcgata     2340
aaagatctcc acaatctgta ttatctaaaa ttatcgggat gcaaacgttt ggtctcctta     2400
ccggagctcc catgtagctt agagtgtctt tttgcggaag actgtactag cctcgaaagg     2460
gtgtcagatt cactaaacat acccaatgcg caattcaact tcataaaatg ttttacacta     2520
gaccgagagc cgagacgagc tataatacaa caaagttttg tccatgggaa cgttatactt     2580
cccgcacggg aagtcctaga ggaagtggat taccgagcga gaggtaattg tcttacaatt     2640
cctcccagcg ctttcaacag attcaaggtc tgtgtcgtac tttccattca ctag           2694
```

<210> SEQ ID NO 29
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
     /note="Nucleotide sequence HCP6, variant 10"
     /mol_type="unassigned DNA"

```
<400> SEQUENCE: 29
atggcctcca gttcatctag tccgagaaat tggagatata atgtctttac ttctttccat      60
ggtcccgatg taaggatcaa attcctaagt catctgcgcc aacaattcat ttacaatgga     120
attacaatgt ttgatgacaa tggaatagaa agaagccaaa ttattgctcc cgctctcaaa     180
aaagcgattg gagaatctag aatagccatc atgctgctta gtaagaatta tgcctcatct     240
tcctggagtt tggatgaact cctcgagatt ctaaaatgca aggaagatat tggccaaata     300
gtgatgacag tcttttatga agtggatccc tccgatgttc gcaatcaaac cggtgacttc     360
ggcatagcgt tcaaggagac atgtgctcat aaaactgagg aagagcgtca gaagtggacc     420
caagcattaa cctatgttgg taatatagcg ggggaagact ttaaacactg gccaaatgag     480
gcaaaaatga ttgaaaaaat tgccagggat gtaagtgaca tactcaacgt aaccccttgc     540
agagattttg atgggatggt tggcctcaat gaccatttac gggaaatgga gtcactgctc     600
gatttgaaaa atgacggagt caaaattgtt ggaatctctg gccggccgg cataggtaaa     660 agcacaatag ctacggccct gcatggtcgc cttagcaaca tgttccaacg gacctgtttt     720
gtagacaatc tacgtgaatc ttacaaaatt gggcttgatg aataccgtct taaacttcat     780
ctacagcaac aacttatggc ctatgtcctt aatcaagaca aaattcgggt gggacatctc     840
tcagtaatga agagcgcct tgacgacttg cgggttatga tcattctgga cgatgtcgaa     900
catttgtacc aactcgaggc cttggctgat ataaggtggt tgggcctgg ctctagagtc     960 attgtaacaa cagaaaatcg agaaatctta cttcaacacg gcatcaaaga catttaccat    1020
gtcggatttc cttcggaggg tgaagcactg atgatattct gtctttccgc ctttaggcaa    1080
ccctcacccc cttatggttt tctgaaatta acttatgagg ttgcctctat ctgtgggaat    1140
ctaccgttgg gcttacatgt gatgggaact cttatgtggg gtaaatctca agccgactgg    1200
atcgaagagc taccgcgtct gaaggactgt ttagatggaa ggattgagtc tgtgttgaag    1260
gtaggttatg agagtctata tgaaaaagac caggctctct ttctactaat agccgtttat    1320
tttaattacg attatgtgga ctatgtcaca tctatgctcg aaaataccaa tgtcctcgat    1380
gttcgactcg gacttaaaaa actggccaat cgatgtatga tacaaataga catcgaccac    1440
aatcgcaaga gcagggtcgt aatgaacagg ttacttcagg tcatggctag ggaggtcatt    1500
tcaaaacaaa aaataagcaa acggaaaatt ttagaagatc cgcaagacat ttgctatgtt    1560
ttggaggaag ccaaaggtaa gggtagtgct ctcggccttt ccctagacgt tgctgaaatc    1620
aaggagctgg ttatcaataa aaaggcgttc aaaaaaatgt gcaatctgat gatactaaag    1680
gtcttcaacg gcaccgatcc tcgggattcc aaattgcatg ttccagagga atggaaatg    1740 ccctcctcca ttaggatgct gcattgggaa gcttatccaa gaaatctttt cagatttggc    1800
ccggaaaatc ttgttactct aaacatggaa tatagtgagc tggaaaaatt gtggaagg    1860 acccagccgc ttgcgaattt gaaggaaatg aatctctgtg gtcgtcgtg tttgaaggaa    1920 ttgccggacc tgtcaaaggc tgctaatctt gaaagactgg atgtcgctga atgcaatgca    1980
ctagtagaga ttccatcaag tgtggcgaat cttcacaaaa ttgttaatct ccatatggaa    2040
tcctgcgagt cgctggaagt aatacctacg ctgataaatt tagctagtct caagataatt    2100
aatattcatg attgtcctag actgaaatcg tttccggacg ttccgacctc gttggaggag    2160
atggtgattg aaaaaacggg ggttcaggaa atgcccgcga gcttcagaca ttgcaccggc    2220
gtgacaacct tgtatatatg ttctaatcgt aatctaaaaa ctttcagtac gcatctaccg    2280
atgggcctga ggaaactaga cctaagcaat tgtggcatag aatgggtaac tgattccata    2340
```

```
aaggatctac ataatctgta ttatcttaaa ctttcagggt gcaaacgact ggtaagcctt    2400
cctgaacttc cgtgctcact ggaatgtctg tttgcgagg actgtacctc tttagagcgc    2460
gtcagcgatt ctcttaatat accgaacgcc caattcaatt tcatcaaatg tttcaccctg    2520
gaccgtgagg cccgacgggc tatcatccaa caaagttttg ttcatgggaa tgtaatactg    2580
cccgcgaggg aagtgctaga ggaagtcgac taccgcgcac gcgggaactg tctaacaatt    2640
cccccgtccg cgttcaaccg tttcaaagtc tgtgtggtcc tttcaataca ctga          2694
```

<210> SEQ ID NO 30
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
      /note="Nucleotide sequence HCP6, variant 11"
      /mol_type="unassigned DNA"

<400> SEQUENCE: 30

```
atggcttctt cgagttcttc gcctaggaac tggaggtaca acgtgtttac gagcttccat      60
ggccctgacg ttcgcattaa gtttctatcc cacttgaggc aacaattcat atacaacggg     120
atcactatgt tcgatgacaa tgggatcgaa cgcagtcaaa tcatcgcacc tgctctgaag     180
aaagccatag gggaatctag aattgcaata atgctgttat ctaagaacta tgcctcttct     240
tcgtggtcac tcgatgagtt gctcgagata cttaaatgca agaagacat cggtcagatc      300 gtaatgaccg ttttttatga agttgatcct tcggatgtac gaaatcagac cggagacttt    360
ggaatcgcct tcaaggaaac gtgcgctcat aaaaccgaag aagagagaca gaaatggacc    420
caggcgctta cctacgttgg gaacatagcg ggtgaagact ttaagcactg gcctaatgag    480
gcaaaaatga ttgagaaaat cgccagagat gtcagtgaca tcttaaatgt gactccatgc    540
agggactttg atggaatggt cggattgaat gaccatctca gggaaatgga gagccttctg    600
gaccttaaaa atgacggtgt aaagattgtg gggataagtg gaccccgctgg gatcggcaag    660 tcgacaattg ctacagctct gcatgggagg cttagtaaca tgttccagag gacatgctttt    720 gttgataatc ttagagagtc ctacaaaatt ggccttgatg agtacaggtt aaaacttcat    780
ctccaacagc aactttttgc gtatgtgtta aatcaagaca agatcagagt tggtcatctt    840
tccgtgatga aagagcgact cgacgacctc agagtaatga tcatactcga cgatgtagag    900
catttatacc aactagaggc tctcgcagac attaggtggt tcggaccggg atctagagtg    960
attgtcacga cggagaatag ggagatcctc ttgcaacatg gtattaaaga catttaccac   1020
gtagggtttc cctcagaggg cgaagctctg atgatatttt gtctttcggc gttccgccaa   1080
ccgagtccgc catatggatt tcttaagctc acctatgaag ttgcatccat ttgtggcaat   1140
cttccattgg gactacatgt tttgggaact ctaatgtggg gtaaaagtca agccgactgg   1200
atagaagagc tacctaggct gaaagattgt ctagacggta gaattgaaag tgtgctaaag   1260
gtaggatatg agtcactcta tgagaaagac caggctctat ttctgctcat cgctgtatat   1320
tttaactatg attatgttga ttatgtgacg tctatgctgg aaaatacgaa tgtattggat   1380
gtgaggctgg gtctcaagaa acttgcgaac cgttgcatga tccaaattga cattgaccat   1440
aatcgtaagt cccgcgttgt gatgaacagg cttcttcagg tgatggccag ggaagtaata   1500
agtaagcaaa agatttcgaa aaggaaaatt ctagaggatc ctcaagacat ctgttacgta   1560
```

```
atggaggagg ctaaagggaa aggatcagcg ctgggtctat cattggatgt tgcagaaatt      1620
aaggaactcg ttattaacaa aaaggccttc aagaagatgt gcaacttaat gattctaaaa      1680
gtgtttaatg gcacagatcc gcgggactcc aagcttcatg taccagagga gatggagatg      1740
cccagctcca tccgtatgtt gcattgggaa gcttatccca ggaagtcttt tagatttggc      1800
cccgaaaatt tagttactct aaatatggaa tactcggaat tggagaaact ttggaaggga      1860
acccagcctc tggctaatct gaaggagatg aatctttgcg ggagtagttg tttaaaagaa      1920
ctgcctgatc tgtccaaagc agctaatctg gaaaggcttg atgttgcaga gtgcaatgcg      1980
ctagttgaaa tcccgagttc cgtggcgaac cttcataaga tagtcaatct tcatatggag      2040
tcatgcgaat cactcgaagt aattcccacc cttataaacc tcgcttctct gaagattatt      2100
aatattcatg actgtccaag attgaaatcc tttccggatg ttcctaccag cctagaggag      2160
atggttatag agaagactgg cgtacaggag atgcctgcga gtttccgaca ctgcacaggt      2220
gtgaccaccc tctacatctg tagcaacaga aaccttaaaa cattctctac acacctcccg      2280
atgggcctgc gcaaacttga tctttcaaat tgcggcatcg aatgggtgac ggactcaatc      2340
aaagatcttc ataatctgta ttatttgaag ttatccggat gcaagcgact agtgagcctt      2400
ccagagctcc cgtgttcact tgagtgtttg ttcgcggagg attgtactag tttggaacgt      2460
gtatccgact cacttaatat accgaacgct cagtttaact tcataaaatg tttcacgctc      2520
gacagagaag ctaggcgggc tatcatacaa cagagcttcg tccacggaaa cgtcatacta      2580
ccagctcgtg aagttctcga agaagtcgac tatcgggccc gtgggaattg cctgaccata      2640
ccgcctagcg cattcaatcg gtttaaagtg tgtgtggttc tctcaatcca ctga            2694
```

<210> SEQ ID NO 31
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
    /note="Nucleotide sequence HCP6, variant 12"
    /mol_type="unassigned DNA"

<400> SEQUENCE: 31

```
atggcttcgt ctagcagctc gcctcgaaac tggcgttata atgtcttcac ttctttccac       60
gggcctgatg ttaggatcaa gttcctatct catcttaggc aacaattcat atacaatggg      120
atcactatgt tcgacgacaa tggaatcgag cgtagtcaga ttatcgcccc ggcgttgaaa      180
aaagcgatcg gcgaatcaag gattgctata ctgctcctta gtaaaaacta tgctagcagt      240
agttggtcat tagatgaact tctcgagatc ctgaagtgta aagaagacat tggtcaaatc      300
gtgatgacgg ttttctatga ggtagacccc tccgatgtgc gaaaccaaac gggcgatttt      360
gggatagcat tcaaagaaac ctgcgcgcac aagacagaag aagaacgtca aaagtggact      420
caagccctta cctacgtggg caatatagcc ggagaagatt ttaaacattg gcctaatgag      480
gcgaagatga tcgagaagat agctagggat gttagcgaca tccttaacgt gacaccgtgt      540
cgtgactttg atggcatggt agggctaaat gatcatcttc gcgagatgga atccctctta      600
gacttaaaga acgacggtgt taaaattgta ggaatttctg gaccagctgg aatcggaaaa      660
tctactatcg ccactgcgct tcacggtcgt cttcgaaca tgttccagag gacgtgtttt      720
gtggataacc ttagagagtc ctacaagata ggtctcgatg agtataggct taagctgcac      780
cttcagcagc aattgttggc ctacgtgctt aaccaagata agatcagagt cggacattta      840
```

```
tccgtcatga aggaacgcct cgacgatttg agggtgctga taattttgga cgatgttgag     900
cacctctatc aacttgaggc tctcgcggat attaggtggt tcggacccgg atctaggtg      960 atagtgacta ccgagaaccg ggagatactt ttacagcatg ggataaagga catctatcat    1020
gtgggcttcc cgtctgaagg tgaggctctt atgatatttt gtctatccgc atttagacag    1080
ccttcacctc cttatggatt cctgaaactc acctatgaag tggcgagtat atgtggtaac    1140
ttaccactgg gccttcacgt attgggaacc ctattgtggg gtaaatcgca agctgattgg    1200
atcgaagagc tgcctcgact taaagactgt cttgacggta gaattgaatc cgtattgaaa    1260
gtgggctatg agtcactcta tgagaaagat caggcattgt tcctccttat cgcggtatac    1320
tttaattacg attatgtgga ctatgtgacc agtatgctcg agaacaccaa cgttctcgat    1380
gtgaggctcg ggcttaaaaa gcttgcgaac cgttgcctga tacaaattga cattgaccat    1440
aaccgtaagt cacgtgtagt gatgaacaga ttgctacaag taatggcaag ggaagtgatt    1500
tcaaagcaaa aaattagtaa acgtaaaatc ctcgaggatc ctcaagacat ctgttacgtc    1560
atggaagagg ccaaaggtaa aggatcagcg ctcggcctta gtcttgacgt tgcagagatt    1620
aaggagttgg ttattaacaa aaaagctttt aaaaagatgt gtaatctcct gatccttaaa    1680
gttttcaacg gcaccgaccc tagagattct aagctgcacg ttccagaaga aatggaaatg    1740
ccttctagca tcagaatgct ccactgggag gcttacccta ggaaatcttt ccgtttcggt    1800
ccagagaacc tcgtcacact caatatggag tactcagagc tggagaagct ttggaaggga    1860
actcaaccat tagctaacct caaggagatg aacctctgcg gctccagttg cttgaaggaa    1920
ctcccagatc ttagtaaggc tgccaattta gaaaggcttg atgttgcaga atgtaatgct    1980
ctcgtcgaga tcccttcatc agtagctaat ttacataaga tcgttaacct tcatatggaa    2040
tcgtgtgaaa gccttgaagt tatcccgacg cttataaatt tagccagcct aaagataata    2100
aacattcacg actgtcctcg gctaaagagc tttccagacg tgcctacttc tttagaagaa    2160
atggtaattg agaagacagg cgttcaggaa atgcccgcgt cgtttagaca ttgcacgggt    2220
gtgactacgt tatacatctg cagtaatcga aacctgaaaa cttttagtac tcatctgccg    2280
atgggcctta ggaagctcga tcttagtaac tgcgggatcg aatgggtcac tgactctata    2340
aaagacctgc ataatctcta ctaccttaag cttagcggtt gtaagaggct cgtttcgctc    2400
ccagaacttc cgtgcagcct tgagtgccta ttcgctgagg attgcacttc gcttgaaagg    2460
gtttcggact cgctgaatat ccctaacgcc cagtttaact tcataaagtg tttcaccctc    2520
gatagggaag cgaggcgtgc gatcattcaa cagagctttg tacatggcaa cgtgattcta    2580
cctgcacgtg aggtcctcga ggaggttgat tatcgagcta gagggaactg cctaactatc    2640
cctccttcag ccttcaatag gttcaaggta tgcgtggtgc tatcgataca ttga          2694
```

<210> SEQ ID NO 32
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
    /note="Nucleotide sequence HCP6, variant 13"
    /mol_type="unassigned DNA"

<400> SEQUENCE: 32

```
atggctagct ctagctctag tcctaggaac tggcgttata acgtgtttac tagcttccac     60
```

```
ggcccagacg taaggattaa gtttttgagt caccttaggc aacaatttat ctataacggg    120
ataactatgt tcgatgataa cgggatcgag cgttctcaaa ttatagctcc agctcttaag    180
aaagccatcg gcgagtctag gatcgcaatc atgctcctta gtaaaaatta cgctagctcc    240
tcctggagtc tcgacgagct gctcgagatc ttaaaatgca aggaggacat cggtcagata    300
gtgatgaccg tattctacga ggttgaccct tcagatgtca ggaatcagac tggagatttc    360
gggatcgcct ttaaggagac ttgcgctcat aaaaccgagg aggaacgaca aaagtggact    420
caagcgctta cttacgttgg taacattgcc ggagaagact ttaagcactg gccaaacgaa    480
gctaagatga tcgagaagat agcacgagac gttagcgata tccttaatgt gaccccatgt    540
agggactttg acggaatggt tggactgaat gaccaccttg agaaatggga atcacttttta   600 gaccttaaga acgatggcgt taaaatcgtg ggtatctcag gcccagctgg tatcggtaag    660
agtactatcg ctacagctct tcacgggcga cttagtaata tgtttcagag gacctgcttc    720
gttgacaacc ttagagagtc gtataagata ggcctcgacg agtataggct taagcttcac    780
ttacagcagc agctaatggc ctatgtcctt aatcaggaca agattagagt gggacatctt    840
agcgtcatga agaaaggtt agacgatctt agggtcctga taattctcga cgacgtcgag     900
cacctctatc agcttgaagc tcttgcagat attaggtggt tcggaccagg atctagggtg    960
atcgtgacga ctgagaatag ggagatcctc ctccaacacg gcattaagga tatttatcat   1020
gttggcttcc ctagcaaagg tgaggctctc atgatcttct gcctaagcgc gtttaggcaa   1080
cccagtccac cttacggatt ccttaagttg acttacgaag tggcgagtat ctgtggtaac   1140
cttccacttg ggttgcacgt attggggaca cttttgtggg gtaaatccca agcagattgg   1200
atcgaagagt tgcctcgatt gaaggactgt ctcgacgggc gcattgagtc agttcttaaa   1260
gtcgggtacg aatcactgta tgagaaggac caagctctct ttctccttat agccgtttac   1320
tttaattacg actacgtaga ttacgtgacc tccatgttgg agaacactaa cgtgctcgat   1380
gttcgactcg gccttaaaaa acttgctaac cgttgcctga ttcagataga tatcgatcac   1440
aaccgtaaat ctcgagttgt gatgaaccgt ctccttcagg tgatggctcg agaagtgata   1500
agtaaacaga aaattagtaa gcgtaagatc ctcgaggacc ctcaggacat atgttatgtg   1560
ttggaagagg ctaagggcaa gggatcagca ctgggacttt cacttgacgt ggccgagatt   1620
aaggagctag tgattaataa aaaagccttt aaaaagatgt gcaacctcct gatattaaaa   1680
gtgtttaacg gtaccgaccc tagggattct aagttacacg ttccagagga gatggaactg   1740
ccgagctcta ttaggctgct gcattgggag gcttatccta ggaagtcttt tcgtttcggg   1800
cccgaaaatc tcgtgacact taatatggag tactcagaac ttgagaaact ttggaaggga   1860
actcagccac tcgctaattt aaaagagatg aacctctgcg gctcttcgtg tcttaaagaa   1920
ctaccagact tgagtaaagc cgctaacttg gagaggcttg atgttgcaga gtgcaatgct   1980
ctcgttgaaa tcccgtcctc agtagccaat cttcacaaaa ttgtgaatct tcacatggaa   2040
tcctgcgagt cactcgaagt tatccctacc cttattaatt tagctagctt aaagattata   2100
aatattcacg actgcccaag actaaagtcc tttccagatg tacccactag ccttgaggaa   2160
ctggtgatcg aaaagaccgg cgtccaagaa ctgcccgcta gttttcgcca ctgtacaggc   2220
gtgactacac tctatatatg ttctaatcgt aatcttaaaa cctttagcac tcacctcccg   2280
atgggtctta ggaaactcga tcttagtaac tgcggaatcg agtgggttac cgactctatt   2340
aaggatcttc acaacctcta ctaccttaag ctttcgggct gtaagaggct cgttagcctc   2400
ccagaacttc catgctcact tgaatgcctc ttcgctgagg attgcactag tcttgagcgt   2460
```

-continued

```
gtcagcgact cattaaacat acctaatgcg cagtttaatt ttattaagtg tttcaccctc    2520
gatcgcgagg ctaggcgtgc tatcattcag caatccttcg tccacggtaa cgtgatcctt    2580
ccagctcgag aggtattgga ggaggtggac tatagagcta ggggaaactg cctcactatc    2640 cccctagtg cctttaatag attcaaggtg tgcgtagtcc tctcaattca ctaa           2694
```

```
<210> SEQ ID NO 33
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
      /note="Nucleotide sequence HCP6, variant 14"
      /mol_type="unassigned DNA"

<400> SEQUENCE: 33
```

```
atggcttctt ctagctctag tcccaggaac tggcgttata atgtgttcac ttcttttcac     60
ggtccagatg tcaggattaa gttccttagt catcttaggc aacaatttat ctataacggg    120
atcactatgt tcgacgataa cgggattgag agaagtcaaa taatagctcc agctcttaag    180
aaggctatag gggagtcgag gattgctatc atgctccttt caaagaatta cgcgagctct    240
agttggtcac tcgacgaact tctcgagatc cttaagtgta aagaggatat cggtcaaatc    300
gtgatgaccg tgttctacga agtagaccct agcgacgtca ggaaccagac cggcgacttc    360
gggatcgcat ttaaggagac ttgcgctcat aagaccgaag aggaacgtca aaaatggacc    420
caggctctaa cctacgtggg taatattgcc ggcgaggact caaacattg gccgaacgag     480 gctaaaatga tcgagaagat cgctagggat gttagcgata tccttaacgt gacccttgt     540 agggacttcg acgggatggt tggacttaac gatcaccta gagagatgga atcattgctc     600
gaccttaaga cgacggcgt taagatcgtg ggaattagtg gaccagctgg gataggtaag     660
tctactattg ctactgccct tcacgggagg ttaagtaata tgttccagag gacctgcttt    720
gtggataatc ttcgcgagtc ctataaaatc ggcctcgacg agtataggct caagcttcac    780
cttcagcagc agctcttggc ctatgttctt aatcaggaca agattagagt gggtcacctt    840
agcgtgatga aggagaggct cgacgatctt cgcgttatga tcattcttga cgacgttgaa    900
cacttatatc agcttgaagc cctcgctgat attcgctggt tcggaccagg atcaagggtg    960
atagtgacca ccgagaatag ggagattctc cttcagcatg gaattaagga catctatcat   1020
gttggctttc ctagcgaagg tgaggcgctt atgatctttt gccttagcgc ttttaggcag   1080
ccgagtccac cttacggatt cttgaagctc acctacgaag tggccagtat ctgcggtaac   1140
cttccacttg gacttcacgt tttgggtacc ctgttgtggg gtaaatcaca ggctgattgg   1200
atcgaggaac tccctcggct taaagattgc ttggacggta ggatcgagag tgtattgaag   1260
gtgggttacg agtcactcta tgagaaggat caggctctct tccttcttat tgccgtttat   1320
tttaactatg attacgttga ctacgtgacc tctatgctcg agaacacaaa cgtgctcgac   1380
gttaggctcg gccttaaaaa gttagctaac cgttgcctga ttcagattga tatagatcac   1440
aaccgcaagt ctagagtagt gatgaatcga ctccttcagg taatggcgag ggaagtgatt   1500
agtaagcaaa aaattagtaa gcgtaagatc cttgaggatc ctcaggatat ctgttacgtg   1560
ttggaagagg ctaaaggtaa gggatcagct ttaggactat cgcttgacgt ggccgagatt   1620
aaggaactcg tgattaacaa gaaggccttc aagaagatgt gtaacctcct gatccttaaa   1680
```

```
gtctttaacg aacagaccc tagggactct aagcttcacg ttccagaaga aatggaactg    1740
cctagctcta ttaggctgtt gcactgggag gcttacccta ggaagtcttt tagatttggc    1800
ccagagaacc tcgtgactct aatatggaa tactctgaac ttgagaagct ctggaaggga    1860
actcagccac tcgccaactt gaaagagatg aacctctgcg gctctagctg ccttaaagaa    1920
ttaccagatt tgagtaaagc cgctaactta gagagacttg acgtagccga gtgtaatgct    1980
ctagttgaga tcccttcctc ggtggctaac ttacacaaga tcgtgaactt gcacatggaa    2040
tcctgcgagt cattagaggt tattcctacc cttattaact tggcttcgct aaagataata    2100
aatattcatg attgccctag acttaaatct tttccagacg tccccactag ccttgaagaa    2160
ctggtgatcg aaaaaaccgg agttcaagag ctgcccgcga gttttagaca ttgtaccggt    2220
gtgactacgc tctatatctg ctctaaccgt aatcttaaga cctttagcac gcacctccct    2280
atgggccttc gtaagctcga tctcagtaac tgcggaattg agtgggtcac agattctatt    2340
aaggaccttc acaacctcta ttacttgaag cttagcggct gtaagcgatt agtttccctt    2400
cctgaacttc cttgttcact tgagtgcctc ttcgctgagg actgtactag tctagagcgt    2460
gttagcgact cacttaacat tcctaatgcg cagttcaatt ttataaagtg cttcactctc    2520
gaccgagagg ctaggcgtgc cattatacag caatcctttg ttcacggtaa cgtcattctt    2580
ccagctagag aggtgctcga agaggttgac tatagagctc gaggaaactg cttaactatc    2640 cccctagtg ctttcaatag gtttaaggtg tgcgtggtgc tctcaatcca ttaa         2694
```

<210> SEQ ID NO 34
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
        /note="Nucleotide sequence HCP6, variant 15"
        /mol_type="unassigned DNA"

<400> SEQUENCE: 34

```
atggctagct ctagctctag tcctaggaac tggcgttata acgttttcac gagctttcac     60
ggcccagacg tgaggattaa gttccttagt caccttaggc agcagtttat ctataacggg    120
atcactatgt ttgacgacaa cgggatcgag cgaagtcaga ttatcgcccc ggctcttaag    180
aaggctatcg gcgagtctag gattgctata ctgctcctta gtaagaacta cgcttcgtct    240
tcatggtcgc tcgatgagct tctcgagatc cttaagtgta aagaggatat cggtcagatc    300
gtgatgaccg ttttctacga ggttgaccct agcgacgtta ggaatcagac tggtgatttt    360
gggatcgcct ttaaagagac ttgcgctcac aagaccgaag aggaacgtca aaagtggact    420
caggctctta cgtacgttgg caatattgcc ggtgaggact ttaagcattg gcctaacgag    480
gctaagatga tcgagaagat cgctagggat gttagcgata tccttaacgt gaccccttgt    540
agggacttcg acggaatggt tggacttaac gatcacctta gagagatgga atcacttctc    600
gaccttaaga acgacggcgt taaaatcgtg ggaatttccg gaccagctgg gatcggtaag    660
tctactatcg ctactgccct tcacggtagg cttagtaaca tgtttcagcg aacctgcttc    720
gtggataacc ttagagagtc ctataagata ggcctcgacg agtataggct taagcttcac    780
cttcagcagc agctcatggc ctacgtcctt aatcaggata agattagagt gggtcactta    840
agcgtgatga aggaaaggct cgacgactta cgggtgctga ttattctcga cgacgtggag    900
cacctctacc agcttgaagc tcttgccgat attaggtggt tcggaccagg atcgagggtg    960
```

```
atcgtaacta ccgagaatag ggaaatcctc cttcagcacg ggattaagga tatctatcac   1020
gtggggtttc ctagcgaagg tgaggctctt atgatcttct gccttagcgc cttcaggcag   1080
cctagtccac cctacggatt tcttaagcta acctacgaag tggctagtat atgcgggaac   1140
cttccacttg gacttcacgt gttgggaacc ctgttgtggg gtaagagtca ggctgattgg   1200
attgaggagc tccctcgcct taaggactgc ctcgacggta ggattgagtc agttcttaag   1260
gtgggctatg agagcctcta cgagaaggat caggctctct tcctccttat cgcggtttac   1320
ttcaactacg attacgttga ctacgtgact tctatgctcg agaacactaa cgtgctcgac   1380
gttaggctcg gccttaagaa gcttgctaac cgttgcctga tccaaattga tatcgaccat   1440
aaccgtaagt ctagggttgt gatgaatagg ctcttacagg tgatggctag ggaagtcata   1500
agtaagcaga agattagtaa gcgtaagatc ctcgaggacc ctcaggatat atgctacgtg   1560
ttggaagagg ctaagggtaa gggatcagct ctcggactta gtcttgacgt ggccgagatt   1620
aaggaactcg tgattaacaa gaaagccttt aagaagatgt gtaacctgct gatccttaaa   1680
gtgtttaacg gtaccgatcc cagggacagc aagcttcacg ttcccgaaga gatggaactg   1740
ccgagctcta ttaggctgct tcattgggag gcttacccta ggaagtcttt tagattcggc   1800
ccagagaacc tcgtgaccct taatatggaa tacagcgagc ttgagaaact ctggaaggga   1860
actcagccac tagctaatct taaagagatg aatctctgcg gctcgagctg ccttaaagag   1920
cttccagatc ttagtaaggc cgctaacctt gagaggcttg acgtagcaga atgtaatgct   1980
ctcgttgaaa tcccttcttc agtggctaac cttcataaga tcgttaacct tcatatggaa   2040
tcctgtgagt cactcgaagt tatcccaaca cttattaacc tcgcgtcact taaaattatc   2100
aacattcacg actgccctag gcttaagtcc ttcccagatg tgcctacaag ccttgaggaa   2160
ctggtgattg aaaagacagg cgttcaggaa ctgcctgcta gttttagaca ctgtaccggt   2220
gtgactacac tctatatctg ctctaatcgt aaccttaaaa cctttagcac tcacctccct   2280
atgggcctta ggaagctcga tctgagtaac tgcggaatcg agtgggtgac cgactctatt   2340 aaggacttc acaaccttta ctaccttaag cttagcggct gtaagaggct cgttagcctt   2400
ccagaacttc cttgttcact tgagtgcctc ttcgctgagg attgcactag tcttgagcgt   2460
gttagcgact cactaaacat ccctaacgct cagtttaatt ttattaagtg tttcacgctc   2520
gatagggagg ctaggcgtgc tattattcaa caatccttcg tgcacggtaa cgtgatttta   2580
ccagctcggg aggtgctcga agaggttgat tacagagcta ggggaaattg cctcacaatt   2640
ccacctagtg cttttaatag gtttaaggtc tgcgtcgtgc tctcaatcca ttaa         2694
```

<210> SEQ ID NO 35
<211> LENGTH: 2694
<212> TYPE: DNA
<213> ORGANISM: Artificial Sequence
<220> FEATURE:
<221> NAME/KEY: source
<222> LOCATION: 1..2694
<223> OTHER INFORMATION: /organism="Artificial Sequence"
    /note="Nucleotide sequence HCP6, variant 16"
    /mol_type="unassigned DNA"

<400> SEQUENCE: 35

```
atggctagct ctagctctag tcctaggaac tggcgttaca acgtgttcac tagctttcac     60
ggccccgacg ttaggattaa gttcctaagt caccttaggc agcagtttat ctataacggg    120
atcactatgt tcgatgataa cgggatcgag cgtagtcaaa ttatcgctcc agctcttaag    180
```

```
aaggctatcg gcgagtctag aatcgctatc atgctgctta gtaagaacta cgctagctct    240
agttggtcac tcgacgagct tctcgagatc cttaagtgta aagaggatat tggtcagatc    300
gtgatgaccg tgttctacga ggttgaccct agcgacgtta ggaatcaaac tggcgatttc    360
gggatcgcct ttaaagagac ttgcgctcac aagaccgaag aggaacgtca aaagtggact    420
caggctctta cctacgtggg taatattgcc ggcgaggact ttaagcactg gccaaacgaa    480
gctaagatga tcgagaagat cgctagggac gtttcagaca tccttaacgt gaccccttgt    540
agggacttcg atggaatggt tggacttaac gatcaccttc gagagatgga atcactcctc    600
gacttaaaga cgacggcgt  taagatcgtg ggtattagtg gtccagctgg dataggtaag    660
tctactattg ctactgcact tcacggtagg cttagtaata tgttccagag gacctgcttc    720
gtggataacc ttagagaatc ctataagatc ggcctcgacg agtataggct taagcttcac    780
cttcagcagc agctcttggc ctacgtgctt aatcaggata agattcgggt gggtcacctt    840
agcgtgatga agaaaggct cgacgatctt agggtgctga ttattctcga cgacgttgag    900
cacctctatc agcttgaagc tctcgctgat atcaggtggt tcggaccggg atctaggtg     960 atcgtgacta ccgagaatag ggagatccta ttgcagcacg ggattaagga tatatatcac   1020
gtgggcttcc ctagcgaagg tgaggctctt atgatctttt gccttagcgc ttttaggcag   1080
cctagtccac cctacggatt tcttaagctc acctatgaag tggcttctat ttgcggtaac   1140
cttccacttg gacttcacgt gatgggaact cttttgtggg gtaagagtca ggcggattgg   1200
atagaggaac tcccaaggct taaggattgc ctcgacggta ggattgagtc agttttgaag   1260
gtaggctacg agtcactcta cgagaaggat caggctctct tcctccttat cgccgtttac   1320
tttaactacg actacgtcga ctacgtgacc tcgatgcttg agaacactaa tgtgctcgac   1380
gttaggctcg gccttaagaa acttgctaac cgttgcctga ttcaaatcga tatcgaccac   1440
aaccgtaagt ctagggtggt gatgaacagg ctccttcagg tgatggctag ggaagtgata   1500
agtaagcaga agattagtaa gcgtaagatc ctcgaagacc ctcaggatat ttgctacgtg   1560
ttggaagagg ctaagggtaa gggatcagct ctgggactta gtcttgacgt ggccgagatc   1620
aaggaactcg tgattaacaa gaaagccttt aagaagatgt gtaacctcct gatacttaag   1680
gtgtttaacg gcaccgatcc taggggactct aagcttcacg tcccagaaga gatggaactg   1740
cccagctcta ttaggctgct tcactgggag gcttacccta ggaagtcttt tagattcggc   1800
ccagagaacc tcgtgaccct taatatggaa tactcagagc ttgagaagct ctggaaggga   1860
actcagccac tcgctaacct taaagagatg aacttatgcg gctctagctg ccttaaagag   1920
cttccagatc ttagtaaggc cgctaacctt gaaaggcttg acgttgcaga gtgtaacgcg   1980
ctcgttgaga tcccttcgtc tgtggctaat cttcacaaga tcgttaacct tcacatggag   2040
tcctgcgagt cactcgaggt tatccctacc cttattaacc tcgcaagcct taagattatt   2100
aacattcacg actgccctag acttaagtcc ttcccagatg tgcctactag ccttgaggaa   2160
atggtgatcg aaaagaccgg cgttcaagag ctgcccgcgt cgtttagaca ctgtaccggt   2220
gtgactaccc tctatatctg ctctaaccgt aaccttaaga cctttagcac tcacctccct   2280
atgggcctta ggaagctcga tcttagtaac tgcggtatcg agtgggtgac cgactctatt   2340
aaggaccttc acaacctcta ctaccttaag cttagcggct gtaagaggct cgttagcctt   2400
ccagaacttc cttgctcact tgagtgcctc ttcgctgagg attgcacaag tcttgagcgt   2460
gttagcgact cacttaatat ccccaacgct cagtttaact ttattaagtg cttcacccctc   2520 gatagggaag ctaggcgtgc tataattcag cagtccttcg ttcatggtaa cgtaatcctt   2580
```

```
ccagctagag aggtgctcga agaggttgac tatagagcta ggggaaattg cctcactatc    2640 cccoctagtg cctttaacag gtttaaggtg tgcgtggtac tcagcatcca ttaa          2694
```

The invention claimed is:

1. A method for preventing, reducing or delaying soybean rust infection in a soybean plant, a soybean plant part, or a soybean plant cell, said method comprising:
   providing a transgenic soybean plant, transgenic soybean plant part, or transgenic soybean plant cell with an exogenous nucleic acid encoding an HCP6 protein comprising an amino acid sequence with at least 85% identity with SEQ ID NO: 4, wherein the HCP6 protein confers increased resistance against soybean rust thereto in comparison to a wild type plant, wild type plant part or wild type plant cell; and growing the transgenic soybean plant, transgenic soybean plant part, or transgenic soybean plant cell in the presence of a soybean rust pathogen, wherein soybean rust infection is prevented, reduced, or delayed in the transgenic soybean plant, transgenic soybean plant part, or transgenic soybean plant cell as compared to a wild type soybean plant, wild type soybean plant part, or wild type soybean plant cell.

2. The method of claim 1, wherein the exogenous nucleic acid is in functional linkage with a promoter.

3. A recombinant vector construct comprising:

(a) a nucleic acid encoding a protein having an amino acid sequence with at least 85% identity with SEQ ID NO: 4 operably linked with (b) a heterologous promoter and (c) a transcription termination sequence, wherein expression of said recombinant vector construct in a plant, plant part, or plant cell confers increased resistance against soybean rust thereto in comparison to a wild type plant, wild type plant part, or wild type plant cell.

4. The method of claim 2, wherein the promoter is a constitutive promoter, pathogen-inducible promoter, a mesophyll-specific promoter or an epidermis specific-promoter.

5. A transgenic plant, transgenic plant part, or transgenic plant cell comprising an exogenous nucleic acid encoding an HCP6 protein comprising an amino acid sequence with at least 85% identity with SEQ ID NO: 4, wherein expression of said exogenous nucleic acid in the transgenic plant, transgenic plant part, or transgenic plant cell confers increased resistance against soybean rust thereto in comparison to a wild type plant, wild type plant part, or wild type plant cell.

6. A method for the production of a transgenic plant, transgenic plant part, or transgenic plant cell having increased soybean rust resistance, comprising (a) introducing the recombinant vector construct of claim 3 into a plant, a plant part, or a plant cell; and (b) generating a transgenic plant, transgenic plant part, or transgenic plant cell from the plant, plant part or plant cell.

7. The method of claim 6, further comprising the step of harvesting the seeds of the transgenic plant and planting the seeds and growing the seeds to plants, wherein the grown plants comprise the recombinant vector construct.

8. A harvestable part of the transgenic plant of claim 5, wherein the part comprises the exogenous nucleic acid encoding a protein having an amino acid sequence with at least 85% identity with SEQ ID NO: 4.

9. A product derived from the plant of claim 5, wherein the product comprises the exogenous nucleic acid encoding a protein having an amino acid sequence with at least 85% identity with SEQ ID NO: 4.

10. A method for the production of a product comprising a) growing the plant of claim 5; and b) producing said product from or by the plant or a part of the plant.

11. The method of claim 10 comprising a) growing the plant and removing the harvestable parts from the plant; and b) producing said product from or by the harvestable parts of the plant.

12. The method of claim 10, wherein the product is meal or oil.

13. The method of claim 1, wherein the resistance against soybean rust is resistance against *Phakopsora meibomiae, Phakopsora pachyrhizi*, or a combination thereof.

14. A method for breeding a fungal resistant plant comprising (a) crossing the plant of claim 5 with a second plant;

(b) obtaining seed from the cross of step (a);

(c) planting said seeds and growing the seeds to plants; and (d) selecting from the plants produced in step(c) plants expressing the HCP6 protein.

15. A method for controlling soybean rust in a soybean plant, said method comprising providing a transgenic soybean plant comprising an exogenous nucleic acid encoding an HCP6 protein having an amino acid sequence with at least 85% identity to SEQ ID NO: 4, wherein expression of the nucleic acid leads to increased soybean rust resistance in said soybean plant as compared to a wild type soybean plant such that soybean rust is controlled in the transgenic soybean plant.

16. The method of claim 15, wherein the soybean rust that is controlled is *Phakopsora meibomiae* and/or *Phakopsora pachyrhizi.*

17. The recombinant vector construct of claim 3, wherein the nucleic acid encodes an HCP6 protein comprising an amino acid sequence with at least 90% identity with SEQ ID NO: 4.

18. The recombinant vector construct of claim 3, wherein all of the amino acid residues in the HCP6 protein not identical to the amino acid sequence of SEQ ID NO:4 are conservative amino acid substitutions.

19. The transgenic plant, transgenic plant part, or transgenic plant cell of claim 5, wherein the exogenous nucleic acid encodes an HCP6 protein comprising an amino acid sequence with at least 90% identity with SEQ ID NO: 4.

20. The transgenic plant, transgenic plant part, or transgenic plant cell of claim 5, wherein all of the amino acid residues in the HCP6 protein not identical to the amino acid sequence of SEQ ID NO:4 are conservative amino acid substitutions.

21. The method of claim 15, wherein the exogenous nucleic acid encodes an HCP6 protein comprising an amino acid sequence with at least 90% identity with SEQ ID NO: 4.

22. The method of claim 15, wherein all of the amino acid residues in the HCP6 protein not identical to the amino acid sequence of SEQ ID NO:4 are conservative amino acid substitutions.

23. The method of claim 1, wherein the exogenous nucleic acid encodes an HCP6 protein comprising an amino acid sequence with at least 90% identity with SEQ ID NO: 4.

24. The method of claim 1, wherein all of the amino acid residues in the HCP6 protein not identical to the amino acid sequence of SEQ ID NO:4 are conservative amino acid substitutions.

* * * * *